(12) United States Patent
Davies et al.

(10) Patent No.: US 11,590,112 B2
(45) Date of Patent: Feb. 28, 2023

(54) METHODS AND COMPOUNDS FOR THE TREATMENT OR PREVENTION OF HYPERCYTOKINEMIA AND SEVERE INFLUENZA

(71) Applicant: Orph Pharma IP Company Limited, London (GB)

(72) Inventors: Adrian Huw Davies, London (GB); Pui-Man Choy, London (GB); Vinay Saunders, London (GB); Basma Bahsoun, London (GB); Surender Vashist, London (GB); Neil Edward Torbett, London (GB); Paul Andrew Whittaker, London (GB)

(73) Assignee: Orph Pharma IP Company Limited, London (GB)

( * ) Notice: Subject to any disclaimer, the term of this patent is extended or adjusted under 35 U.S.C. 154(b) by 2 days.

(21) Appl. No.: 16/957,063

(22) PCT Filed: Dec. 20, 2018

(86) PCT No.: PCT/GB2018/053732
§ 371 (c)(1),
(2) Date: Jun. 22, 2020

(87) PCT Pub. No.: WO2019/122909
PCT Pub. Date: Jun. 27, 2019

(65) Prior Publication Data
US 2020/0360351 A1 Nov. 19, 2020

(30) Foreign Application Priority Data
Dec. 22, 2017 (GB) ..................... 1721793

(51) Int. Cl.
A61K 31/437 (2006.01)
A61P 31/16 (2006.01)
A61K 45/06 (2006.01)

(52) U.S. Cl.
CPC ............ *A61K 31/437* (2013.01); *A61P 31/16* (2018.01); *A61K 45/06* (2013.01)

(58) Field of Classification Search
CPC .................................................. A61K 31/437
USPC ...................................................... 514/303
See application file for complete search history.

(56) References Cited

U.S. PATENT DOCUMENTS

| 8,536,194 B2* | 9/2013 | Almansa Rosales ... A61P 37/00 514/303 |
| 8,697,627 B2* | 4/2014 | Alam .................... C07D 211/16 514/1 |
| 2010/0151042 A1 | 6/2010 | Liang et al. |
| 2011/0003848 A1 | 1/2011 | Butcher |

FOREIGN PATENT DOCUMENTS

| JP | 2003-516314 | 5/2003 |
| JP | 2006-519205 | 8/2006 |
| JP | 2017-515910 | 6/2017 |
| WO | WO 01/19322 A2 | 3/2001 |
| WO | WO 02/059083 A2 | 8/2002 |

(Continued)

OTHER PUBLICATIONS

Soliva et al., Journal of Medicinal Chemistry (2007), 50(2), 283-293.*
Mihara et al., British Journal of Pharmacology (2008), 154(1), 153-164.*
Bagley et al., Future Medicinal Chemistry (2010), 2(2), 193-201.*
Wang et al., Journal of Chemical Information and Modeling (2011), 51(11), 2821-2828.*
Rui Liu et al: "Mouse Lung Slices: An ex vivo model for the evaluation of antiviral and anti-inflammatory agents against influenza viruses", Antiviral Research, vol. 120, Aug. 1, 2015, (Aug. 1, 2015), pp. 101-111, XP055355559.

(Continued)

*Primary Examiner* — Niloofar Rahmani
(74) *Attorney, Agent, or Firm* — Jon E. Gordon; Haug Partners LLP

(57) ABSTRACT

The invention provides a p38 MAPK inhibitor of Formula I, or a pharmaceutically acceptable salt or solvate thereof: Formula I for use in the treatment or prevention of hypercytokinemia in a human patient; wherein R is $C_{1-3}$alkyl, optionally substituted by one or more halo, $NR^1R^2$ or hydroxy, and $R^1$ and $R^2$ are independently H, halo or $C_{1-3}$alkyl, optionally substituted by one or more F. Also provided are compositions for use in the treatment or prevention of hypercytokinemia comprising the p38 MAPK inhibitor of Formula I; and methods for treating or preventing hypercytokinemia in a human patient in need thereof comprising administering to the patient a therapeutically or prophylactically effective amount of a p38 MAPK inhibitor of Formula I. The invention also provides a p38 MAPK inhibitor and an antimicrobial agent, such as an antiviral agent, for use in the treatment or prevention of hypercytokinemia.

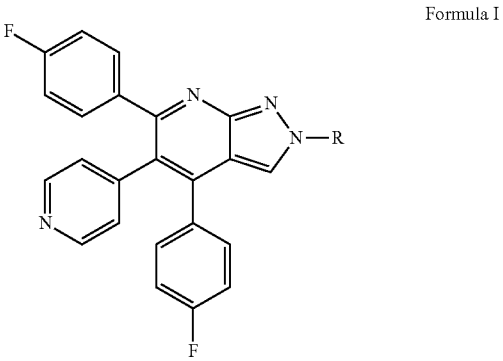

Formula I

19 Claims, 24 Drawing Sheets

(56) References Cited

FOREIGN PATENT DOCUMENTS

| WO | WO 2004/076450 A1 | 9/2004 |
|---|---|---|
| WO | WO 2010/029167 A2 | 3/2010 |
| WO | WO 2010/038085 A2 | 4/2010 |
| WO | WO 2015/173788 A1 | 11/2015 |
| WO | WO 2016/154329 A2 | 9/2016 |
| WO | WO 2017/151409 A1 | 9/2017 |
| WO | WO 2018/007788 A1 | 1/2018 |

OTHER PUBLICATIONS

Y. Borgeling et al., "Inhibition of p38 Mitogen-activated Protein Kinase Impairs Influenza Virus-induced Primary and Secondary Host Gene Responses and Protects Mice from Lethal H5N1 Infection", Journal of Biological Chemistry, vol. 289, No. 1, Nov. 4, 2013 (Nov. 4, 2013), pp. 13-27, XP055161048.

Critical Care Medicine, vol. 43, No. 9, 2015, pp. 1859-1869 Christie et al. "A randomized dose-escalation study of the safety and anti-inflammatory activity of the p38 mitogen-activated protein kinase inhibitor dilmapimod in severe trauma subjects at risk for acute respiratory distress syndrome".

Biochemical and Biophysical Research, vol. 477, No. 3, 2016, pp. 311-316 Choi et al. "A novel p38 mitogen activated protein kinase (MAPK) specific inhibitor suppresses respiratory syncytial virus and influenza A virus replication by inhibiting virus-induced p38 MAPK activation".

Acta Virologica, vol. 58, 2014, pp. 374-379 [available via http://www.elis.sk/index.php?page=shop.product_details&flypage=flypage.tpl&product_id=4096&category _id=114&option=com_virtuemart&vmcchk=1&Itemid=1] Wei et al. "Roles of p38 MAPK in the regulation of the inflammatory response to swine influenza virus-induced acute lung injury in mice".

Journal of Virology, vol. 79,No. 16, 2005, pp. 10147-10154 [available via https://www.ncbi.nlm.nih.gov/pmc/articles/PMC1182678/] Lee et al. "p38 mitogen-activated protein kinase-dependent hyperinduction of tumor necrosis factor alpha expression in response to avian influenza virus HSN 1".

International Journal of Molecular Sciences, vol. 14, 2013, pp. 7327-7340 [available via https://www.ncbi.nlm.nih.gov/pmc/articles/PMC3645688/] Law et al. "A role for protein phosphatase 2A in regulating p38 mitogen activated protein kinase activation and tumor necrosis factor-alpha expression during influenza virus infection".

The Journal of lmmunology, vol. 164, 2000, pp. 3222-3228 [available via http://www.jimmunol.org/content/164/6/3222.long] Kujime et al. "p38 mitogen-activated protein kinase and c-Jun-NH$_2$- terminal kinase regulates RANTES production by influenza virus-infected human bronchial epithelial cells".

Turkish Archives of Pediatrics, vol. 51, 2016, pp. 63-71 [available via https://www.ncbi.nlm.nih.gov/pmc/articles/PMC4959743/] Ciftci et al. "Influenza and the use of oseltamivir in children".

Journal of Virology, vol. 84, No. 21, 2010, pP. 11359-11373. Marchant et al. "Toll-like receptor 4-mediated activation of p38 mitogen-activated protein kinase is a determinant of respiratory virus entry and tropism".

CDC website for Influenza—What you should know about Flu Antiviral Drugs, accessed on Jun. 8, 2020.

International Search Report and Written Opinion DATED Mar. 13, 2019 in corresponding International Application No. PCT/GB2018/053732.

Search Report issued in corresponding United Kingdom Application No. GB1721793.6.

International Search Report and Written Opinion dated Aug. 30, 2017 in corresponding International Application No. PCT/GB2017/051865.

Search Report issued in corresponding Application No. GB 1611712.9.

An SC et al, Triple combinations of neuraminidase inhibitors, statins and fibrates benefit the survival of patients with lethal avian influenza pandemic, Medical Hypotheses, 2011; 77(6): 1054-157.

Armstrong SM et al., Endothelial activation and dysfunction in the pathogenesis of influenza A virus infection, Virulence, 2013; 4(6): 537-542.

Bermejo-Martin JF, et al, Macrolides for the treatment of severe respiratory illness caused by novel H1N1 swine influenza viral strains, J Infect Developing Countries, 2009; 3(3): 159-161.

Brun-Buisson et al., Early corticosteroids in severe influenza A/H1N1 pneumonia and acute respiratory distress syndrome, Am J Respir Crit Care Med. May 1, 2011;183(9):1200-6.

Croft, M., The role of TNF superfamily members in T-cell function and diseases, Nat Rev Immunol, 2009; 9: 271-85.

Darwish et al., Immunomodulatory Therapy for Severe Influenza, Expert Rev Anti Infect Ther., Jul. 2011; 9(7): 807-22, doi: 10.1586/eri.11.56.

Fedson DS, Confronting the next influenza pandemic with anti-inflammatory and immunomodulatory agents: why they are needed and how they might work, Influenza and Other Respiratory Viruses, 2009; 3(4): 129-142.

Fedson DS, Confronting an influenza pandemic with inexpensive generic agents: can it be done?, Lancet Infect. Dis., 2008; 8: 571-76.

Fedson DS, Treating influenza with statins and other immunomodulatory agents, Antiviral Research, 2013; 99(3): 417-435.

Galan-Arriero I, et al. Early treatment with UR13870, a novel inhibitor of p38α mitogenous activated protein kinase, prevents hyperreflexia and anxiety behaviors, in the spared nerve injury model of neuropathic pain. Neurosci. Lett. Sep. 14, 2015;604:69-74.

Hoang et al. (Patient-based transcriptome-wide analysis identify interferon and ubiquitination pathways as potential predictors of influenza A disease severity, PloS One 2014, 9:e111640e).

Hui et al., Adjunctive Therapies and Immunomodulatory Agents in the Management of Severe Influenza, Antiviral Research, 2013; 98: 410-416.

Hui & Lee, Adjunctive Therapies and Immunomodulatory Agents for Severe Influenza, Influenza and Other Respiratory Viruses, 2013; 7 (suppl. 3): 52-59.

Lee, N. et al., Cytokine response patterns in severe pandemic 2009 H1N1 and seasonal influenza among hospitalised adults, PloS One, 2011; 6: e26050.

Lee, N. et al., Outcomes of adults hospitalised with severe influenza, Thorax, 2010; 65: 510-515.

Lee N. et al., Viral clearance and inflammatory response patterns in adults hospitalised for pandemic 2009 influenza A (H1N1) virus pneumonia, Antiviral Therapy, 2011; 16: 237-47.

Liu et al., Cellular & Molecular Immunology, 2015; 1-8, doi: 10.1038/cmi.2015.74.

Mihara K, et al. A potent and selective p38 inhibitor protects against bone damage in murine collagen-induced arthritis: a comparison with neutralization of mouse TNFalpha., Br. J. Pharmacol., May 2008; 154(1):153-64.

Sato K et al, Therapeutic Effect of Erythromycin on Influenza Virus-induced Lung Injury in Mice, Am J Respir Crit Care Med, 1998; 157: 853-857.

Teijaro JR et al., Endothelial Cells are Central Orchestrators of Cytokine Amplification during Influenza Vims Infection, Cell, 2011; 146: 980-991.

Xing, L., MAP Kinase 2015, vol. 4:5508.

Zarubin and Han, Cell Research (2005) 15, 11-18. doi:10.1038/sj.cr.7290257.

WHO factsheet No. 211: https://web.archive.org/web/20160613040907/http://www.who.int/mediacentre/factsheets/fs211/en/.

WHO Guidelines for Pharmacological Management of Pandemic Influenza A(H1N1) 2009 and other Influenza Viruses, Revised Feb. 2010, Part I Recommendations, p. 5.

Jian-Ping Dai et al., Identification of 23-(S)-2 Amino-3-Phenylpropanoyl-Silybin as an Antiviral Agent for Influenza a Virus Infection In Vitro and In Vivo, Antimicrobial Agents and Chemotherapy, Sep. 2013, vol. 57, No. 9, p. 4433-4443.

Cuenda et al. (Mar. 24, 2007) "p38 MAP-Kinases pathway regulation, function and role in human diseases", Biochimica et Biophysica Acta.

(56) References Cited

OTHER PUBLICATIONS

Geiler et al. (Sep. 24, 2010) "Comparison of pro-inflammatory cytokine expression and cellular signal transduction in human macrophages infected with different influenza A viruses", Med Microbiol Immunol.
Hui et al. (Jan. 15, 2009) "Induction of Proinflammatory Cytokines in Primary Human Macrophages by Influenza A Virus (H5N1) Is Selectively Regulated by IFN Regulatory Factor 3 and p38 MARK", The Journal of Immunology.
Geiler et al. (Sep. 2, 2009) "N-acetyl-L-cysteine (NAC) inhibits virus replication and expression of pro-inflammatory molecules in A549 cells infected with highly pathogenic H5N1 influenza A virus", Biochemical Pharmacology.
Wu et al. (Jan. 20, 2010) "Innate immune response to H3N2 and H1N1 influenza virus infection in a human lung organ culture model", Virology.
Liu et al. (May 26, 2015) "Mouse lung slices: An ex vivo model for the evaluation of antiviral and anti-inflammatory agents against influenza viruses", Antiviral Research.
Paquette et al. (Jun. 5, 2012) "Interleukin-6 Is a Potential Biomarker for Severe Pandemic H1N1 Influenza A Infection", PLoS One.
Ramos et al. (Jul. 20, 2015) "Modulating the innate immune response to influenza A virus: potential therapeutic use of anti-inflammatory drugs", Frontiers in Immunology.
Neuroscience Letters, 2015, vol. 604, pp. 69-74.
English Translation of the Office Action dated Jun. 1, 2021 in corresponding Japanese Patent Application No. JP2018-569081.
Office Action dated Dec. 12, 2022 issued in co-pending Israeli Patent Application No. 275573, and its'English Translation.
Office Action issued in co-pending Japanese Patent Application No. 2020-534928, and it'English Translation.

* cited by examiner

METHODS AND COMPOUNDS FOR THE TREATMENT OR PREVENTION OF HYPERCYTOKINEMIA AND SEVERE INFLUENZA

CROSS-REFERENCE TO RELATED APPLICATIONS

This application is the National Stage entry under 35 U.S.C. § 371 of International Application No. PCT/GB2018/053732 filed on Dec. 20, 2018, published on Jun. 27, 2019 under Publication Number WO 2019/122909 A1, which claims the benefit of priority under 35 U.S.C. § 119 of United Kingdom Patent Application Number 1721793.6 filed on Dec. 22, 2017, the entireties of which are herein incorporated by reference.

FIELD OF THE INVENTION

The present invention relates to methods and compounds for the treatment or prevention of hypercytokinemia and, in particular, hypercytokinemia associated with severe influenza.

The invention also provides pharmaceutical compositions for the treatment or prevention of hypercytokinemia and hypercytokinemia associated with severe influenza.

BACKGROUND TO THE INVENTION

Hypercytokinemia is defined as a sudden surge in the circulating levels of pro-inflammatory cytokines, such as IL-1, IL-6 and TNF (Croft, M., The role of TNF superfamily members in T-cell function and diseases, *Nat Rev Immunol*, 2009; 9: 271-85).

Hypercytokinemia, or "cytokine storm", or "cytokine cascade", is associated with various conditions including infectious diseases, non-infectious diseases, autoimmune reactions and adverse drug reactions. Inflammation is part of the complex biological response of body tissues to harmful stimuli, such as viruses, damaged cells, or irritants. It is a protective response that involves the immune system, blood vessels and numerous proteins. The purpose of inflammation is to eliminate the initial cause of cell injury, to clear out dead and dying cells and to initiate tissue repair. In normal circumstances inflammation is short lived and repair to damaged tissues normally starts 2 to 3 days after the onset of symptoms.

Hypercytokinemia develops when the inflammatory response is exaggerated and high levels of pro-inflammatory proteins (cytokines) are released which can lead to damage of the blood vessels in the lung and other tissues resulting in liquid leaking into tissues (oedema). Rather than being protective the inflammatory response becomes destructive. This exaggerated inflammatory response can be viewed as a non-linear process where there is a critical point—a phase transition, tipping point, or threshold—where the normal inflammatory response becomes an abnormal response.

A variety of anti-inflammatory drugs and adjunct approaches have been adopted in an attempt to target hypercytokinemia. These include treatment with corticosteroids, aspirin, monoclonal antibodies (MAbs), anti-cytokine and anti-chemokine agents, plasma exchange, and statins. Despite these efforts, none of these approaches have proved to be effective, and some have worsened the outcome (Brun-Buisson et al., Early corticosteroids in severe influenza A/H1N1 pneumonia and acute respiratory distress syndrome, Am J Respir Crit Care Med. 2011 May 1; 183(9):1200-6). The therapeutic approaches of the present invention are aimed at balancing the response by attenuating the inflammatory response rather than ablating it, thus reducing the damaging effects caused by the exaggerated inflammatory response whilst preserving the host's innate protective response.

Hypercytokinemia is seen in severe infections with three major influenza viruses: the pandemic 1918-19 Spanish H1N1 influenza; H5N1 avian influenza and; the pandemic H1N1 influenza of 2009. When compared to human H1N1, H5N1 viruses are more potent inducers of pro-inflammatory cytokines in primary human respiratory epithelial cells, and this hyperinduction of cytokines is likely to contribute to the disease severity of H5N1. The exact mechanism of hypercytokinemia in influenza is unknown, but endothelial cells have been identified as central regulators of "cytokine storm" (Teijaro J R et al., Endothelial Cells are Central Orchestrators of Cytokine Amplification during Influenza Virus Infection, Cell, 2011; 146: 980-991).

Influenza occurs globally with an annual attack rate estimated at 5%-10% in adults and 20%-30% in children. Illnesses can result in hospitalization and death mainly among high-risk groups (the very young, elderly or chronically ill). Worldwide, these annual epidemics are estimated to result in about 3 to 5 million cases of severe illness, and about 250,000 to 500,000 deaths. (See WHO factsheet number 211: https://web.archive.org/web/20160613040907/http://www.who.int/mediacentre/factsheets/fs 211/en/).

In North America, seasonal influenza causes excess hospitalisations in 230-1670 per 100,000 persons aged >65 years, 32,000 respiratory/cardiovascular deaths and 43,000 all-cause deaths annually. Persons with chronic medical conditions (e.g. pulmonary, cardiovascular, liver, renal and neurological diseases, diabetes or immunosuppression) have a >30-fold increase in risk of hospitalisation and death.

Among the circulating seasonal influenza subtypes, H3N2 is usually a more frequent cause of severe illness and hospitalisation. (See Lee, N. et al., Outcomes of adults hospitalised with severe influenza, Thorax, 2010; 65: 510-515).

The situation can be even worse during influenza pandemics. In early 2009, a novel influenza A/H1N1 virus (pH1N1) emerged and rapidly caused a pandemic. It has been estimated that in some populations, up to 20-40% of individuals were affected and resulted in excessive hospitalizations and deaths. In the United States, 195,000-403,000 people were hospitalized for severe pH1N1 infection and 8,870-18,300 died by April 2010. The pH1N1 virus has continued to co-circulate with the seasonal influenza viruses in the community.

While most patients develop mild upper respiratory-tract infection with pH1N1, some progress to develop severe lower respiratory-tract complications, such as, for example, pneumonia, or transition to experiencing symptoms that do not resolve or improve after several days (>2 days). In contrast to seasonal influenza, young adults and previously healthy individuals may also develop severe respiratory complications such as, for example, pneumonia and acute respiratory distress syndrome (ARDS). Among hospitalized adults, between 9-34% may require intensive care because of progressive respiratory failure, which can be associated with high mortality (14-46%); notably, some of the manifestations (e.g. pneumonia, ARDS, multi-organ failure) are quite similar to those of H5N1 avian influenza. (See Lee, N. et al., Cytokine response patterns in severe pandemic 2009 H1N1 and seasonal influenza among hospitalised adults, PloS One, 2011; 6: e26050).

WO 01/19322 A2 (SmithKline Beecham Corp) claims a method of treating influenza-induced pneumonia which method comprises administering to the human an effective amount of a CB SP/p38 inhibitor.

The p38 MAP kinases comprise a mitogen-activated protein kinase subfamily that regulates a variety of cellular processes including cell growth processes, cell differentiation, apoptosis and cellular responses to inflammation. The p38 MAP kinases are regulated by cytokine receptors and can be activated in response to bacterial or viral pathogens.

WO 2004/076450 A1 discloses the use of certain pyrazolopyridine derivatives for the treatment or prevention of diseases mediated by TNF-α, IL-1, IL-6 and/or IL-8, including immune, autoimmune and inflammatory diseases, cardiovascular diseases, infectious diseases, bone resorption disorders, neurodegenerative diseases, proliferative diseases and processes associated with the induction of cyclooxygenase-2.

WO 02/059083 A2 (SmithKline Beecham Corp) claims the use of substituted 2,4,8-trisubstituted-8H-pyrido[2,3-d]pyrimidin-7-one compounds and compositions for treating a wide range of CBSP/p38 kinase mediated diseases, including ARDS, chronic obstructive pulmonary disease and influenza-induced pneumonia.

U.S. 2011/003848 A1 (Butcher) discloses the use of polymorphic form of the p38 MAP kinase inhibitor, N-[3-tert-butyl-1-(3-chloro-4-hydroxyphenyl)-1H-pyrazol-5-yl]-N'-{2-[(3-{2-[(2-hydroxyethyl)sulfanyl]phenyl}[1,2,4]triazolo[4,3-a]pyridin-6-yl)sulfanyl]benzyl}urea, for treating obstructive, restrictive or inflammatory airways diseases of whatever type, etiology or pathogenesis.

Meanwhile, WO 2015/173788 A1 (Westfälische Wilhelms-Universität Münster) claims a MEK inhibitor, p38 inhibitor and/or NF-κB inhibitor for use in a method for the prophylaxis and/or treatment of a co-infection comprising a bacterial infection and an influenza virus infection or a bacterial infection alone.

A p38 MAPK inhibitor is disclosed in Mihara K, et al. A potent and selective p38 inhibitor protects against bone damage in murine collagen-induced arthritis: a comparison with neutralization of mouse TNFalpha., *Br. J. Pharmacol.*, 2008 (May);154(1): 153-64, and Galan-Arriero I, et al. Early treatment with UR13870, a novel inhibitor of p38α mitogenous activated protein kinase, prevents hyperreflexia and anxiety behaviors, in the spared nerve injury model of neuropathic pain. *Neurosci. Lett.* 2015 (Sep.) 14; 604:69-74.

Generally, as discussed in more detail below, a number of different anti-inflammatory agents have been proposed in the art for treating inflammation associated with influenza infection.

The World Health Organisation (WHO) defines severe influenza as: Influenza in patients who present clinical and/or radiological signs of lower respiratory tract disease, central nervous system (CNS) involvement, severe dehydration or present secondary complications, such as renal failure, multi-organ failure and septic shock (other complications can include rhabdomyolysis and myocarditis); influenza where there is exacerbation of underlying chronic disease; influenza where there is any other condition or clinical presentation that requires hospital admission for clinical management; and influenza where there are any of the following signs and symptoms of progressive disease:

Symptoms and signs suggesting oxygen impairment or cardiopulmonary insufficiency: Shortness of breath (with activity or at rest), difficulty in breathing, tachypnoea, presence of cyanosis, bloody or coloured sputum, chest pain, and low blood pressure; in children, fast or laboured breathing; and hypoxia, as indicated by pulse oximetry or arterial blood gases;

Symptoms and signs suggesting CNS complications: Altered mental status, unconsciousness, drowsiness, or difficult to awaken and recurring or persistent convulsions (seizures), confusion, severe weakness, or paralysis;

Evidence of sustained or spreading virus replication or invasive secondary bacterial infection based on laboratory testing or clinical signs (e.g. persistent or recurrent high fever and other symptoms beyond 2 or 3 days without signs of resolution); and Severe dehydration, manifested as decreased physical or mental activity, dizziness, decreased urine output, and lethargy. (See WHO Guidelines for Pharmacological Management of Pandemic Influenza A(H1N1) 2009 and other Influenza Viruses, Revised February 2010, Part I Recommendations, p. 5).

Uncomplicated influenza is a mild inflammation of the upper respiratory tract. Inflammation is part of the complex biological response of body tissues to harmful stimuli damaging cells, such as viruses, toxins or irritants; it is a protective response that involves the immune system, blood vessels and numerous proteins. The purpose of inflammation is to eliminate the initial cause of cell injury, clear out dead and dying cells and to initiate tissue repair. In uncomplicated influenza the inflammation is short lived and repair to the damaged epithelial cell lining of the upper airways starts about 2-3 days after onset of symptoms.

In contrast to uncomplicated influenza, the inflammatory response in severe influenza is exaggerated or extended respectively. Rather than being protective, the response becomes destructive. High levels of pro-inflammatory proteins (cytokines) in the blood are an early indication of poor clinical outcomes in influenza patients (Lee, N. et al. 2011). In these patients the exaggerated inflammatory response can lead to damage of the blood vessels in the lung and other tissues resulting in leakage of liquid into the tissue (oedema). Accumulation of fluid and immune cells in the lungs can lead to pneumonia, acute lung injury and ARDS and respiratory failure in severe cases. The exaggerated inflammatory response in severe influenza can be viewed as a non-linear process where there is a critical point—a phase transition, or tipping point—when the normal inflammatory response becomes an abnormal or more destructive response. In severe influenza, rather than going down a resolution path after peak symptoms at around day 3 after infection, patients progress to develop other respiratory complications, a process driven by an exaggerated inflammatory response.

Armstrong S M et al., Endothelial activation and dysfunction in the pathogenesis of influenza A virus infection, *Virulence*, 2013; 4(6): 537-542, review evidence in support of endothelial activation and dysfunction as a central feature preceding the development of severe influenza.

Using gene expression microarrays to compare the transcriptomic profiles of influenza-infected patients with severe, moderate and mild symptoms with febrile patients of unknown etiology, Hoang et al. (Patient-based transcriptome-wide analysis identify interferon and ubiquitination pathways as potential predictors of influenza A disease severity, PloS One 2014, 9: e111640e) reported that influenza-infected patients, regardless of their clinical outcomes, had a stronger induction of antiviral and cytokine responses and a stronger attenuation of NK and T cell responses in comparison with those with unknown etiology and that interferon and ubiquitination signalling were strongly attenuated in patients with the most severe outcomes in comparison with those with moderate and mild outcomes. This agrees with the inventors' own data, which show elevated cytokine levels in serum from patients hospitalised for severe influenza relative to influenza-infected individuals without severe influenza (see Example 5 below).

Hoang et al., 2014 found p38 MAPK signalling to be up-regulated in moderate as well as severe patients. MMP9, SOCS3, IFITMs, TLR10, RIG-I, CD244 and NCR3 were proposed as candidate genes for further studies. However, targeting individual cytokines is unlikely to have broad anti-inflammatory effects that are required, and redundancy in the inflammatory response system means that knocking out multiple cytokines simultaneously is likely to be required for a therapy to be effective.

U.S. 2010/0151042 A1 (Liang et al.) claims a method for reducing the severity, intensity or duration of complications or symptoms associated with an influenza infection, wherein the method comprises diagnosing a subject with the influenza infection; and concurrently administering to the subject an effective amount of a cysteamine compound and a second viral therapeutic. The complications associated with the influenza viral infection may comprise rhinitis, bacterial infections, cardiac complications, neurologic complications, myositis, renal failure, pulmonary fibrosis, exacerbations of asthma, exacerbations of chronic obstructive pulmonary disease, empyema or heart failure. The second viral therapeutic may be selected from the group consisting of: amantadine, rimantadine, ribavirin, idoxuridine, trifluridine, vidarabine, acyclovir, ganciclovir, foscarnet, zidovudine, didanosine, zalcitabine, stavudine, famciclovir, oseltamivir phosphate, zanamivir, valaciclovir, antitussives, mucolytics, expectorants, antipyretics, analgesics and nasal decongestants.

Immunomodulatory therapy for severe influenza has been reviewed by Hui et al., Adjunctive Therapies and Immunomodulatory Agents in the Management of Severe Influenza, *Antiviral Research*, 2013; 98: 410-416; Hui & Lee, Adjunctive Therapies and Immunomodulatory Agents for Severe Influenza, *Influenza and Other Respiratory Viruses*, 2013; 7 (suppl. 3): 52-59; and Liu et al., *Cellular & Molecular Immunology*, 2015; 1-8, doi: 10.1038/cmi.2015.74.

Darwish et al., Immunomodulatory Therapy for Severe Influenza, *Expert Rev Anti Infect Ther.*, 2011 (July); 9(7): 807-22, doi: 10.1586/eri.11.56, describe the influenza viral and host pathogenicity determinants, present the evidence supporting the use of immunomodulatory therapy to target the host inflammatory response as a means to improve clinical outcome in severe influenza, and review the experimental data on investigational immunomodulatory agents targeting the host inflammatory response in severe influenza, including anti-TNF therapy, statins, glucocorticoids, cyclooxygenase-2 inhibitors, macrolides, peroxisome proliferator-activated receptor agonists, AMP-activated protein kinase agonists and high mobility group box 1 antagonists, concluding with a rationale for the use of mesenchymal stromal (stem) cells and angiopoietin-1 therapy against deleterious influenza-induced host responses that mediate end-organ injury and dysfunction.

Fedson D S, Confronting an influenza pandemic with inexpensive generic agents: can it be done?, *Lancet Infect. Dis.*, 2008; 8: 571-76, proposes research to determine whether statins, fibrates, chloroquines and other generic agents could mitigate the effects of an H5N1 avian influenza A pandemic. See also Fedson D S, Confronting the next influenza pandemic with anti-inflammatory and immunomodulatory agents: why they are needed and how they might work, *Influenza and Other Respiratory Viruses*, 2009; 3(4): 129-142, and Fedson D S, Treating influenza with statins and other immunomodulatory agents, *Antiviral Research*, 2013; 99(3): 417-435.

An S C et al, Triple combinations of neuraminidase inhibitors, statins and fibrates benefit the survival of patients with lethal avian influenza pandemic, *Medical Hypotheses*, 2011; 77(6): 1054-157, hypothesise that statins and fibrates, both of which have anti-inflammatory and immunomodulatory effects and other multiple biologic activities, may exhibit synergistic effects when they were combined to neuraminidase inhibitors to treat the A (H5N1) virus infections via inhibiting the production of either the early inflammatory mediators (e.g., many cytokine/chemokine) or the late mediator (e.g., High Mobility Group Box Protein 1), even showing the antiviral activities with the prevention of the development of antiviral resistance.

As described by Bermejo-Martin J F, et al, Macrolides for the treatment of severe respiratory illness caused by novel H1N1 swine influenza viral strains, *J Infect Developing Countries*, 2009; 3(3): 159-161, macrolides are molecules with antibacterial activity that also have remarkably anti-inflammatory properties. They exert both stimulatory and inhibitory effects on leukocytes. These effects seem to be related to the activation state of the leukocytes, facilitating bacterial killing as well as resolving local inflammation. The use of macrolides in the treatment of severe disease caused by the novel H1N1 swine flu reassortment influenza viruses is proposed, particularly in combination with antivirals, in order to diminish the systemic inflammatory response leading to pneumonia and fatal outcome.

Sato K et al, Therapeutic Effect of Erythromycin on Influenza Virus-induced Lung Injury in Mice, *Am J Respir Crit Care Med*, 1998; 157: 853-857, evaluated the use of erythromycin (EM), an antibiotic with potent anti-inflammatory effects that is used for treating chronic lower respiratory tract infections, on influenza-virus-induced pneumonia in mice. It was found that the administration of EM at a dose of 3.3 mg/kg/d (intraperitoneally, from Days 1-6 after infection) significantly improved the survival rate of mice infected with influenza virus, and the survival rate of the virus-infected mice at Day 20 of infection increased in a dose-dependent fashion with EM administered to the animals, from 14% among controls to 42% among animals given EM at 1.0 mg/kg/d and 57% amongst those given EM at 3.3 mg/kg/d.

Börgeling et al., (Inhibition of p38 mitogen-activated protein kinase impairs influenza virus-induced primary and secondary host gene responses and protects mice from lethal H5N1 infection, *J Biol Chem.* 2014 Jan. 3; 289(1):13-27), describe the use of SB 202190, a p38 MAPK inhibitor, to control interferon signalling in the very early stages of influenza infection, and the resulting suppression of excessive cytokine expression. SB 202190 is administered at the same time as exposure to virus. The effects of viral infection concomitant with administration of SB 202190 are analysed up to 2 days post-infection in influenza infected mice. The data are limited to the effects of SB 202190 on cytokine expression when administered at the onset of infection with influenza virus (i.e. concomitant with exposure to virus). The effects of first SB 202190 administration at time points following exposure to the virus are not investigated and the effects of SB 202190 once the critical point (or tipping point) has been reached and the cytokine response becomes exaggerated and excessive are certainly not considered.

At the time of the present invention there remains an unmet need for a treatment to attenuate hypercytokinemia, and in particular hypercytokinemia associated with severe influenza virus infection.

SUMMARY OF THE INVENTION

As described below, especially with reference to the Examples, the inventors have discovered that p38 MAP kinase is upregulated in a number of cellular signalling pathways that are very active in patients with severe influenza in comparison with patients with mild or moderate influenza. In particular, it has been found that p38 MAP kinase is involved in a number of different non-metabolic signalling pathways comprising more than three nodes, in which 100% of the nodes are upregulated in patients with severe influenza versus patients with mild influenza, and at least 75% of the nodes are upregulated in patients with severe influenza versus patients with H1N1 infection or moderate influenza.

The p38 MAP kinase is a node that is located high in a signalling cascade in a range of cell types (epithelial, endothelial and immune) which are all important in the pathology of severe influenza. Because of the rapid and progressive nature of severe influenza, targeting a protein high in a signalling cascade is required to attenuate inflammatory mediator production quickly and reduce disease progression.

However, while numerous other targetable nodes in 95 pathway routes were identified by the inventors as potential targets for the treatment of severe influenza, it was unexpectedly found that p38 MAP kinase inhibitors exhibit a dose-dependent knockdown effect on the release of cytokines, particularly IP10, from endothelial cells treated with a viral conditioned medium that simulates the action of inflammatory mediators produced from influenza-infected epithelial cells, while other promising potential targets do not show the same effect. In particular, as disclosed by Example 4 below, while p38 MAP kinase inhibitors exhibit dose-dependent inhibition of IP10 in endothelial cells, as well as inhibitory effects on the release of inflammatory mediators from immune cells that are comparable with corticosteroids and macrolides, the next most promising target, namely mitogen-activated protein kinase (MEK), is not effective in inhibiting IP10 release from endothelial cells and actually appears to increase levels of IP10 at higher drug concentrations.

In addition, because severe influenza virus infection is often characterised by hypercytokinemia, as explained herein, the Examples and data presented below support the hypothesis that the p38 MAPK pathway is involved in hypercytokinemia more generally, i.e. hypercytokinemia that is associated with conditions other than severe influenza virus infection.

According to one aspect of the present invention therefore there is provided a p38 MAPK inhibitor for use in the treatment or prevention of hypercytokinemia. The hypercytokinemia may be associated with one or more of the following: severe influenza virus infection; graft-versus-host disease (GVHD); acute respiratory distress syndrome (ARDS); sepsis; Ebola; smallpox; systemic inflammatory response syndrome (SIRS); bacterial infection; and cancer According to another aspect of the present invention there is provided a p38 MAPK inhibitor for use in the treatment or prevention of severe influenza in a human patient.

According to another aspect of the present invention there is provided a pharmaceutical composition comprising a p38 MAPK inhibitor for use in the treatment or prevention of hypercytokinemia and/or for use in the treatment or prevention of severe influenza in a human patient.

In a further aspect of the present invention there is provided a method of treating or preventing hypercytokinemia and/or severe influenza in a subject (e.g. a human patient or an animal) in need thereof comprising administering to the subject (e.g. a human patient or an animal) a pharmaceutically effective amount of a p38 MAPK inhibitor. The hypercytokinemia may be associated with one or more of the following: severe influenza virus infection; graft-versus-host disease (GVHD); acute respiratory distress syndrome (ARDS); sepsis; Ebola; smallpox; systemic inflammatory response syndrome (SIRS); bacterial infection; and cancer In particular, the p38 MAPK inhibitor has an anti-inflammatory and/or an immunomodulatory effect.

In particular, the p38 MAPK inhibitor may be used for the treatment or prevention of hypercytokinemia and/or severe influenza in a human patient by inhibiting the release of pro-inflammatory mediators from endothelial cells and/or immune cells and/or epithelial cells (for example endothelial cells and/or immune cells). Suitably, the p38 MAP kinase inhibitor may be administered in an amount effective for inhibiting the release of pro-inflammatory mediators from endothelial cells and/or immune cells and/or epithelial cells (for example endothelial cells and/or immune cells)

More specifically, the p38 MAPK inhibitor may be used for the treatment or prevention of hypercytokinemia and/or severe influenza in a human patient by inhibiting the release of pro-inflammatory cytokines from endothelial cells and/or immune cells and/or epithelial cells (for example endothelial cells and/or immune cells). Suitably, the p38 MAP kinase inhibitor may be administered in an amount effective for inhibiting the release of pro-inflammatory cytokines from endothelial cells and/or immune cells and/or epithelial cells (for example endothelial cells and/or immune cells).

The p38 MAPK inhibitor may inhibit the release of one or more of, or all of: IL1-β, IL-6, IL-8, IL-10, IP10, TNFα, RANTES and/or MIP-1a (for example one or more of, or all of: IL1-β, IL-6, IL-8, IL-10, IP10, TNFα and/or RANTES) from endothelial cells and/or immune cells. In particular, the p38 MAPK inhibitor may inhibit the release of IL-10.

Suitably, the p38 MAP kinase inhibitor may be administered in an amount effective for inhibiting the release of one or more of, or all of: IL1-β, IL-6, IL-8, IL-10, IP10, TNFα, RANTES and/or MIP-1a from endothelial cells and/or immune cells (for example one or more of, or all of: IL1-β, IL-6, IL-8, IL-10, IP10, TNFα and/or RANTES from endothelial cells and/or immune cells). In particular, the p38 MAP kinase inhibitor may be administered in an amount effective for inhibiting the release of IL-10 from endothelial cells and/or immune cells.

In some embodiments, the p38 MAPK inhibitor may be used, in accordance with the present invention, for the treatment or prevention of hypercytokinemia and/or severe influenza in a human patient by inhibiting the release of IP10 from endothelial cells and/or immune cells.

Advantageously, the p38 MAPK inhibitor may exhibit dose-dependent inhibition of cytokine release from endothelial cells and/or immune cells.

As well as its inhibitory effects on cytokine release from endothelial cells, the p38 MAPK inhibitor may also act to inhibit the release of pro-inflammatory cytokines from immune cells, which are typically located close to endothelial cells in the lower respiratory tract. Suitably, the p38 MAP kinase inhibitor may be administered in an amount effective for inhibiting cytokine release from endothelial cells. In particular, the p38 MAP kinase inhibitor may be administered in an amount effective for inhibiting cytokine release from endothelial cells and inhibiting pro-inflammatory cytokines release from immune cells.

Suitably, the p38 MAPK inhibitor is of Formula I below or a pharmaceutically acceptable salt or solvate thereof:

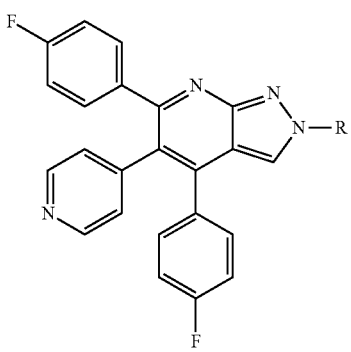

Formula I wherein R is $C_{1-3}$alkyl, which is optionally substituted by one or more of halo, $NR^1R^2$ or hydroxy, and $R^1$ and $R^2$ are independently H, halo or $C_{1-3}$alkyl, which is optionally substituted by one or more F.

For example, R may be optionally substituted by one, two or three of halo, $NR^1R^2$ or hydroxyl; or may be optionally substituted by one or two of halo, $NR^1R^2$ or hydroxyl; or may be optionally substituted by one of halo, $NR^1R^2$ or hydroxyl. When R is optionally substituted by more than one (for example two or three) halo, $NR^1R^2$ and/or hydroxyl, those substituents may be independently selected from that list.

When $R^1$ and/or $R^2$ is a $C_{1-3}$alkyl optionally substituted by one or more F, each $C_{1-3}$alkyl may, for example, be optionally substituted by one, two, or three F; be optionally substituted by one or two F; be optionally substituted by one or three F; be optionally substituted by one F; or be optionally substituted by three F.

In some embodiments, R is methyl or ethyl. In another embodiment, R may be propyl.

R may be substituted by one or more fluoride atoms.

In some embodiments, R may be substituted by hydroxy. For example, R may be ω-substituted alkyl, i.e. ω-hydroxyalkyl. Thus, in one embodiment, R may be 3-propanol.

Suitably $R^1$ and $R^2$ may be independently selected from H and $CH_3$.

In some embodiments, R may be $C_{1-3}$alkyl, which is substituted by one or more of halo, $NR^1R^2$ or hydroxy, and $R^1$ and $R^2$ are independently H, halo or $C_{1-3}$alkyl, which is optionally substituted by one or more F. For example, R may be $C_{1-3}$alkyl, which is substituted by one, two or three of halo, $NR^1R^2$ or hydroxy, and $R^1$ and $R^2$ are independently H, halo or $C_{1-3}$alkyl, which is optionally substituted by one, two or three F.

In some embodiments, the p38 MAPK inhibitor may be of Formula II or a pharmaceutically acceptable salt or solvate thereof:

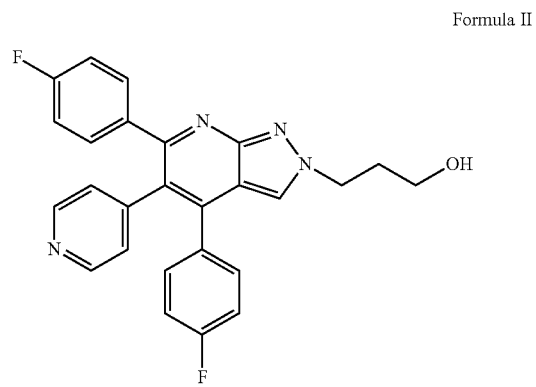 [SMILES: OCCCn1cc2c(-c3ccc(F)cc3)c(-c3ccncc3)c(-c3ccc(F)cc3)nc2n1]

Formula II

Alternatively, the p38 MAPK inhibitor may be of Formula III below or a pharmaceutically acceptable salt or solvate thereof:

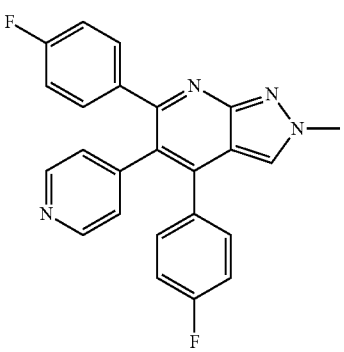

Formula III

The compounds of Formula II and III of the present invention, and the synthesis of those compounds, is disclosed in WO 2004/076450 A1 (see Examples 18 and 8, respectively). The contents of WO 2004/076450 A1 are hereby incorporated by reference.

In some embodiments, the p38 MAPK inhibitor may be of Formula I, or a pharmaceutically acceptable salt or solvate thereof, as defined above, with the proviso the compound is not a compound of Formula III, i.e. not a compound having the following structure:

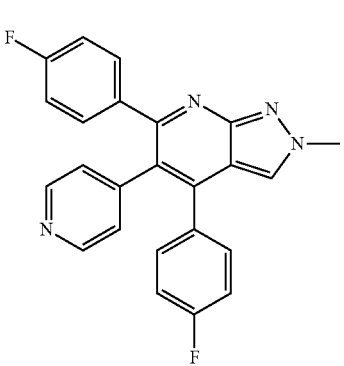

Formula III

By "severe influenza" herein is meant an illness caused by any influenza virus and leading to lower respiratory tract clinical disease and/or lower respiratory tract inflammation and/or hypercytokinemia (e.g. lung or systemic). As described above, severe influenza is distinct from uncomplicated (mild or moderate) influenza in which the patient typically has clinically tolerable upper and lower respiratory tract symptoms such, for example, as nasal congestion, sneezing, rhinorrhoea, pyrexia (fever) and cough and sputum production, and from which a patient normally recovers naturally without the need for therapeutic intervention. In severe influenza, the patient's inflammatory response to the viral infection is grossly exaggerated or extended, and the patient develops more severe respiratory tract symptoms or clinical complications that may require hospitalization and sometimes result in death. In such cases, early therapeutic intervention is critically important. As indicated by the WHO definition of severe influenza, a wide range of complications can be caused by influenza virus infection of the upper respiratory tract (nasal passages, sinuses, throat) and lower respiratory tract (lungs). Different patients with severe influenza may therefore present with a wide range of different symptoms or signs of the disease. The various symptoms or signs discussed below that are characteristic of severe influenza may be observable or detectable after 2 days of illness; typically, within 2-9 days of illness.

For instance, the severe influenza may be characterised by hypercytokinemia. Typically, the hypercytokinemia may involve elevated levels of one or more cytokines.

In some embodiments, the cytokines may comprise one or more of IL-8, IL-7, IL-6, Eotaxin, IP10, MCP1, MCP4, VEGF and MIP-1a (for example one or more of IL-8, IL-7, IL-6, Eotaxin, IP10, MCP1, MCP4 and VEGF). In particular, in some embodiments, the cytokines may comprise one or more of IL-8, Eotaxin, IP10, IL-7 and MIP-1a (for example one or more of IL-8, Eotaxin, IP10 and IL-7).

In some embodiments, the cytokines may comprise one or more of IL-6, IL-8 and IP10 (see Lee N. et al., 2011; Lee N. et al., Viral clearance and inflammatory response patterns in adults hospitalised for pandemic 2009 influenza A (H1N1) virus pneumonia, *Antiviral Therapy*, 2011; 16: 237-47).

In some embodiments, the hypercytokinemia may involve an elevated level of IL-6 of greater than about 1.5 or 2 times its plasma reference range (<3.1 pg/ml)—in some embodiments greater than about 10, 15 or 30 times, up to about 54 times or more. Thus, the hypercytokinemia may involve an elevated level of IL-6 of greater than about 4.7 pg/ml. More particularly, the hypercytokinemia involve an elevated level of IL-6 of greater than about 4.7 pg/ml in the case of seasonal flu, and greater than about 7.8 pg/ml in the case of pandemic flu.

In some embodiments, the hypercytokinemia may involve an elevated level of IL-8 of greater than about 1 or 2 times its plasma reference range (<5.0 pg/ml)—in some embodiments greater than about 4 times, up to about 8, 10 or 12 times or more. Thus, the hypercytokinemia may involve an elevated level of IL-8 greater than about 5.0 pg/ml. More particularly, the hypercytokinemia may involve an elevated level of IL-8 of greater than about 5.0 pg/ml in the case of seasonal flu, and greater than about 11.6 pg/mL in the case of pandemic flu.

In some embodiments, the hypercytokinemia may involve an elevated level of IP-10 of greater than about 1 or 2 times its plasma reference range (202-1480 pg/ml)—in some embodiments greater than about 1.1 times, greater than 1.5 times or greater than about 2, 3, 4, 5, 6, 7 or 8 times, up to about 10, 20 or 30 times or more. Thus, the hypercytokinemia may involve an elevated level of IP-10 of greater than about 835 pg/ml. More particularly, the hypercytokinemia may involve an elevated level of IP-10 of greater than about 835 pg/ml in the case of pandemic flu, and greater than about 1476 pg/ml in the case of seasonal flu.

In some embodiments, the hypercytokinemia may involve an elevated level of MCP-1 of greater than about 1 or 2 times its plasma reference range (<10.0-57.0 pg/ml)—in some embodiments greater than about 4 times, up to about 5.5 times or more. Thus, the hypercytokinemia may involve an elevated level of MCP-1 of greater than about 52.9 pg/ml. More particularly, the hypercytokinemia may involve an elevated level of MCP-1 of greater than about 52.9 pg/ml in the case of pandemic flu, and greater than about 64.8 pg/ml in the case of seasonal flu.

In some embodiments, the hypercytokinemia may involve an elevated level of sTNFR-1 of greater than about 1 or 2 times its plasma reference range (484-1407 pg/ml), up to about 2.5 times or more. Thus, the hypercytokinemia may involve an elevated level of sTNFR-1 of greater than about 1099.4 pg/ml. More particularly, the hypercytokinemia may involve an elevated level of sTNFR-1 of greater than about 1099.4 pg/ml in the case of seasonal flu, and greater than about 1250.7 pg/ml in the case of pandemic flu.

In some embodiments, the hypercytokinemia may involve an elevated level of MIG of greater than about 1 or than 2 times its plasma reference range (48.0-482.0 pg/ml)—in some embodiments greater than 1.1 times, greater than 1.5 times or greater than 2 times, up to about 15, 40 or 50 times or more. Thus, the hypercytokinemia may involve an elevated level of MIG of greater than about 103.8 pg/ml. More particularly, the hypercytokinemia may involve an elevated level of MIG of greater than about 103.8 pg/ml in the case of seasonal flu, and greater than about 118.7 pg/ml in the case of pandemic flu.

In some embodiments, the hypercytokinemia may involve an elevated level of IL-17A of greater than about 1, 1.5 or 2 times its plasma reference range (<10.0 pg/ml)—in some embodiments greater than 4 times, greater than 5 times or greater than 6 times, up to about 7 times or more. Thus, the hypercytokinemia may involve an elevated level of IL-17A of greater than about 5.0 pg/ml. More particularly, the hypercytokinemia may involve an elevated level of IL-17A of greater than about 5.0 pg/ml in the case of pandemic flu and greater than about 9.3 pg/ml in the case of seasonal flu.

The severe influenza may be characterised in some embodiments by sustained activation of the pro-inflammatory cytokines (IL-6, IL-8, IP 10, MCP-1, sTNFR-1 and/or MIP-1a; for example IL-6, IL-8, IP10, MCP-1 and/or sTNFR-1). The present invention provides a p38 MAPK inhibitor for use as disclosed herein (for example for use in the treatment or prevention of hypercytokinemia (e.g. hypercytokinemia associated with severe influenza virus infection) and/or for use in the treatment or prevention of severe influenza), wherein the p38 MAPK inhibitor inhibits the release of pro-inflammatory cytokines from endothelial cells and/or immune cells and/or epithelial cells; for example from endothelial cells and immune cells; or from endothelial cells, immune cells and epithelial cells. The p38 MAPK inhibitor may be administered in combination with a further agent. In particular, the present invention also provides a p38 MAPK inhibitor administered in combination with an antimicrobial agent (such as an antiviral agent), or an anticancer agent, and preferably with an antimicrobial agent (such as an antiviral agent), wherein the p38 MAPK inhibitor inhibits the release of pro-inflammatory cytokines from endothelial cells and/or immune cells and/or epithelial cells; for example from endothelial cells and immune cells; or from endothelial cells, immune cells and epithelial cells.

The present invention also provides a method of treating or preventing hypercytokinemia and/or severe influenza in a subject (e.g. a human patient or an animal) in need thereof as described herein (for example a method of treating or preventing hypercytokinemia (e.g. hypercytokinemia associated with severe influenza virus infection) and/or a method of treating or preventing severe influenza) wherein the p38 MAPK inhibitor inhibits the release of pro-inflammatory cytokines from endothelial cells and/or immune cells and/or epithelial cells; for example from endothelial cells and immune cells; or from endothelial cells, immune cells and epithelial cells. The p38 MAPK inhibitor may be administered in combination with a further agent. In particular, the present invention also provides a method of treating or preventing hypercytokinemia and/or severe influenza in a subject (e.g. a human patient or an animal) in need thereof as described herein, wherein the p38 MAPK inhibitor is administered in combination with an antimicrobial agent (such as an antiviral agent, or an anticancer agent, and preferably with an antimicrobial agent, such as an antiviral agent), and wherein the p38 MAPK inhibitor inhibits the release of pro-inflammatory cytokines from endothelial cells and/or immune cells and/or epithelial cells; for example from endothelial cells and immune cells; or from endothelial cells, immune cells and epithelial cells.

Levels of cytokines may be detected in the patient's whole blood, serum, plasma, nasal lavage, nasal secretions or bronchiolar alveolar lavage. Levels of cytokines may be quantified using any suitable technique known to those skilled in the art. Suitably, an enzyme-linked immunosorbent assay (ELISA) or fluorescent automated cell sorting (FACs) may be used. By way of example, a chemiluminescent immunoassay system such, for example, as that which is available from Meso Scale Diagnostics LLC (http://web.archive.org/web/20160522190937/https://www.mesoscale.com/) may be employed for its speed and sensitivity.

Further or alternatively, the severe influenza may be accompanied by significantly higher total white blood cell counts. A patient with severe influenza may have significantly higher absolute neutrophil counts than a patient with mild or moderate influenza. Typically, a patient with severe influenza after 2-9 days of illness may have a neutrophil count in the range $2.1-24.5 \times 10^3/\mu l$ (as compared with a patient with moderate influenza after 1-9 days of illness who may have a neutrophil count in the range $0.62-10.88 \times 10^3/\mu l$ or a patient with mild influenza after 3-8 days of illness who may have a neutrophil count in the range $0.5-6.5 \times 10^3/\mu l$). In some embodiments, the absolute platelet count may be significantly lower in patients with severe disease after 2-9 days of illness, e.g. $27-250 \times 10^3/\mu l$ (as compared with a patient with moderate influenza after 1-9 days of illness who may have a platelet count in the range $55-345 \times 10^3/\mu l$ or a patient with mild influenza after 3-8 days of illness who may have a platelet count in the range $79-370 \times 10^3/\mu l$) (Hoang et al, 2014).

Further, or alternatively, the severe influenza may be characterised by symptoms or signs of hypoxemia or cardiopulmonary insufficiency. In some embodiments, the patient may have an arterial oxygen saturation of ≤92% on room air by a transcutaneous method. Typically, the symptoms or signs of hypoxemia or cardiopulmonary insufficiency may include one or more of dyspnoea, tachypnoea, cyanosis, low blood pressure (designated as below normal range for age and sex) and tachycardia.

In some embodiments, the patient may have tachypnoea (respiratory rate≥30 for ages≥12 years, rate≥40 for ages 6 to 12 years, rate≥45 for ages 3 to 6 years, rate≥50 for ages 1 to 3 years).

In some embodiments, the patient may have or show signs of discomfort with breathing or dyspnoea (unable to speak full sentences, appear breathless, using accessory respiratory muscles).

Further, or alternatively, the severe influenza may be characterised by comorbidity with a lower respiratory disorder with or without radiological pulmonary infiltrates.

Further, or alternatively, the severe influenza may be characterised by symptoms or signs suggesting CNS and/or peripheral neuromuscular disorders such as, for example, encephalitis, myelitis or rhabdomyolysis, including altered mental state, unconsciousness, drowsiness, difficult to awaken, recurring convulsions, confusion, muscle pain, severe weakness, paralysis and sensory abnormalities (e.g. tingling in limbs, loss of normal pain sensation).

Still further, or alternatively, the severe influenza may be characterised by severe dehydration. The WHO defines severe dehydration in adults as >9% body weight loss (in children>15%) (K. Sinha and M. Davenport (eds.), Handbook of Pediatric Surgery, doi: 10.1007/978-1-84882-132-3_2.1, Springer-Verlag London Limited 2010). According to the present invention, the severe influenza may involve >9%, for example 10-15%, loss of body fluids.

Further, or alternatively, the severe influenza may be characterised by abnormal levels of fatigue and/or lethargy.

Further, or alternatively, the severe influenza may be characterised by the presence of radiological pulmonary infiltrate.

Still further, or alternatively, the severe influenza involves evidence of sustained viral infection or replication. In some embodiments, the patient may exhibit more than 2 days of constant or increasing viral replication that can be assayed using standard laboratory methods or diagnosed by the identification of persistent or worsening symptoms. In some embodiments, the patient may exhibit 3, 4, 5 or more days of constant or increasing viral replication. Thus, in some embodiments, the severe influenza in accordance with the present invention may be characterized by symptoms that persist or recur for more than 2, 3, 4, 5 or more days without signs of resolution. The symptoms that persist or recur may include fever (i.e. a temperature greater than 100° F./38° C.), lethargy, achiness, congestion, cough, sinus congestion, sinus drainage or upper respiratory congestion or inflammation.

Further, or alternatively, the severe influenza may be characterised by a secondary bacterial infection.

Further, or alternatively, the severe influenza may be characterised by a lower respiratory tract disorder or inflammation.

Further, or alternatively, the severe influenza may be characterised by mono- or multi-organ failure (e.g. respiratory failure or renal failure) or septic shock.

In some embodiments, the patient may be an infant (i.e. less than one year old) or elderly (i.e. 65 years old or more) or may be a pregnant woman.

In some embodiments, the human patient may have one or more underlying comorbidities that predispose the patient to severe influenza. For example, the patient may be immunocompromised, or may suffer from COPD, severe genetic anaemia, asthma or diabetes, chronic hepatic or renal insufficiency, obesity or a cardiovascular disorder or condition.

Thus, in some embodiments, the p38 MAPK inhibitor may be administered to the patient prophylactically, especially where the patient is in a "high-risk" or "at-risk" group as mentioned in the preceding paragraphs.

The p38 MAPK inhibitor may be administered to the patient after hypercytokinemia has developed, for example after the patient has been admitted to hospital. The p38 MAPK inhibitor may be administered after the critical point (threshold or tipping point) where the normal inflammatory response becomes an abnormal response. The p38 MAPK inhibitor may be administered to prevent hypercytokinemia developing, i.e. before the critical point is reached. This critical point is characterised by a threshold level of cytokines. The threshold level of cytokines will be, in part, dependent on the patient. The p38 MAPK inhibitor may be first administered at least 8 hours after an immune response is triggered e.g. 8, 9, 10, 11, 12, 13, 14, 15, 16, 17, 18, 19, 20, 21, 24, 25, 26, 27, 28, 29, 30, 31, 32, 33, 34, 35, 36, 37, 38, 39, 40, 41, 42, 43, 44, 45, 46, or 47 hours after an immune response is triggered: The p38 MAPK inhibitor may be first administered to the patient at least 48 hours after an immune response is triggered, at least 60 hours, at least 72 hours, at least 84 hours, at least 96 hours, at least 108 hours, at least 120 hours, at least 132 hours, at least 144 hours, at least 156 hours, at least 168 hours, at least 180 hours, at least 192 hours, at least 204 hours at least 216 hours, at least 228 hours, at least 240 hours after an immune response is triggered. The p38 MAPK inhibitor may be administered on multiple occasions at multiple time points after an immune response is triggered. The immune response may be triggered for example by exposure to a pathogen, for example influenza virus infection leading to severe influenza virus infection, or the immune response may be triggered by cancer, or may be triggered by an autoimmune response.

The p38 MAPK inhibitor may be administered at a dose between about 10 mg and about 1000 mg, for example between 10 mg and 1000 mg or between 10 mg and 400 mg. Up to 1000 mg may be administered per day in single or multiple doses for between 1 and 10 days, e.g. for 2 days, 3 days, 4 days, 5 days, 6 days, 7 days, 8 days, 9 days or 10 days.

The present invention also provides a p38 MAPK inhibitor administered in combination with a further agent. In particular, the present invention also provides a p38 MAPK inhibitor administered in combination with an antimicrobial agent, such as an antiviral agent, or an anticancer agent, and preferably with an antimicrobial agent, such as an antiviral agent. Where the p38 MAPK inhibitor is administered in combination with a further agent (for example an antimicrobial agent, such as an antiviral agent, or an anticancer agent), the p38 MAPK inhibitor and the further agent may be administered simultaneously, or the p38 MAPK inhibitor and the further agent may be administered sequentially, or the p38 MAPK inhibitor and the further agent may be administered separately. In particular, the further agent may be administered prior to the p38 MAPK inhibitor.

Preferably, the p38 MAPK inhibitor and the further agent (for example an antimicrobial agent, such as an antiviral agent, or an anticancer agent) may be administered simultaneously, for example in a single dosage form for simultaneous administration, e.g. for simultaneous oral administration. A single dosage form may also be referred to as a 'unit dose' or 'unit dosage form'. A single dosage form comprising a p38 MAPK inhibitor and a further agent comprises a mixture of the p38 MAPK inhibitor and the further agent, and optionally also inactive components such as pharmaceutically acceptable excipients. The single dosage form for simultaneous oral administration may, for example, be a tablet, powder or capsule.

The present invention also provides a p38 MAPK inhibitor for use as described herein (for example for use in the treatment or prevention of hypercytokinemia (e.g. hypercytokinemia associated with severe influenza virus infection) and/or for use in the treatment or prevention of severe influenza), wherein the p38 MAPK inhibitor is administered systemically or non-systemically, and preferably systemically, and in particular orally.

The present invention also provides a pharmaceutical composition for use as described herein (for example for use in the treatment or prevention of hypercytokinemia (e.g. hypercytokinemia associated with severe influenza virus infection) and/or for use in the treatment or prevention of severe influenza), wherein the pharmaceutical composition is formulated for oral administration.

Embodiments of the invention providing a p38 MAPK inhibitor (for example a p38 MAPK inhibitor of formula I) administered in combination with an antiviral agent (for example a neuraminidase inhibitor antiviral agents (e.g. oseltamivir phosphate)) are especially preferred as embodiments of the invention because the inventors have surprisingly found that a p38 MAPK inhibitor does not interfere with the effect of an antiviral agent (for example a neuraminidase inhibitor antiviral agents (e.g. oseltamivir phosphate)), and an antiviral agent (for example a neuraminidase inhibitor antiviral agents (e.g. oseltamivir phosphate)) does not interfere with the effect of a p38 MAPK inhibitor.

In another aspect of the present invention there is provided a method of treatment as described herein (for example for a method of treatment or prevention of hypercytokinemia (e.g. hypercytokinemia associated with severe influenza virus infection) and/or a method of treatment or prevention of severe influenza) in a subject (e.g. a human patient or animal) which comprises administering a therapeutically effective amount of a p38 MAP kinase inhibitor to a subject in need thereof wherein the p38 MAPK inhibitor is administered systemically or non-systemically to the subject (e.g. a human patient or animal), and preferably systemically, and in particular orally.

DETAILED DESCRIPTION OF THE INVENTION p38 MAPK inhibitors are an established class of active agents (see e.g. Zarubin and Han, *Cell Research* (2005) 15, 11-18. doi:10.1038/sj.cr.7290257). A wide range of p38 MAPK inhibitors are available to those skilled in the art (see e.g. Lee, et al., Inhibition of p38 MAP kinase as a therapeutic strategy, *Immunopharmacol.*, 2000; 47(2-3): 185-201. doi:10.1016/S0162-3109(00)00206-X, which is incorporated herein by reference). Examples of p38 MAPK inhibitors include VX-745, VX-702, RO-4402257, SCIO-469, BIRB-746, SD-0006, PH-787804, AMG-548, SB-681323 (Dilmapimod), LY2228820, GW-856553, RWJ67657 and BCT-197 (Xing, L., MAP Kinase 2015, Vol. 4:5508, which is incorporated herein by reference). These are examples of p38 MAPK inhibitors that have reached human trials.

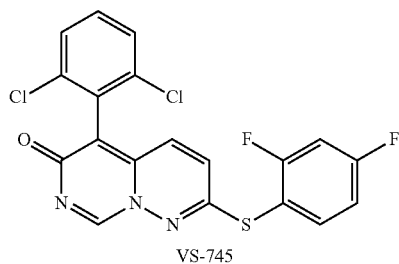
VS-745
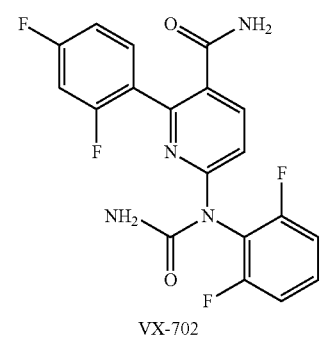
VX-702
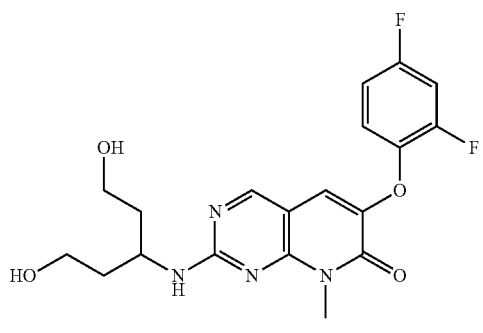
RO-4402257
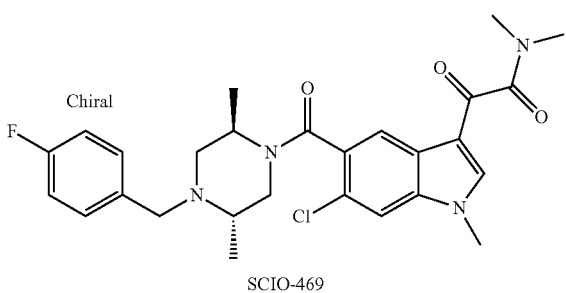
SCIO-469
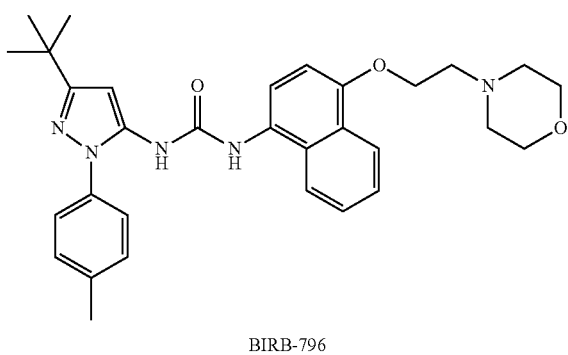
BIRB-796
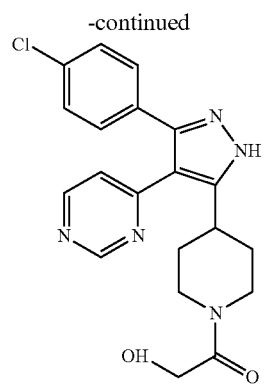
SD-0006
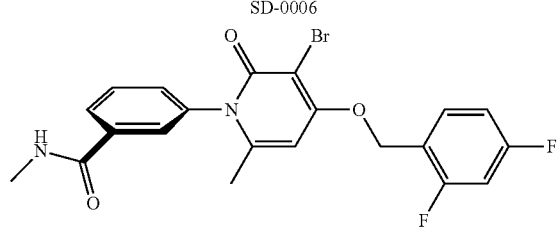
PH-797804
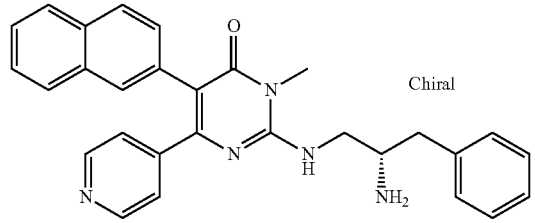
AMG-548
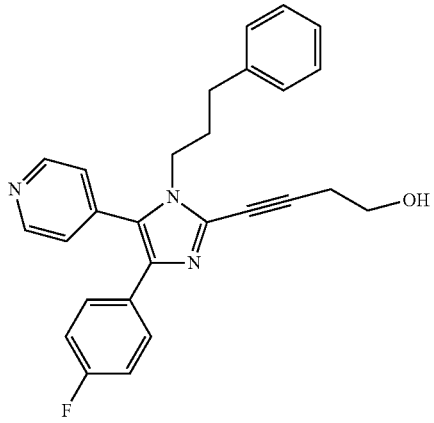
RWJ67657
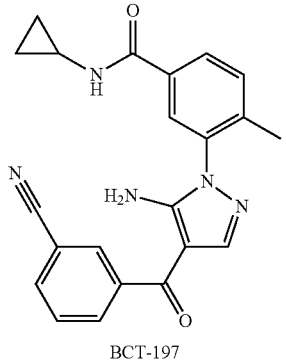
BCT-197

-continued

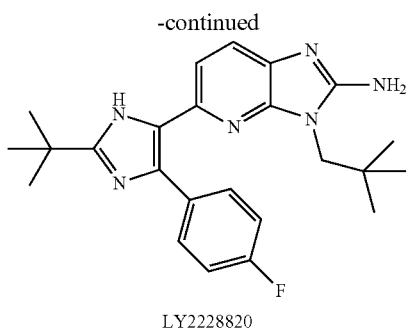

LY2228820

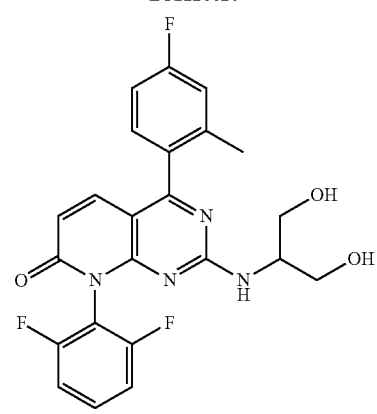

SB-681323

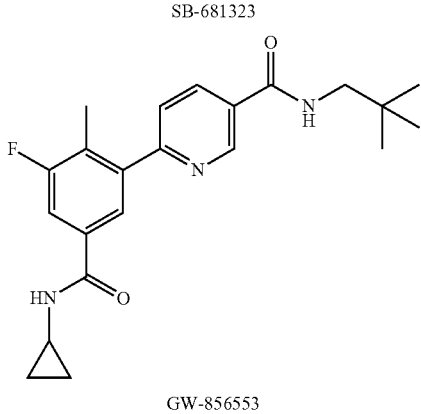

GW-856553

A preferred p38 MAPK inhibitor of the present invention is represented by Formula I, or a pharmaceutically salt or solvate thereof:

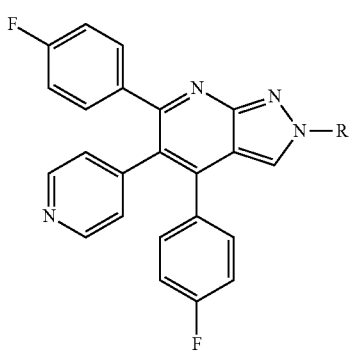

Formula I wherein R is as defined above.

The p38 MAPK inhibitor of Formula I may have Formula II, or a pharmaceutically acceptable salt or solvate thereof:

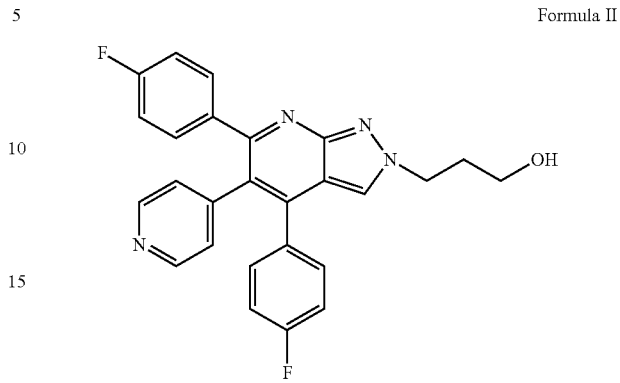

Formula II

The p38 MAPK inhibitor of Formula I may have Formula III or a pharmaceutically acceptable salt or solvate thereof:

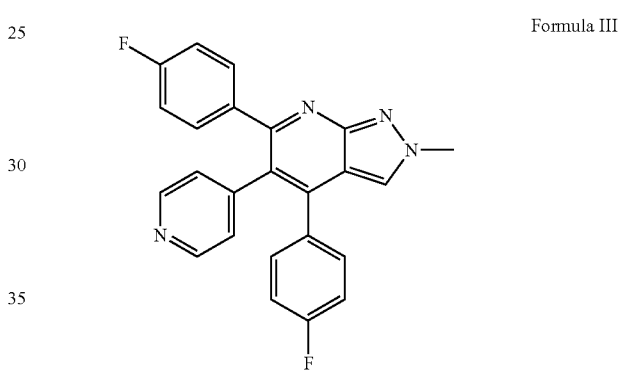

Formula III

The p38 MAPK inhibitors of Formulae I, II and III have a similar structure and are all thought to interact with the P38 MAPK active site to inhibit p38 MAPK mediated signalling. The inhibitors of Formulae I, II and III are thought specifically to inhibit p38α and p38β.

The compounds of Formula I may have particular advantages as p38 MAPK inhibitors, such as those described below. Certain compounds within the scope of Formula I may have particularly favourable pharmacokinetic properties (and in particular favourable pharmacokinetic properties making them especially suitable for oral administration), and/or favourable properties due to having a low side-effect profile and/or low toxicity. Such compounds include compounds of Formula I in which R is a substituted $C_{1-3}$alkyl group and/or in which R is a substituted or unsubstituted propyl moiety, for example the compound of Formula II in which R is propan-3-ol.

The use of a p38 MAPK inhibitor in accordance with the present invention aims to treat or prevent hypercytokinemia. As set out above hypercytokinemia is characterised by an exaggerated inflammatory response and there is a critical point (i.e. threshold or tipping point) where the normal response becomes an abnormal response and hypercytokinemia develops. This critical point is characterised by a threshold level of cytokines. The threshold level of cytokines will be, in part, dependent on the patient.

Hypercytokinemia may be associated with a number of infectious conditions and non-infectious conditions. In particular, hypercytokinemia may be associated with severe influenza virus infection; graft-versus-host disease (GVHD); acute respiratory distress syndrome (ARDS); sepsis; Ebola; smallpox; systemic inflammatory response syndrome (SIRS); bacterial infection; and cancer.

In particular, the use of a p38 MAPK inhibitor in accordance with the present invention aims to attenuate the inflammatory response in a patient with severe influenza, rather than ablate it, with the objective of blunting the damaging effects of the out-of-control inflammation, whilst preserving its protective and disease pro-resolution effects. Total ablation of inflammation would be likely to promote mortality in severe influenza, whereas attenuation of this explosive process should provide protection against the damaging effects caused by excess inflammatory responses whilst preserving the host's essential innate defence activities. The present invention therefore aims to "re-balance the system" rather than knock out components in their entirety.

p38 MAPK inhibitors that are especially useful at "re-balancing the system" by attenuating the inflammatory response in a patient with hypercytokinemia associated with severe influenza include the compounds of Formula I, and in particular the compounds of Formula I in which R is substituted $C_{1-3}$alkyl group and/or in which R is a substituted or unsubstituted propyl group, for example the compound of Formula II in which R is propan-3-ol. Such compounds may be very effective at attenuating the inflammatory response in a patient with severe influenza but do not ablate the immune response in its entirety; for example as shown by the results of Examples 6 and 8 in FIGS. 17, 18, 20 and 21, below.

Furthermore, from Example 6 and Example 8 below, the compound of Formula II exhibited consistently better effects than the compound of Formula III at attenuating the inflammatory response in endothelial and immune cells when simple (TNFa plus IL-6) and complex (HBEC or A459 viral soup) stimuli were applied to simulate the interaction of inflammatory mediators produced by influenza-infected epithelial cells on endothelial cells and immune cell. Thus, in certain embodiments, the compound of Formula I is preferably one in which R is a substituted $C_{1-3}$alkyl group and/or in which R is a substituted or unsubstituted propyl moiety, and more preferably the compound of Formula I is the compound of Formula II.

The p38 MAPK inhibitor may be administered in combination with an antimicrobial agent. The antimicrobial agent may be any one, or more, of the following: an antibacterial, an antibiotic, an antifungal, an antiviral, an antiparasitic, and/or an antimicrobial monoclonal antibody. An antimicrobial monoclonal antibody is any monoclonal antibody that is used to attempt to treat or prevent microbial disease.

In particular, the p38 MAPK inhibitor may be administered in combination with an antiviral agent. The antiviral agent may be any one, or more, of the following or pharmaceutically acceptable salts thereof: amantadine; rimantadine; ribavirin; idoxuridine; trifluridine; vidarabine; acyclovir; ganciclovir; foscarnet; zidovudine; didanosine; zalcitabine; stavudine;

famciclovir; valaciclovir; antitussives; mucolytics; expectorants; antipyretics; analgesics and/or nasal decongestants. Preferably the antiviral agent is a neuraminidase inhibitor such as: oseltamivir phosphate, zanamivir, peramivir and/or laninamivir. In a preferred aspect the p38 MAPK inhibitor is administered in combination with oseltamivir or a pharmaceutically acceptable salt thereof (e.g. oseltamivir phosphate). While not wishing to be bound by theory it is hypothesised that the oseltamivir phosphate combats the influenza infection (has an antiviral effect) while the p38 MAPK inhibitor has an immunomodulatory effect against hypercytokinemia.

It has been surprisingly found by the present inventors that p38 MAPK inhibitors and antiviral agents (such as neuraminidase inhibitor antiviral agents (e.g. oseltamivir phosphate)), and more especially p38 MAPK inhibitors of Formula I and neuraminidase inhibitor antiviral agents (e.g. oseltamivir phosphate), do not significantly interfere with each other's activity, i.e. antiviral agents do not negate the attenuating anti-inflammatory effects of p38 MAPK inhibitors; and the p38 MAPK inhibitors do not negate the antiviral effects of anti-viral agents. For example, the results of Example 9 in FIGS. 22 and 23 below show that when oseltamivir was combined with compounds of Formula II, $TCID_{50}$ was reduced to the level seen with oseltamivir on its own, indicating that p38MAPK inhibitor therapy may be used in combination with oseltamivir without materially impacting its antiviral activity (FIG. 22); and also that oseltamivir had no observed effect on the anti-inflammatory properties of the compound of Formula II (FIG. 23).

The non-interference between these agents is especially advantageous because, as described above, the anti-inflammatory properties of the p38 MAPK inhibitor compound may be used in accordance with the present invention to "re-balance the system" of inflammation in the body when used in the treatment of hypercytokinemia associated with severe influenza. Thus any increase or decrease in the anti-inflammatory properties of the p38 MAPK inhibitor could lead to a loss of the balancing effect of the p38 MAPK inhibitor compound, e.g. a decrease in the anti-inflammatory properties of the p38 MAPK inhibitor may not sufficiently blunt the damaging effects of the out-of-control inflammation, and an increase in the anti-inflammatory properties of the p38 MAPK inhibitor may ablate the necessary protective and disease pro-resolution effects of the body's inflammatory response. It is also advantageous that the p38 MAPK inhibitor compound does not adversely affect the anti-viral effects of the antiviral agent.

As such, in another embodiment, the present invention provides a p38 MAPK inhibitor for use in the present invention (for example for use in the treatment or prevention of hypercytokinemia (e.g. hypercytokinemia associated with severe influenza virus infection) and/or for use in the treatment or prevention of severe influenza), wherein the p38 MAPK inhibitor is administered to a patient who has been administered an antiviral agent for the treatment of severe flu. In such embodiments, the p38 MAPK inhibitor may be administered, for example, within 72 hours, 60 hours, 48 hours, 36 hours, 24 hours, 16 hours, 12 hours, 10 hours, 8 hours, 6 hours, 4 hours, 2 hours, or 1 hour of administration of the antiviral agent. The antiviral agent may be one as described above (e.g. oseltamivir phosphate).

In a further embodiment, the present invention provides a p38 MAPK inhibitor for use in the present invention (for example for use in the treatment or prevention of hypercytokinemia (e.g. hypercytokinemia associated with severe influenza virus infection) and/or for use in the treatment or prevention of severe influenza), wherein the p38 MAPK inhibitor is administered to a patient who is undergoing treatment of severe flu comprising administering an antiviral agent. In such embodiments, the patient may have undergone treatment of severe flu comprising administering an antiviral agent for at least 1 hour (for example 1 hours, 2 hours, 4 hours, 8 hours, 12 hours, 1 day, 2 days, 3 days, 4 days, 5 days, 6 days, 7 days, 9 days or 10 days), at least 2 hours (for example 2 hours, 4 hours, 8 hours, 12 hours, 1 day, 2 days, 3 days, 4 days, 5 days, 6 days, 7 days, 9 days or 10 days), at least 4 hours (for example 4 hours, 8 hours, 12 hours, 1 day, 2 days, 3 days, 4 days, 5 days, 6 days, 7 days, 9 days or 10 days), at least 8 hours (for example 8 hours, 12 hours, 1 day, 2 days, 3 days, 4 days, 5 days, 6 days, 7 days, 9 days or 10 days), at least 12 hours (for example 12 hours, 1 day, 2 days, 3 days, 4 days, 5 days, 6 days, 7 days, 9 days or 10 days), at least 1 day (1 day, 2 days, 3 days, 4 days, 5 days, 6 days, 7 days, 9 days or 10 days), at least 2 days (for example 2 days, 3 days, 4 days, 5 days, 6 days, 7 days, 9 days or 10 days), or 3 days (for example 3 days, 4 days, 5 days, 6 days, 7 days, 9 days or 10 days), before treatment with the p38 MAPK inhibitor. The antiviral agent may be one as described above (e.g. oseltamivir phosphate).

In another embodiment, the present invention provides a method of treating or preventing hypercytokinemia in a human patient as described herein (for example a method of treating or preventing hypercytokinemia (e.g. hypercytokinemia associated with severe influenza virus infection) and/or a method of treating or preventing severe influenza), wherein the p38 MAPK inhibitor is administered to a patient who has been administered an antiviral agent for the treatment of severe flu. In such embodiments, the p38 MAPK inhibitor may be administered, for example, within 72 hours, 60 hours, 48 hours, 36 hours, 24 hours, 16 hours, 12 hours, 10 hours, 8 hours, 6 hours, 4 hours, 2 hours, or 1 hour of administration of the antiviral agent. The antiviral agent may be one as described above (e.g. oseltamivir phosphate).

In embodiments where the antiviral agent is oseltamivir or a salt therefore, and in particular in embodiments where the antiviral agent is oseltamivir phosphate, the oseltamivir or a salt thereof (e.g. the oseltamivir phosphate) may be administered at a dose from about 1 mg and to 200 mg, for example between 5 mg and 100 mg (e.g. 5, 6, 7, 8, 9, 10, 12, 15, 20, 30, 45, 50, 75 or 100 mg), and preferably between 6 mg and 75 mg preferably 6, 12, 30, 45 or 75 mg). Single or multiple doses of the antiviral agent may be administered in a day, for example 1 dose per day, or 2 doses per day.

In embodiments where the antiviral agent is oseltamivir or a salt therefore, and in particular in embodiments where the antiviral agent is oseltamivir phosphate, the oseltamivir or a salt thereof (e.g. the oseltamivir phosphate) may be administered as a dose to achieve a blood plasma level of oseltamivir carboxylate of 1 to 750 µg/L, preferably 5 to 600 µg/L, preferably 10 to 500 µg/L, more preferably 25 to 500 µg/L, and more preferably 50 to 500 µg/L, for example 100 to 400 µg/L. Single or multiple doses of the antiviral agent may be administered in a day, for example 1 dose per day, or two doses per day, to achieve a blood plasma level of oseltamivir carboxylate as described above.

In a further embodiment, the present invention provides a method of treating or preventing hypercytokinemia in a human patient as described herein (for example a method of treating or preventing hypercytokinemia (e.g. hypercytokinemia associated with severe influenza virus infection) and/or a method of treating or preventing severe influenza), wherein the p38 MAPK inhibitor is administered to a patient who is undergoing treatment of severe flu comprising administering an antiviral agent. In such embodiments, the patient may have undergone treatment of severe flu comprising administering an antiviral agent for at least 1 hour (for example 1 hours, 2 hours, 4 hours, 8 hours, 12 hours, 1 day, 2 days, 3 days, 4 days, 5 days, 6 days, 7 days, 9 days or 10 days), at least 2 hours (for example 2 hours, 4 hours, 8 hours, 12 hours, 1 day, 2 days, 3 days, 4 days, 5 days, 6 days, 7 days, 9 days or 10 days), at least 4 hours (for example 4 hours, 8 hours, 12 hours, 1 day, 2 days, 3 days, 4 days, 5 days, 6 days, 7 days, 9 days or 10 days), at least 8 hours (for example 8 hours, 12 hours, 1 day, 2 days, 3 days, 4 days, 5 days, 6 days, 7 days, 9 days or 10 days), at least 12 hours (for example 12 hours, 1 day, 2 days, 3 days, 4 days, 5 days, 6 days, 7 days, 9 days or 10 days), at least 1 day (1 day, 2 days, 3 days, 4 days, 5 days, 6 days, 7 days, 9 days or 10 days), at least 2 days (for example 2 days, 3 days, 4 days, 5 days, 6 days, 7 days, 9 days or 10 days), or 3 days (for example 3 days, 4 days, 5 days, 6 days, 7 days, 9 days or 10 days), before treatment with the p38 MAPK inhibitor. The antiviral agent may be one as described above (e.g. oseltamivir phosphate).

The p38 MAPK inhibitor may be administered in combination with an anticancer agent. An anticancer agent is any agent that is used to attempt to treat or prevent cancer.

The p38 MAPK inhibitor may be administered systemically or non-systemically, such as orally, or topically, including epidermally, bucally, intranasally or via inhalation (aerosol), or both intranasally and via inhalation or parenterally (e.g. intravenously, subcutaneously) or in combination topically and parenterally.

As used herein "topically" includes non-systemic administration. This includes the application of a compound externally to the epidermis or the buccal cavity and/or the instillation of such a compound into the ear, eye and nose.

As used herein "systemic administration" refers to oral, intravenous, intraperitoneal and intramuscular administration, subcutaneous intranasal, intra-rectal or intravaginal.

In particular the p38 MAPK inhibitor may be administered intravenously. Preferably the p38 MAPK inhibitor is administered orally. Oral administration allows for a systemic rather than localized effect. This is advantageous as it may allow for all cell types associated with and/or affected by the hypercytokemia (in particular hypercytokemia associated with severe flu) to be treated with the p38 MAPK inhibitor (i.e. endothelial cells, epithelial cells and/or immune cells). In addition, oral formulations, for example tablets, are easy to take and so are associated with improved patient compliance. Oral administration is particularly advantageous when other routes of administration, such as inhalation, would be difficult, for example when a patient is suffering from lung complications.

It will be recognized by those skilled in the art that the optimal quantity and spacing of individual dosages of a p38 MAPK inhibitor will be determined by the nature and extent of the condition being treated, the form, route and site of administration, and the particular patient being treated, and that such optimums can be determined by conventional techniques. It will also be appreciated by one of skill in the art that the optimal course of treatment, i.e. the number of doses of a p38 MAPK inhibitor given per day for a defined number of days, can be ascertained by those skilled in the art using conventional course of treatment determination tests. However, in view of its key signalling role, targeting p38 MAP kinase may result in unwanted side effects. In order to minimise any such side effects, the p38 MAPK inhibitor may be administered to a patient in accordance with the present invention for a maximum period of 1-5 days, preferably 1-3 days. In some embodiments, the p38 MAPK inhibitor may be administered for just one or two days. Once-a-day treatment may also be preferred to minimise any deleterious side effects.

In yet another aspect of the present invention there is provided a pharmaceutical composition for use in the treatment or prevention of hypercytokinemia in a human patient, the composition comprising a p38 MAPK inhibitor having Formula I, Formula II and/or Formula III, pharmaceutically acceptable salts or solvates thereof.

In particular, there is provided a pharmaceutical composition for use in the treatment or prevention of severe influenza in a human patient, the composition comprising a p38 MAPK inhibitor having Formula I, Formula II and/or Formula III, and pharmaceutically acceptable salts or solvates thereof, optionally in combination with one or more pharmaceutically acceptable diluents or carriers. Diluents and carriers may include those suitable for parenteral, oral, topical, mucosal and rectal administration.

A pharmaceutical composition comprising a p38 MAPK inhibitor (for example a p38 MAPK inhibitor of Formula I, Formula II and/or Formula III, or pharmaceutically acceptable salts or solvates thereof), may further comprise, or be administered in combination with, a further agent. The further agent may be an antimicrobial agent, or anticancer agent. In particular, the further agent may be an antiviral agent and more specifically oseltamivir or a pharmaceutically acceptable salt thereof (e.g. oseltamivir phosphate).

As used herein, the term "pharmaceutically-acceptable salts or solvates" refers to salts or solvates that retain the desired biological activity of the subject compound and exhibit minimal undesired toxicological effects. These pharmaceutically-acceptable salts may be prepared in situ during the final isolation and purification of the compound, or by separately reacting the purified compound in its free acid or free base form with a suitable base or acid, respectively.

The compounds of the invention may exist in crystalline or non-crystalline (amorphous) form, or as a mixture thereof. For compounds of the invention that are in crystalline form, the skilled artisan will appreciate that pharmaceutically-acceptable solvates may be formed wherein solvent molecules are incorporated into the crystalline lattice during crystallization. Solvates may involve non-aqueous solvents such as ethanol, isopropanol, DMSO, acetic acid, ethanolamine, and ethyl acetate, or they may involve water as the solvent that is incorporated into the crystalline lattice. Solvates wherein water is the solvent that is incorporated into the crystalline lattice are typically referred to as "hydrates". Hydrates include stoichiometric hydrates as well as compositions containing viable amounts of water. The invention includes all such solvates.

Certain compounds of the invention that exist in crystalline form, including the various solvates thereof, may exhibit polymorphism (i.e. the capacity to occur in different crystalline structures). These different crystalline forms are typically known as "polymorphs". The invention includes all such polymorphs. Polymorphs have the same chemical composition but differ in packing, geometrical arrangement, and other descriptive properties of the crystalline solid state. Polymorphs, therefore, may have different physical properties such as shape, density, hardness, deformability, stability, and dissolution properties. Polymorphs typically exhibit different melting points, IR spectra, and X-ray powder diffraction patterns, which may be used for identification. Different polymorphs may be produced, for example, by changing or adjusting the reaction conditions or reagents, used in making the compound. For example, changes in temperature, pressure, or solvent may result in polymorphs. In addition, one polymorph may spontaneously convert to another polymorph under certain conditions.

The pharmaceutical composition of the invention may be prepared e.g. for parenteral, subcutaneous, intramuscular, intravenous, intra-articular or peri-articular administration, particularly in the form of liquid solutions or suspensions; for oral administration, particularly in the form of tablets or capsules; for topical e.g. pulmonary or intranasal administration, particularly in the form of powders, nasal drops or aerosols and transdermal administration; for mucosal administration e.g. to buccal, sublingual or vaginal mucosa, and for rectal administration e.g. in the form of a suppository.

The composition may conveniently be administered in unit dosage form and may be prepared by any of the methods well-known in the pharmaceutical art, for example as described in Remington's Pharmaceutical Sciences, 17th ed., Mack Publishing Company, Easton, Pa., (1985). A formulation for parenteral administration may contain as excipients sterile water or saline, alkylene glycols such as propylene glycol, polyalkylene glycols such as polyethylene glycol, oils of vegetable origin, hydrogenated naphthalenes and the like. A formulation for nasal administration may be solid and may contain excipients, for example, lactose or dextran, or may be aqueous or oily solutions for use in the form of nasal drops or metered spray. For buccal administration typical excipients include sugars, calcium stearate, magnesium stearate, pregelatinated starch, and the like.

In particular, the pharmaceutical composition may be formulated for oral administration. A composition suitable for oral administration may comprise one or more physiologically compatible carriers and/or excipients and may be in solid or liquid form. Tablets and capsules may be prepared with binding agents, for example, syrup, acacia, gelatin, sorbitol, tragacanth, or poly-vinylpyrollidone; fillers, such as lactose, sucrose, corn starch, calcium phosphate, sorbitol, or glycine; lubricants, such as magnesium stearate, talc, polyethylene glycol, or silica; and surfactants, such as sodium lauryl sulfate. A liquid composition may contain conventional additives such as suspending agents, for example sorbitol syrup, methyl cellulose, sugar syrup, gelatin, carboxymethyl-cellulose, or edible fats; emulsifying agents such as lecithin, or acacia; vegetable oils such as almond oil, coconut oil, cod liver oil, or peanut oil; preservatives such as butylated hydroxyanisole (BHA) and butylated hydroxytoluene (BHT). A liquid composition may be encapsulated in, for example, gelatin to provide a unit dosage form.

A solid oral dosage form may include tablets, two-piece hard shell capsules and soft elastic gelatin (SEG) capsules.

A dry shell formulation typically comprises of about 40% to 60% concentration of gelatin, about a 20% to 30% concentration of plasticizer (such as glycerin, sorbitol or propylene glycol) and about a 30% to 40% concentration of water. Other materials such as preservatives, dyes, opacifiers and flavours also may be present. The liquid fill material may comprise a solid drug that has been dissolved, solubilized or dispersed (with suspending agents such as beeswax, hydrogenated castor oil or polyethylene glycol 4000) or a liquid drug in vehicles or combinations of vehicles such as mineral oil, vegetable oils, triglycerides, glycols, polyols and surface-active agents.

In some embodiments, compositions of the invention may be administered topically to the lung. In some embodiments, therefore the composition of the invention may comprise a p38 MAPK inhibitor optionally in combination with one or more topically acceptable diluents or carriers. Topical administration to the lung may be achieved by use of an aerosol formulation. Aerosol formulations typically comprise the active ingredient suspended or dissolved in a suitable aerosol propellant, such as a chlorofluorocarbon (CFC) or a hydrofluorocarbon (HFC). Suitable CFC propellants include trichloromonofluoromethane, dichlorotetrafluoromethane, and dichlorodifluoromethane. Suitable HFC propellants include tetrafluoroethane (HFC-134a) and heptafluoropropane (HFC-227). The propellant typically comprises 40% to 99.5% e.g. 40% to 90% by weight of the total inhalation composition. The formulation may comprise excipients including co-solvents (e.g. ethanol) and surfactants (e.g. lecithin, sorbitan trioleate and the like). Aerosol formulations are packaged in canisters and a suitable dose is delivered by means of a metering valve (e.g. as supplied by Bespak, Valois or 3M).

Topical administration to the lung may also be achieved by use of a non-pressurised formulation such as an aqueous solution or suspension. This may be administered by means of a nebuliser. Topical administration to the lung may also be achieved by use of a pressured metered dose inhaler (pMDI) or a dry-powder formulation. A dry powder formulation will contain the p38 MAPK inhibitor in finely divided form, typically with a mass mean diameter (MMAD) of 1-10 microns. The formulation will typically contain a topically acceptable diluent such as lactose, usually of large particle size e.g. a mass mean diameter (MMAD) of 100 μm or more. Example dry powder delivery systems include SPINHALER, DISKHALER, TURBOHALER, DISKUS and CLICKHALER.

In yet another aspect of the present invention there is provided a method for treating or preventing hypercytokinemia in a human patient in need thereof comprising administering to the patient a therapeutically or prophylactically effective amount of a p38 MAPK inhibitor having Formula I, Formula II or Formula III or pharmaceutically acceptable salts or solvates thereof. In particular, there is a provided a method for treating or preventing severe influenza virus infection.

The method may include administering a p38 MAPK inhibitor in combination with a further agent. The further agent may be an antimicrobial agent, or anticancer agent. In particular, the further agent may be an antiviral agent and more specifically oseltamivir or a pharmaceutically acceptable salt thereof (e.g. oseltamivir phosphate). In particular, the p38 MAPK inhibitor may be administered orally.

It will be understood that the description of the present invention herein insofar as it relates to p38 MAP kinase inhibitors for use in the present invention (for example for use in the treatment or prevention of hypercytokinemia (e.g. hypercytokinemia associated with severe influenza virus infection) and/or for use in the treatment or prevention of severe influenza) is applicable equally to the various aspects of the invention set forth herein that pertain to methods of treatment of the invention in humans and animals (for example methods of treatment or prevention of hypercytokinemia (e.g. hypercytokinemia associated with severe influenza virus infection) in a subject (e.g. a human patient) in need thereof and/or methods of treatment or prevention of severe influenza in a subject (e.g. a human patient) in need thereof)).

BRIEF DESCRIPTION OF THE DRAWINGS

FIG. 1 illustrates the identification of signalling pathways.

FIG. 2 illustrates the mapping the activity of genes in IL-1, TNFα and IL-6 stimulated pathways. These cytokines are produced by influenza virus infected cells and found to be increased in the blood of people infected with influenza, particularly those hospitalised with severe influenza. The hatched lines indicate gene expression levels with lines sloping from top right to bottom left indicating upregulation (e.g. TNF-α), and lines sloping from top left to bottom right (e.g. LBP) indicating down-regulation; genes that are both upregulated and down-regulated are indicated by cross-hatching. The line spacing represents the intensity of up- or down-regulation, with more densely packed lines indicating greater activity. The maps were generated using IPA. A "route" through a pathway is defined as a single contiguous connection of proteins that extend from the plasma membrane through to the nucleus.

FIG. 3 shows an example of scoring a route through the IL-6 pathway of FIG. 2.

FIG. 4 shows three key cell types involved in the pathology of severe influenza.

FIG. 5 is a schematic of influenza 'soup' production and electrogenerated chemiluminescence analysis in human epithelial cells. Infected cell "soups" contain key cytokines found in clinical samples.

FIG. 6 shows Western blotting of phosphorylated P38 and HSP27 in response to viral soup application and effects of P38 inhibition in epithelial cells using the p38 MAPK inhibitor PH 797804. Electrogenerated chemiluminescence analysis of inflammatory cytokine production in response to viral soup application, and effects of P38 inhibition in epithelial cells.

FIG. 7 shows Western blotting of phosphorylated HSP27 in response to viral soup application and effects of P38 inhibition in endothelial cells. Electrogenerated chemiluminescence analysis of inflammatory cytokine production in response to viral soup application, and effects of P38 inhibition in endothelial cells.

FIG. 8 shows Western blotting of phosphorylated HSP27 in response to viral soup application and effects of P38 inhibition in immune cells. Electrogenerated chemiluminescence analysis of inflammatory cytokine production in response to viral soup application, and effects of P38 inhibition in immune cells. Cell viability of immune cells in response to increasing concentrations of P38 MAPK inhibitor.

FIG. 9 shows electrogenerated chemiluminescence analysis of inflammatory cytokine production in response to LPS, CD-3 and viral soup application. Effects of P38 inhibition on viral soup induced inflammatory cytokine in immune cells.

FIG. 10 shows the effects of p38 and MEK inhibitors on IP10 production by HUVECs stimulated with 70% HBEC viral soup. Secreted cytokine levels were assayed by electrogenerated chemiluminescence. Statistical significance was calculated using one-way ANOVA with Dunnett's multiple comparison post hoc test.

FIG. 11 shows compound effects on IL-1b production from immune cells. Each point on the dot plot represents an individual experiment. Statistical significance was calculated using one-way ANOVA with Dunnett's multiple comparison post hoc test.

FIG. 12. shows compound effects on TNFa production from immune cells. Each point on the dot plot represents an individual experiment. Statistical significance was calculated using one-way ANOVA with Dunnett's multiple comparison post hoc test.

FIG. 13 shows compound effects on IP10 production from endothelial cells. Each point on the dot plot represents an individual experiment. Statistical significance was calculated using one-way ANOVA with Dunnett's multiple comparison post hoc test.

FIG. 14 shows compound effects on IL8 production from endothelial cells. Each point on the dot plot represents an individual experiment. Statistical significance was calculated using one-way ANOVA with Dunnett's multiple comparison post hoc test.

FIG. 15 shows the cytokine levels in 28 healthy volunteers infected with influenza virus (samples collected at Day −1 to Day 28, hollow dots) and 30 individuals hospitalised with severe influenza (stippled dots). Blood samples from the severe patients were collected between 24 and 72 hours after admission to hospital. The statistical significance of differences in cytokine levels between the infected healthy volunteers (D2 and D3) and the hospitalised patients (influenza A or B) was calculated using the Mann-Whitney U test.

EXAMPLES

Example 1

Figure 1:
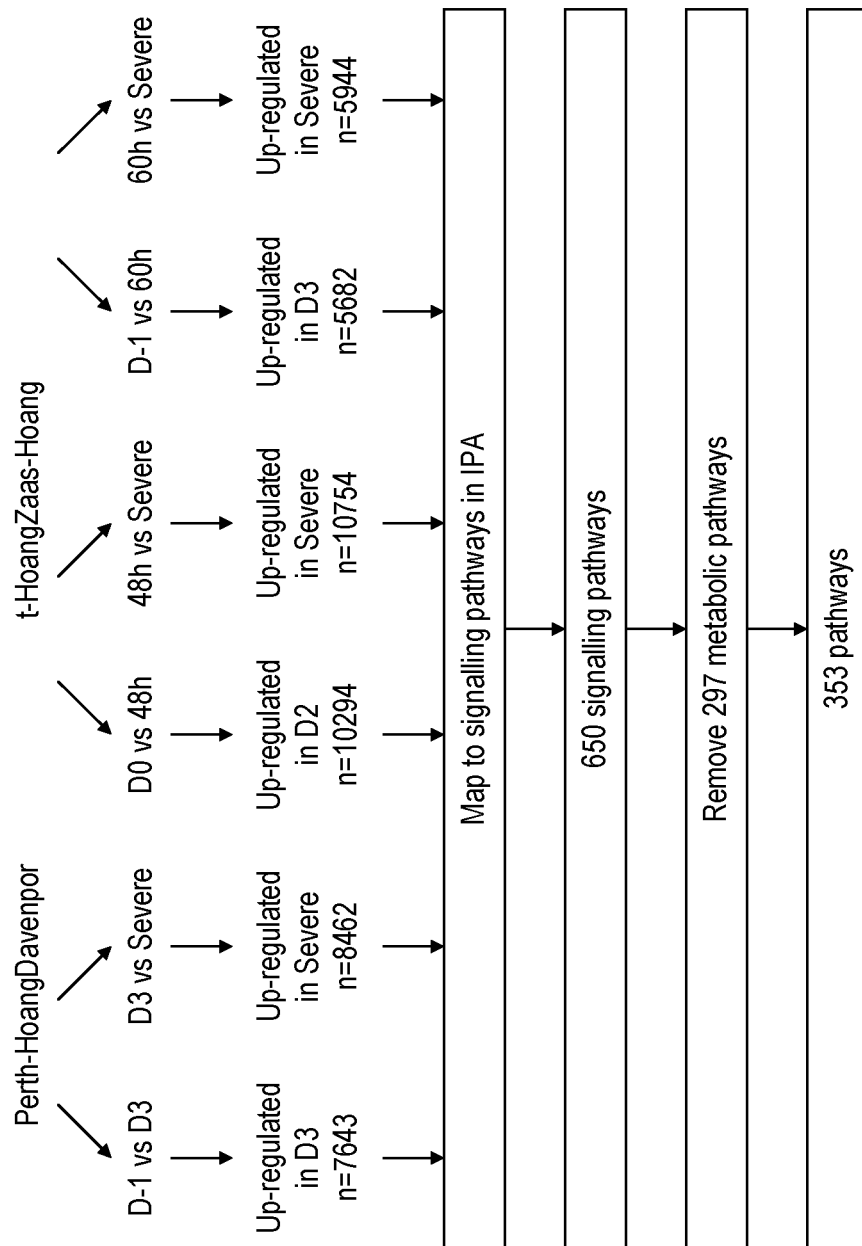

Identification of p38 MAPK by Transcriptomic Analysis

Bioinformatics analysis of transcriptomic data from blood samples collected from human volunteers and patients infected with influenza was used to map the signalling pathways activated in the human host response to influenza infection in both uncomplicated (mild and moderate) and severe influenza (see PHE Guidance on Use of Anti-Viral Agents for the Treatment and Prophylaxis of Seasonal Influenza (2015-16), version 6.0, September 2015). Human viral challenge studies were carried out and transcriptomic data from those studies were used for mapping the former, while transcriptomic data from a field-based sampling study (Hoang, L. T. et al., 2014) were used for mapping the latter. Comparison of signalling pathways identified by comparing both datasets enabled the identification of signalling pathways that are very active in severe influenza versus mild and moderate influenza. Further analysis of individual pathway components identified p38 MAPK as a key "node" in a number of these active pathways.

Healthy human volunteers were intranasally challenged with influenza A/Wisconsin/67/2005 (H3N2) (Zaas, A. K. et al., Gene expression signatures diagnose influenza and other symptomatic respiratory viral infection in humans, Cell Host Microbe, 2009; 17: 207-217 and Davenport, E. E. et al., Transcriptomic profiling facilitates classification of response to influenza challenge, J. Mol. Med., 2015; 93: 105-114) or with influenza A/Perth/16/2009 (H3N2) (internal study, not published). PAXgene™ samples of whole blood were collected from the volunteers at various time points for subsequent transcriptome analysis. Methods for influenza A/Wisconsin/67/2005 (H3N2) viral challenge, case definitions, sample collection, RNA purification and microarray analysis are as detailed in Zaas et al., 2009 and Davenport et al., 2015. Methods for influenza A/Perth/16/2009 (H3N2) viral challenge, case definitions and sample collection were as described for the Wisconsin strain except RNA purification and microarray analysis using Affymetrix HGU133 Plus 2.0 arrays were performed by Almac (https://web.archive.org/web/20160317153848/http://www.almacgroup.com/). Methods for recruiting patients with severe influenza, blood sample collection, RNA purification and microarray analysis are as detailed in Hoang et al., 2014.

Microarray data files for the Zaas et al., 2009, Davenport et al., 2015 and Hoang et al., 2014 studies were downloaded from the Gene Expression Omnibus (GEO) database (https://web.archive.org/web/20160622040853/http://www.ncbi.nlm.nih.gov/geo/) using the accession numbers GSE52428, GSE61754 and GSE61821, respectively. Microarray data (.CEL) files for the unpublished study were downloaded from Almac and stored locally for bioinformatics analysis. All four transcriptomic datasets were processed and analysed using the R (version 3.0.2.) integrated suite of software facilities for data manipulation, calculation and graphical display (https://web.archive.org/web/20160623011408/http://www.R-project.org). Quality assessment of raw microarray data was performed using statistical methods standard in the art (e.g. Heber, S. and Sick, B., Quality assessment of affymetrix genechip data, Omics, 2006; 10: 358-368). Affymetrix datasets were normalised using the Robust Multi-array Average (RMA) method [https://www.bioconductor.org/packages/3.3/bioc/manuals/affy/man/affy.pdf] and Illumina datasets were normalised using the Lumi package [https://www.bioconductor.org/packages/3.3/bioc/manuals/lumi/man/lumi.pdf]. Both packages were executed in the R environment. To facilitate annotation of probe-sets and gene names, Affymetrix chip definition files (version 17.1.0) were downloaded from the BrainArray website (https://web.archive.org/web/2016062311275 820160623112758/http://brainarray.mbni.med.umich.edu/Brainarray/Database/CustomCDF/17.1.0/ensg.asp) and Illumina chip definition files (illuminaHumanv4.db) were downloaded from the Bioconductor website (https://web.archive.org/web/20151209032754/http://bioconductor.org/packages/release/dat a/annotation/html/illuminaHumanv4.db.html).

The latter files were used with microarray data from Davenport et al., 2015 and Hoang et al, 2014.

Normalised Zaas et al., 2009, Davenport et al., 2015 and Perth datasets were individually merged with the Hoang et al., 2014 dataset using the COMBAT module in the InSilicoMerging package in Bioconductor (https://web.archive.org/web/20150905151657/http://www.bioconductor.org/packages/relea se/bioc/html/inSilicoMerging.html). Differential gene expression analysis on merged data sets was carried out using the limma package in R (https://www.bioconductor.org/packages/3.3/bioc/vignettes/limma/inst/doc/usersguide.pdf). For pairwise comparisons only data from infected volunteers in the Zaas et al., 2009, Davenport et al., 2015 and Perth datasets were used, equating to 11, 14 and 5 subjects, respectively. From the Hoang et al., 2014 dataset only data for the three H3N2-infected severe influenza patients in the data set were used. For each merged data set two pairwise comparisons were performed to identify genes that were upregulated relative to baseline levels after infection with virus and then further upregulated in the severe patient samples:

Perth: day −1 vs day 3 and; day 3 vs Hoang et al., 2014 severe.

Zaas et al., 2009: day −1 vs 60 hours and; 60 hours vs Hoang et al., 2014 severe.

Davenport et al., 2015: day 0 vs 48 hours and; 48 hours vs Hoang et al., 2014 severe.

To maximise the number of upregulated genes that could be mapped to pathways, all genes showing fold-changes>0 were identified. Each of the 6 resulting gene lists were analysed through the use of QIAGEN's Ingenuity® Pathway Analysis (IPA®, QIAGEN Redwood City, https://web.archive.org/web/20131021061639/http://www.ingenuity.com/). This resulted in the identification of 650 signalling pathways which were reduced to 353 after the removal of 297 metabolic pathways. FIG. 1 summarises this process.

Figure 2:
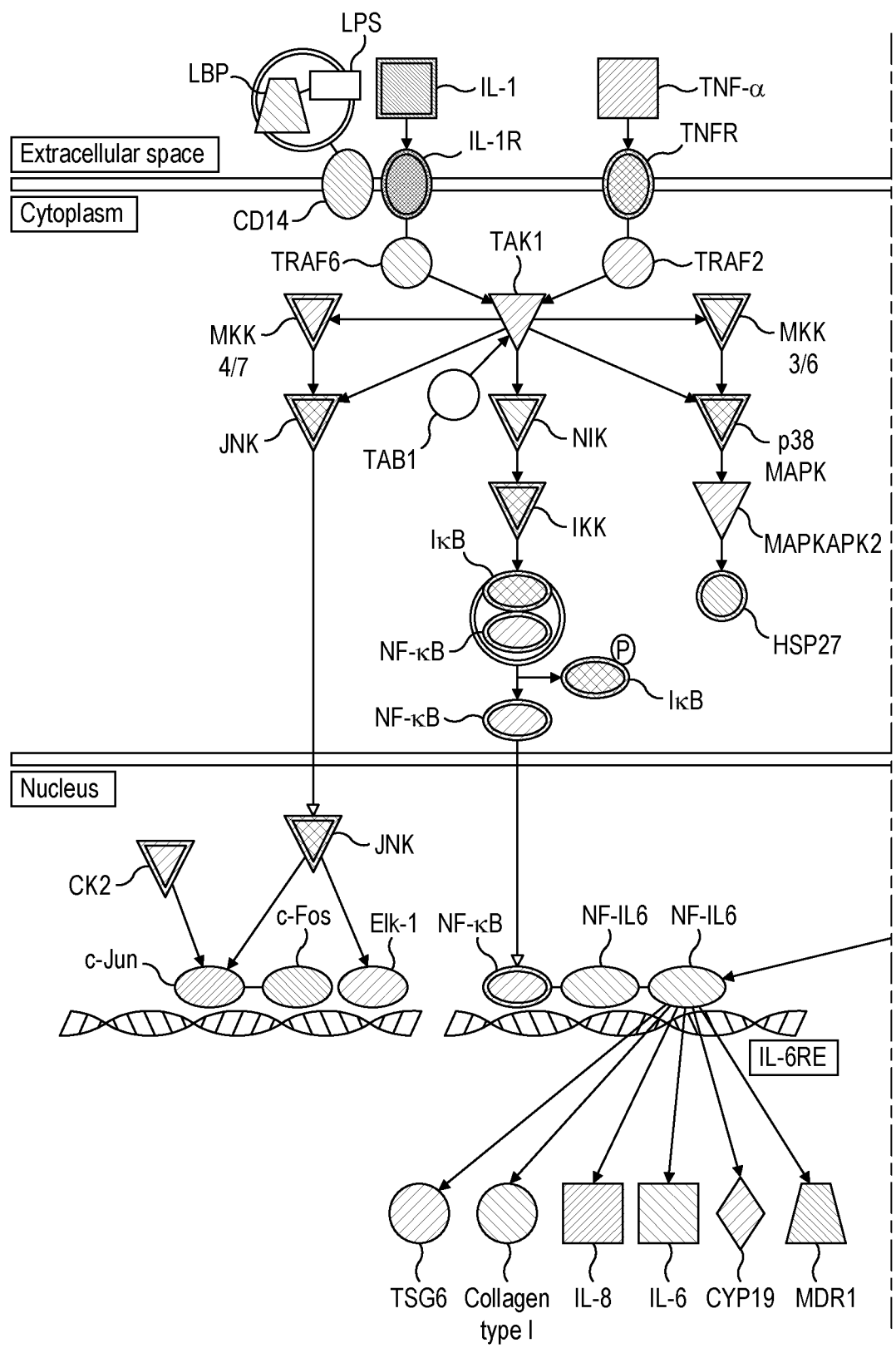
Figure 2:
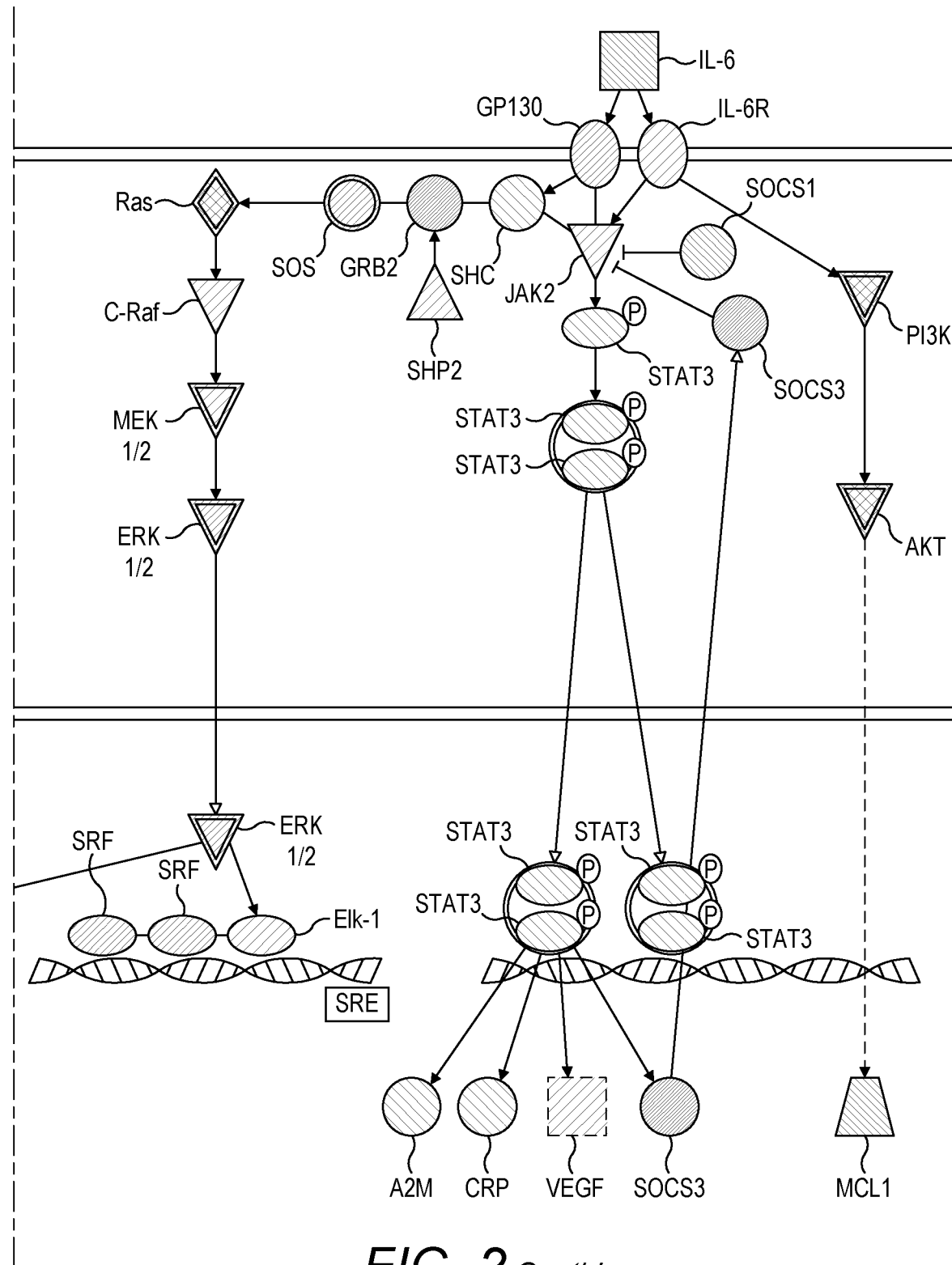

In order to interrogate the relevance of each of these signalling pathways to the pathogenesis of severe influenza, a manual scoring approach was devised to identify very active "routes" within these pathways in the complicated versus the "uncomplicated" influenza datasets. In this context "routes" are defined as contiguous connections of proteins in a canonical pathway that extend from the plasma membrane through to the nucleus. As a result, a canonical pathway may have a number of different routes through it. Using this scoring approach, routes within IPA canonical pathways were mapped directionally from the plasma membrane to the nucleus and the 'overlay' function in IPA was used to show gene activity. To illustrate this process an example of three pathways identified using this method is shown in FIG. 2.

Figure 3:
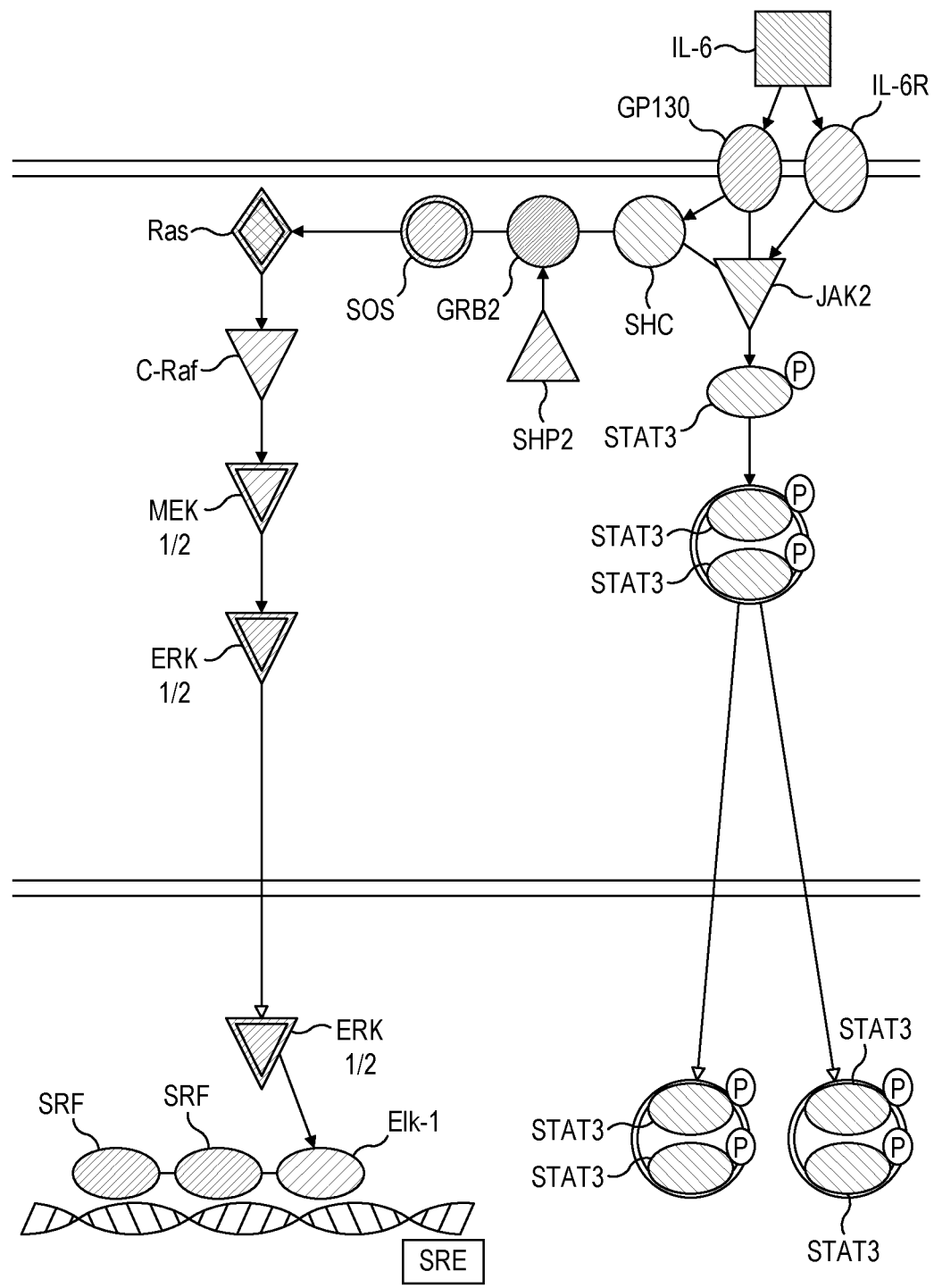

Individual routes in the identified 353 pathways were manually scored for gene activity as exemplified in FIG. 3 for a route through the IL-1 canonical pathway in which:

TABLE 1

| Pathway | Route | Nodes Up-regulated | Nodes not up-regulated |
|---|---|---|---|
| IL-6 signalling | IL6R + GP130-SHC-GRB2-SOS-Ras-cRAF-MEK-ERK-ELK + SRF | 81% | SHC-Ras |

In all, 491 routes showing >75% up-regulated nodes were identified (exemplified in Table 2 below). Of these, 95 routes containing >3 nodes were identified in which 100% of all the nodes in the route were upregulated in the Hoang et al., 2014 severe influenza dataset versus baseline (D-1 or D0) in the Zaas et al., 2009, Davenport et al., 2015 and Perth datasets (Table 3). Twenty-four of these 95 routes were shown to be >75% upregulated compared with pathways derived from the mild and moderate H3N2 and H1N1 influenza datasets from Hoang et al., 2014 (H3N2 and H1N1—mild and moderate) and Zaas et al., 2009 (H1N1-D-1 and 60 h; Table 4).

Inspection of the 95 routes highlighted a number of potentially targetable nodes from which p38MAPK was chosen because of its well characterised role in inflammation and the availability of high quality clinically tested small molecule inhibitors for use in in vitro and ex vivo studies.

TABLE 2

An example of route scoring analysis.

| Pathway | Route | Nodes | Nodes↑ (%) | ↓Nodes |
|---|---|---|---|---|
| NFKB | growth factor receptors-RAS-RAF-MEKK1-IKKa-NFKB2-RELB-lymphogenesis | 10 | 92 | IKKB |
| NFKB | IL-1R/TLR-MYD88-TYRAP-IRAP-IRAK-TRAF6-TAK1-IKKa-IKBP65-P65NFKB-P65NFKB-inflammation | 8 | 93 | IKKB |
| Role of JAK1 and JAK3 in cytokine signalling | IL21Ralpha/IL2Rgamma-JAK3-STAT1/3/5 | 4 | 100 | |
| PI3K-AKT signalling RTK | Integrin-PINCH-ILK-PI3K-PP2A-AKT-CRAF-MEK1/2-ERK1/2-P70S6K-cell growth | 9 | 89 | |
| PI3K-AKT signalling RTK | Integrin-PINCH-ILK-PI3K-PP2A-AKT-CRAF-MEK1/2-ERK1/2-P70S6K-cell growth | 9 | 89 | |
| PI3K-AKT signalling integrin | Integrin-PINCH-ILK-PI3K-PP2A-AKT-CRAF-MEK1/2-ERK1/2-P70S6K-cell growth | 9 | 78 | |
| NFKB | TNF-TANK-TRAF-FADD-RIP-MAP3K3-IKKa-IKBP65-P65NFKB-P65NFKB-inflammation | 7 | 87.5 | TNF-R/IKKB |
| CNTF signalling | (CNTFR-LIFR-GP130)-JAK1/2-SHP2-GRB2-SOS-RAS-CRAF-MEK1/2-ERK1/2-P( )RSK-gene expression | 10 | 90 | SHP2 |
| CNTF signalling | (CNTFR-LIFR-GP130)-TYK2-STAT1/3-gene expression | 3 | 100 | |
| role of JAK in IL-6 type cytokine signalling | (GP130-OSMR)-intermediate signalling-ERK1/2-p38MAPK-JNK-signalling | 4 | 100 | |
| role of JAK in IL-6 type cytokine signalling | (GP130-OSMR)-JAK2-STAT1/3/5-gene expression | 3 | 100 | |
| role of JAK in IL-6 type cytokine signalling | (GP130-OSMR)-STAT1/3-gene expression | 2 | 100 | |
| HER-2 signalling in breast cancer | (HER1/HER2)-GRB2-SOS-RAS-(CYCLIND1-CDK6-CYCLINE-p27KIP1)-cell cycle progression and proliferation | 5 | 80 | HER1-HER2 |
| HER-2 signalling in breast cancer | (HER1/HER2)-PI3K-AKT-CYCLIND1-cell cycle progression | 4 | 75 | HER1-HER2 |
| role of JAk1, JAK2 and TYK2 in interferon signalling | (IFNAR1-IFNAR2)-TYK2-STAT2-STAT1-gene expression | 4 | 100 | |
| IL-9 signalling | (IL-9R-IL2R)-JAK3-IRS1/2-PI3K-PI3ksignalling | 5 | 100 | |

TABLE 3

Ninety-five routes containing 100% upregulated nodes in the Hoang et al., 2014 severe influenza dataset versus the Zaas et al., 2009, Davenport et al., 2015 an dPerth baseline datasets.

| Pathway | Route | Number of Nodes |
|---|---|---|
| Acute myeloid leukemia signalling | FLT3-GRB2-SOS-RAS-RAF-MEK-ERK1/2-cell proliferation | 7 |

TABLE 3-continued

Ninety-five routes containing 100% upregulated nodes in the Hoang et al., 2014 severe influenza dataset versus the Zaas et al., 2009, Davenport et al., 2015 an dPerth baseline datasets.

| Pathway | Route | Number of Nodes |
|---|---|---|
| Gaq signalling | GqR-Ga/b/y-PYK2-PI3K-AKT-IKK-NFkB | 7 |
| p38 MAPK signalling | TNFR/fas-TRADD/FAD-TRAF2-Ask1-MKK4-P38MAKa-CHOP-transcription | 7 |
| p38 MAPK signalling | TNFR/fas-TRADD/FAD-TRAF2-Ask1-MKK4-P38MAKa-ELK1-transcription | 7 |
| p38 MAPK signalling | TNFR/fas-TRADD/FAD-TRAF2-Ask1-MKK4-P38MAPKa-MEF2 | 7 |
| SAPK/JNK signalling | TRADD/RIP/FADD-TRAF2-GCKs-MEKK1-MKK4/7-JNK-ELK-1 | 7 |
| Sertoli cell sertoli cell junction signalling | CLDN-ZO2-factin-actinin alpha-tubulin-KEAP1-Myo7a-junction dynamics | 7 |
| HIF1a signalling | RTK-PI3K-AKT-HIF1a-ARNT-ET1-vascular tone | 6 |
| HIF1a signalling | RTK-PI3K-AKT-HIF1a-ARNT-MMPs-ECM regulation | 6 |
| IL6 signalling | TNFR-TRAF2-TAK1-MKK4/7-JNK-ELK1 | 6 |
| Protein Kinase A signalling | PKAr/PKAc-RAP1-BRAF-MEK1/2-ERK1/2-ELK1 | 6 |
| SAPK/JNK signalling | TRADD/RIP/FADD-TRAF2-ASK1-MKK4/7-JNK-ELK1 | 6 |
| ERK5 signalling | SRC-MEKK2/3-MEK5-ERK5-SAP1 | 5 |
| Glucocorticoid Receptor signalling | CYTOKINE RECEPTOR-TRAF2-TAK1-MKK4/7-P38MAPK-STABILIZATION OF MRNA, TRANSLATION | 5 |
| Growth Hormone signalling | GHR-JAK2-ERK1/2-CEBPA | 5 |
| Growth Hormone signalling | GHR-JAK2-ERK1/2-P90RSK-SRF/ELK1 | 5 |
| HIF1a signalling | RTK-PI3K-AKT-HIF1a-ARNT-GLUT | 5 |
| HIF1a signalling | RTK-PI3K-AKT-HIF1a-ARNT-VEGF | 5 |
| IL-22 signalling | IL22R1/2-TYK2-STAT1/3/5-SOCS3 | 5 |
| IL-8 | CXCR1/2-PI3K-Akt-AP1-IntegrinAlphavBeta3 (Chemotaxis) | 5 |
| IL-8 | CXCR1/2-Ras-Raf-MEK1/2-ERK1/2-(Neutrophil Degranulation) | 5 |
| leptin signalling in obesity | LEPR-JAK2-STAT3-(SOCS3-POMC)-aMSH-anorexia | 5 |
| Paxillin signalling | Integrina/b-FAK-GRB2-SOS-Ras-ERK/MAPK | 5 |
| Role of RIG like receptors in antiviral innate immunity | dsRNA-RIG1-IPS1-TRAF3-TBK1-IRF7-(IFNa-MDA5/LGP2/RIG1) | 5 |
| Role of RIG like receptors in antiviral innate immunity | MDA5-IPS1-TRAF3-TBK1-IRF7-(IFNa-MDA5/LGP2/RIG1) | 5 |
| Role of RIG like receptors in antiviral innate immunity | TRIM25-RIG1-IPS1-TRAF3-IRF7-(IFNa-MDA5/LGP2/RIG1) | 5 |
| CD40 signalling | CD40-JAK3-STAT3-ICAM1 | 4 |
| ceramide signalling | EDG-SPHK-NFKB-AP1-activation of inflammatory genes | 4 |
| ceramide signalling | SMPD-(ceramide)-PI3K-AKT-apoptosis | 4 |
| Eicosanoid signalling | PLA2-ALOX5-LTA4h-LTB4R-chemotaxis/proliferation/allergic asthma/angiogenesis/ | 4 |
| G alpha I signalling | GiCOUPLED RECEPTOR-Galphai/Gbeta/Ggamma-SRC-STAT3 | 4 |
| Germ Cell-Sertoli Cell Junction signalling | TGFbetaR-RAS-MEK1/2-actin depolymerisation | 4 |
| GM-CSF signalling | GMCSFRA-HCK-PI3K-AKT-cell survival/cell proliferation | 4 |
| GM-CSF signalling | GMCSFRA-JAK2-STAT3-(BCLXL-CYCLIND1) | 4 |
| G-Protein Coupled Receptor signalling | Gicoupled receptor-GALPHAi/0-SRC-STAT3 | 4 |
| IGF-1 signalling | IGF1R-JAK 1/2-STAT3-SOCS3 | 4 |
| IL-8 | CXCR1/2-JNK-NFkB-ICAM-1 | 4 |
| IL-8 | CXCR1/2-PI3K-MEK1/2-ERK1/2-(Neutrophil Degranulation) | 4 |
| IL-8 | CXCR1/2-Rho-NFkB-ICAM-1 | 4 |
| JAK/STAT | cytokine receptor-JAK-STAT-(CFOS-IL6-SOCS-BCLXL) | 4 |
| MSP-RON signalling pathway | RON-PI3K-PKC zeta-F-ACTIN-phagocytic activity in macrophages | 4 |
| PI3K signalling in B Lymphocytes | IL4R-IRS-P85/PI3K-P110/PI3K-NFKB | 4 |
| PPARα/RXRα Activation | ADIPOR-AMPK-P38MAPK-PPARalpha | 4 |
| Production of nitric oxide and ROS in macrophages | TLR2/4-PI3K-AKT-NFKB-Inos | 4 |
| Production of nitric oxide and ROS in macrophages | TLR2/4-MKK4/-JNK-AP1 | 4 |
| RAR activation | IL-3Ra/b-JAK2-STAT5-RAR/RXR | 4 |
| Role of MAPK signalling in the Pathogenesis of Influenza | ASK-1-MKK4/7-JNK-CASP3-APOPTOSIS | 4 |
| Role of RIG like receptors in antiviral innate immunity | dsRNA-RIG1-IPS1-TRAF3-IRF7-(IFNa-MDA5/LGP2/RIG1) | 4 |
| Role of RIG like receptors in antiviral innate immunity | MDA5-IPS1-TRAF3-IRF7-(IFNa-MDA5/LGP2/RIG1) | 4 |
| signalling by Rho Family GTPases | Integrin-ARHGEF-RHO-FAK-cytoskeletal reorganisation | 4 |
| signalling by Rho Family GTPases | Integrin-ARHGEF-RHO-PKNI-cell trafficking | 4 |
| Sphingosine-1-phosphate signalling | SIPR(2/3/4)-GAI-PI3K-AKT-CELL SURVIVAL | 4 |
| Tec Kinase signalling | Integrin-FAK-TEC KINASE-(FAK, PKC, PAK, VAV, FACTIN, RHOGTPASE, NFKB, JNK, STAT-TFII-1) | 4 |
| Tec Kinase signalling | TCR-SRC-TEC KINASE-(FAK, PKC, PAK, VAV, FACTIN, RHOGTPASE, NFKB, JNK, STAT-TFII-1) | 4 |
| Acute myeloid leukemia signalling | FLT3-STAT3/5-PIM1-regulates apoptosis | 3 |
| Antioxidant action of vitamin C | CSF2Ralpha/beta-JAK2-STAT5-gene expression | 3 |
| CNTF signalling | (CNTFR-LIFR-GP130)-TYK2-STAT1/3-gene expression | 3 |
| Dendritic Cell Maturation | LTbetaR-IKK-RELB/NFKB-cross presentation | 3 |
| EPHRIN RECEPTOR signalling | EPHA-JAK2-STAT3-CELL PROLIFERATION | 3 |
| EPHRIN RECEPTOR signalling | EPHB-PI3KG-AKT-CELL MIGRATION, CELL PROLIFERATION | 3 |
| EPHRIN RECEPTOR signalling | INTEGRIN-MEK1/2-ERK1/2-AXON GUIDANCE, CELL PROLIFERATION | 3 |
| FcyRIIB signalling in B lymphocytes | FCyR-BTK-JNK-apoptosis | 3 |

TABLE 3-continued

Ninety-five routes containing 100% upregulated nodes in the Hoang et al., 2014 severe influenza dataset versus the Zaas et al., 2009, Davenport et al., 2015 an dPerth baseline datasets.

| Pathway | Route | Number of Nodes |
|---|---|---|
| Glucocorticoid Receptor signalling | CYTOKINE RECEPTOR-JAK2-STAT1 | 3 |
| Glucocorticoid Receptor signalling | CYTOKINE RECEPTOR-JAK3-STAT3/5 | 3 |
| GNRH signalling | GnRHR-Gai-NfkB | 3 |
| IL-12 signalling and Production in Macrophages | TLR4-p38/MAPK-IL12 | 3 |
| IL-3 signalling | IL3Ralpha/beta-JAK1/2-STAT1/3/5/6-gene expression | 3 |
| IL6 signalling | GP130 (IL6R)-JAK2-STAT3-gene expression | 3 |
| IL-8 | CXCR1-PLD-NADPH oxidase-(Superoxide production—Respiratory Burst) | 3 |
| IL-8 | CXCR1-G Protein alpha/beta/gamma-PI3Ky-(Chemotaxis—Respiratory Burst) | 3 |
| LPS stimulated MAPK signalling | TLR4-IKK-IKB-NFKB-gene expression | 3 |
| mTOR signalling | Nutrients-RHEB-mTORc2-AKT-PI3K/AKT signalling | 3 |
| mTOR signalling | Nutrients-RHEB-mTORc2-AKT-Rho/PKC)-actin organisation | 3 |
| PDGF signalling | PDGFRa/b-SPHK-CRK-mitogenesis | 3 |
| Protein Kinase A signalling | PKA-PHK-PYG-glycolysis | 3 |
| Regulation of cellular mechanics by calpain protease | CNG-CALPAIN-RB | 3 |
| role of JAK in IL-6 type cytokine signalling | (GP130-OSMR)-JAK2-STAT1/3/5-gene expression | 3 |
| Role of JAK2 in Hormone-like cytokine signalling | GHR-JAK2-IRS-PI3K/AKT SIGNALLING | 3 |
| Role of JAK2 in Hormone-like cytokine signalling | GHR-JAK2-STAT1/3-GENE EXPRESSION | 3 |
| Role of JAK2 in Hormone-like cytokine signalling | GHR-JAK2-STAT5-GENE EXPRESSION | 3 |
| Role of Macrophages, Fibroblasts and Endothelial Cells in Rheumatoid Arthritis | GP130-JAK2-STAT3-gene expression | 3 |
| Role of Pattern Recognition Receptors in Recognition of Bacteria and Viruses | NALP3-casp1-IL1b | 3 |
| Role of Pattern Recognition Receptors in Recognition of Bacteria and Viruses | NOD1-Casp1-IL1b | 3 |
| Role of PI3K/AKT signalling in the Pathogenesis of Influenza | PI3K-AKT-IKB, NFKB | 3 |
| Role of tissue factor in cancer | PAR2-ERK1/2-HBEGF-angiogenesis | 3 |
| Role of tissue factor in cancer | PAR2-ERK1/2-VEGFa-angiogenesis | 3 |
| Role of tissue factor in cancer | PAR2-p38/MAPK-uPar-tumour invasion | 3 |
| Role of tissue factor in cancer | PAR2-p38/MAPK-IL-1b-angiogenesis | 3 |
| Role of tissue factor in cancer | PAR2-p38/MAPK-VEGFa-angiogenesis | 3 |
| STAT3 pathway | cytokine receptors-TYK2/JAK2-STAT3-transcription-immune response-proliferation-survival | 3 |
| STAT3 pathway | GFR-JAK2/SRC-STAT3-transcription-immune response-proliferation-survival | 3 |
| Synaptic long term depression | AMPAR-Lyn-PKC-Phosphorylation | 3 |
| Tec Kinase signalling | FCeR1-TEC kinase-(FAK, PKC, PAK, VAV, FACTIN, RHOGTPASE, NFKB, JNK, STAT-TFII-1) | 3 |
| Tec Kinase signalling | TLR4-TEC kinase-(FAK, PKC, PAK, VAV, FACTIN, RHOGTPASE, NFKB, JNK, STAT-TFII-1) | 3 |

TABLE 4

Comparison of route scores between H3N2 and H1N1.

| | | H3N2 | | | |
|---|---|---|---|---|---|
| Pathway | Route | Severe vs Baseline H3N2 | Severe vs Peak H3N2 | Severe vs Mild H3N2 | Severe vs Moderate H3N2 |
| Growth Hormone signalling | GHR-JAK2-ERK1/2-CEBPA | 100.00 | 93.33 | 100.00 | 100 |
| PPARα/RXRα Activation | ADIPOR-AMPK-P38MAPK-PPARalpha-REGULATION of growth hormone genes | 100.00 | 100.00 | 100.00 | 100 |
| GM-CSF signalling | GMCSFRA-HCK-PI3K-AKT-cell survival/cell proliferation | 100.00 | 100.00 | 100.00 | 100 |
| Sphingosine-1-phosphate signalling | SIPR(2/3/4)-GAI-PI3K-AKT-CELL SURVIVAL | 100.00 | 100.00 | 100.00 | 100 |
| ceramide signalling | SMPD-(ceramide)-PI3K-AKT-apoptosis | 100.00 | 100.00 | 100.00 | 100 |
| IL-8 | CXCR1/2 - PI3K-MEK1/2-ERK1/2- (Neutrophil Degranulation) | 100.00 | 93.33 | 100.00 | 100 |

TABLE 4-continued

Comparison of route scores between H3N2 and H1N1.

| Pathway | Route | | | | |
|---|---|---|---|---|---|
| Paxillin signalling | Integrina/b-FAK-GRB2-SOS - Ras-ERK/MAPK | 100.00 | 100.00 | 100.00 | 100 |
| Tec Kinase signalling | FCeR1-TEC kinase-(FAK, PKC, PAK, VAV, FACTIN, RHOGTPASE, NFKB, JNK, STAT-TFII-1) | 100.00 | 100.00 | 100.00 | 100 |
| Tec Kinase signalling | TCR-SRC-TEC KINASE-(FAK, PKC, PAK, VAV, FACTIN, RHOGTPASE, NFKB, JNK, STAT-TFII-1) | 100.00 | 100.00 | 100.00 | 100 |
| Tec Kinase signalling | TLR4-TEC kinase-(FAK, PKC, PAK, VAV, FACTIN, RHOGTPASE, NFKB, JNK, STAT-TFII-1) | 100.00 | 100.00 | 100.00 | 100 |
| signalling by Rho Family GTPases | Integrin-ARHGEF-RHO-PKNI-cell trafficking | 100.00 | 100.00 | 100.00 | 100 |
| Regulation of cellular mechanics by calpain protease | CNG-CALPAIN-RB | 100.00 | 100.00 | 100.00 | 100 |
| Tec Kinase signalling | Integrin-FAK-TEC KINASE-(FAK, PKC, PAK, VAV, FACTIN, RHOGTPASE, NFKB, JNK, STAT-TFII-1) | 100.00 | 100.00 | 100.00 | 100 |
| Acute myeloid leukemia signalling | FLT3-GRB2-SOS-RAS-RAF-MEK-ERK1/2-cell proliferation | 100.00 | 100.00 | 100.00 | 85.71 |
| signalling by Rho Family GTPases | Integrin-ARHGEF-RHO-FAK-cytoskeletal reorganisation | 100.00 | 95.23 | 100.00 | 100 |
| IL-8 | CXCR1/2 - Ras-Raf-MEK1/2-ERK1/2- (Neutrophil Degranulation) | 100.00 | 91.67 | 100.00 | 100 |
| JAK/STAT | cytokine receptor-JAK-STAT-(CFOS-IL6-SOCS-BCLXL) | 100.00 | 91.67 | 100.00 | 100 |
| MSP-RON signalling pathway | RON-PI3K-PKC zeta- F-ACTIN-phagocytic activity in macrophages | 100.00 | 91.67 | 100.00 | 100 |
| Germ Cell-Sertoli Cell Junction signalling | TGFbetaR-RAS-MEK1/2-ERK1/2-actin depolymerisation | 100.00 | 91.67 | 100.00 | 100 |
| Role of MAPK signalling in the Pathogenesis of Influenza | ASK-1-MKK4/7-JNK-CASP3 - APOPTOSIS | 100.00 | 83.33 | 100.00 | 100 |
| Role of PI3K/AKT signalling in the Pathogenesis of Influenza | PI3K-AKT-IKB, NFKB | 100.00 | 77.78 | 100.00 | 100 |
| Protein Kinase A signalling | PKAr/PKAc-RAP1-BRAF-MEK1/2-ERK1/2-ELK1 | 100.00 | 100.00 | 83.33 | 83.33 |
| IL-8 | CXCR1/2 - PI3K-Akt-AP1-IntegrinAlphavBeta3 (Chemotaxis) | 100.00 | 80.55 | 80.00 | 100 |
| Production of nitric oxide and ROS in macrophages | TLR2/4-MKK4/7-JNK-AP1 | 100.00 | 91.67 | 75.00 | 100 |

| | | H1N1 | | | |
|---|---|---|---|---|---|
| Pathway | Route | Severe vs Baseline H1N1 | Severe vs Peak H1N1 | Severe vs Mild H1N1 | Severe vs Moderate H1N1 |
| Growth Hormone signalling | GHR-JAK2-ERK1/2-CEBPA | 75 | 75 | 75 | 75 |
| PPARα/RXRα Activation | ADIPOR-AMPK-P38MAPK-PPARalpha-REGULATION of growth hormone genes | 100 | 100 | 100 | 75 |
| GM-CSF signalling | GMCSFRA-HCK-PI3K-AKT-cell survival/cell proliferation | 100 | 100 | 100 | 100 |
| Sphingosine-1-phosphate signalling | SIPR(2/3/4)-GAI-PI3K-AKT-CELL SURVIVAL | 100 | 100 | 100 | 100 |
| ceramide signalling | SMPD-(ceramide)-PI3K-AKT-apoptosis | 100 | 100 | 100 | 100 |
| IL-8 | CXCR1/2 - PI3K-MEK1/2-ERK1/2- (Neutrophil Degranulation) | 75 | 75 | 100 | 100 |
| Paxillin signalling | Integrina/b-FAK-GRB2-SOS - Ras-ERK/MAPK | 100 | 100 | 100 | 100 |
| Tec Kinase | FCeR1-TEC kinase- | 100 | 100 | 100 | 100 |

TABLE 4-continued

Comparison of route scores between H3N2 and H1N1.

| Pathway | Route | | | | |
|---|---|---|---|---|---|
| signalling | (FAK, PKC, PAK, VAV, FACTIN, RHOGTPASE, NFKB, JNK, STAT-TFII-1) | | | | |
| Tec Kinase signalling | TCR-SRC-TEC KINASE- (FAK, PKC, PAK, VAV, FACTIN, RHOGTPASE, NFKB, JNK, STAT-TFII-1) | 100 | 100 | 100 | 100 |
| Tec Kinase signalling | TLR4-TEC kinase- (FAK, PKC, PAK, VAV, FACTIN, RHOGTPASE, NFKB, JNK, STAT-TFII-1) | 100 | 100 | 100 | 100 |
| signalling by Rho Family GTPases | Integrin-ARHGEF-RHO-PKNI-cell trafficking | 75 | 75 | 75 | 75 |
| Regulation of cellular mechanics by calpain protease | CNG-CALPAIN-RB | 100 | 100 | 100 | 100 |
| Tec Kinase signalling | Integrin-FAK-TEC KINASE- (FAK, PKC, PAK, VAV, FACTIN, RHOGTPASE, NFKB, JNK, STAT-TFII-1) | 100 | 100 | 100 | 100 |
| Acute myeloid leukemia signalling | FLT3-GRB2-SOS-RAS-RAF-MEK-ERK1/2-cell proliferation | 100 | 100 | 100 | 100 |
| signalling by Rho Family GTPases | Integrin-ARHGEF-RHO-FAK-cytoskeletal reorganisation | 100 | 100 | 100 | 100 |
| IL-8 | CXCR1/2 - Ras-Raf-MEK1/2-ERK1/2- (Neutrophil Degranulation) | 80 | 80 | 100 | 100 |
| JAK/STAT | cytokine receptor-JAK-STAT- (CFOS-IL6-SOCS-BCLXL) | 75 | 75 | 100 | 100 |
| MSP-RON signalling pathway | RON-PI3K-PKC zeta- F-ACTIN-phagocytic activity in macrophages | 75 | 100 | 75 | 75 |
| Germ Cell-Sertoli Cell Junction signalling | TGFbetaR-RAS-MEK1/2-ERK1/2-actin depolymerisation | 100 | 100 | 100 | 100 |
| Role of MAPK signalling in the Pathogenesis of Influenza | ASK-1-MKK4/7-JNK-CASP3 - APOPTOSIS | 75 | 75 | 75 | 75 |
| Role of PI3K/AKT signalling in the Pathogenesis of Influenza | PI3K-AKT-IKB, NFKB | 100 | 100 | 75 | 75 |
| Protein Kinase A signalling | PKAr/PKAc-RAP1-BRAF-MEK1/2-ERK1/2-ELK1 | 100 | 83.33 | 83.33 | 83.33 |
| IL-8 | CXCR1/2 - PI3K-Akt-AP1-IntegrinAlphavBeta3 (Chemotaxis) | 75 | 80 | 100 | 100 |
| Production of nitric oxide and ROS in macrophages | TLR2/4-MKK4/7-JNK-AP1 | 100 | 100 | 100 | 100 |

Example 2

Effects of p38MAPK Inhibition on Inflammatory Mediator Release in Key Cell Types Relevant to Severe Influenza Two p38 MAPK inhibitors were used in in vitro and ex vivo experiments: 1) PH797804, an ATP-competitive highly potent, selective and metabolically stable inhibitor of p38 (Hope HR1, et al., Anti-inflammatory properties of a novel N-phenyl pyridinone inhibitor of p38 mitogen-activated protein kinase: preclinical-to-clinical translation, *J. Pharmacol. Exp. Ther.*, 2009 (December); 331(3): 882-95); and 2) Dilmapimod (SB-681323- Betts JC1, et al., Gene expression changes caused by the p38 MAPK inhibitor Dilmapimod in COPD patients: analysis of blood and sputum samples from a randomized, placebo-controlled clinical trial, *Pharmacol. Res. Perspect.*, 2015 (February); 3(1): e00094). The structures of these compounds are as follows:

Dilmapimod

-continued

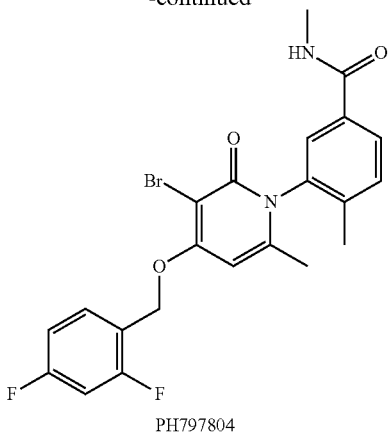
PH797804

Figure 4:
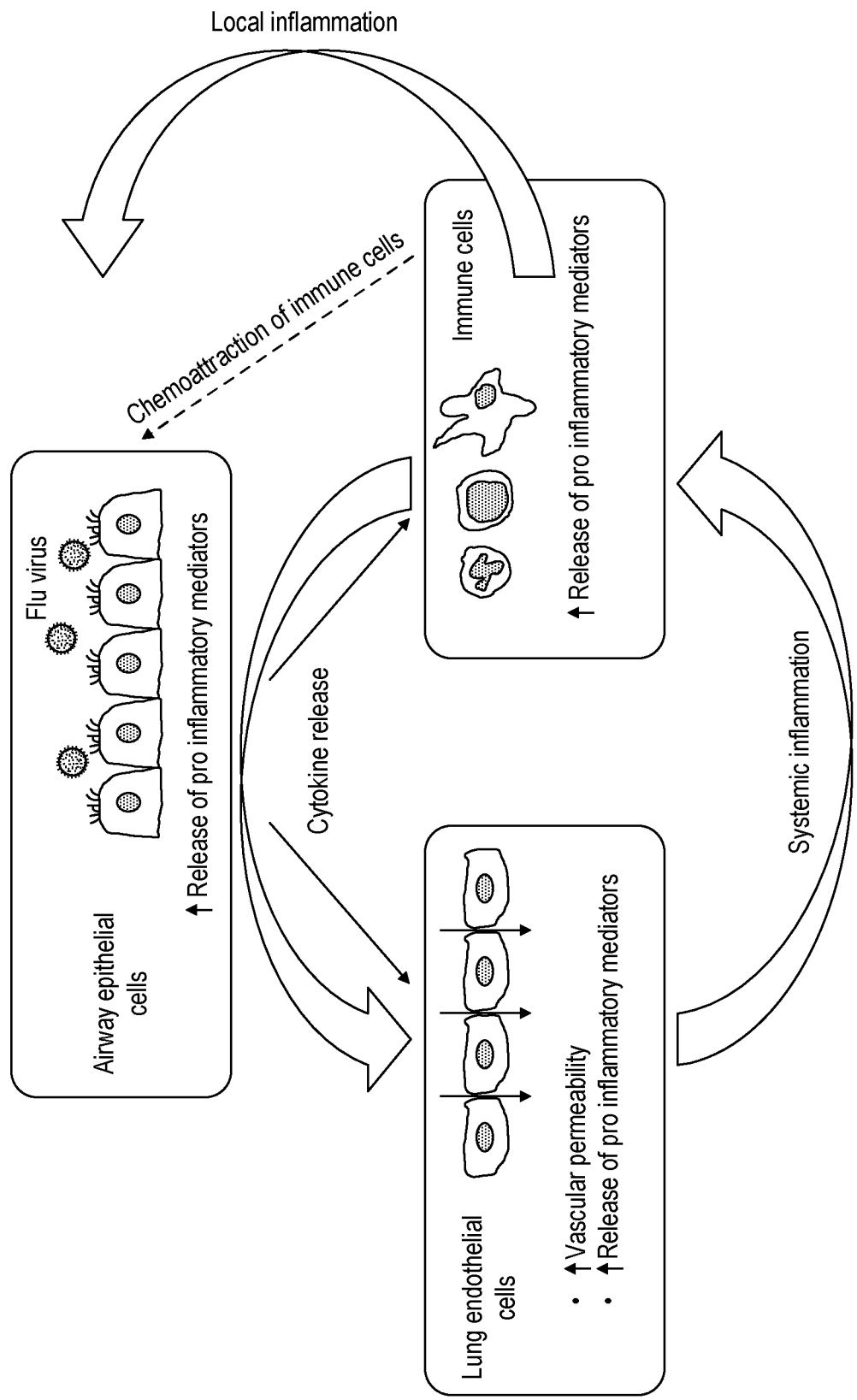

Experimental testing of p38MAPK inhibition was carried out in three cell types that are key players in the pathology of severe influenza: epithelial; endothelial; and immune cells (FIG. 4). In these experiments, cells were pre-treated with simple and/or complex stimuli in order to simulate the action of inflammatory mediators that are produced from influenza-infected epithelial cells. In the case of the former, tumour necrosis factor alpha (TNFa) plus interleukin 6 (IL-6) was used to stimulate endothelial and immune cells. In the case of the latter, conditioned medium (viral "soup") derived either from influenza virus infected A549 cells (adenocarcinoma human alveolar basal epithelial cells), or primary human bronchial epithelial cells (HBECs) was used to stimulate epithelial, endothelial and immune cells.

Epithelial Cells

A549 cells (adenocarcinoma human alveolar basal epithelial cells) or HBEC (Human Bronchial Epithelial Cells) were infected with A/Perth/16/2009(H3N2) virus from which viral conditioned media (or 'viral soup') was collected. In the experiments described here, the application of viral soup either back onto epithelial cells or onto the other cell types of interest (endothelial and immune) was performed in order to simulate the action of inflammatory mediators that are produced from Influenza infected epithelial cells.

For infection, high titre stocks of Influenza (H3N2) virus were produced by infection of MDCK-RVL cells (available from ATCC as MDCK (NBL-2) (ATCC® CCL-34), derived from a kidney of an apparently normal adult female cocker spaniel, September, 1958, by S. H. Madin and N. B. Darby. The line is hyperdiploid, and there is a bi-modal chromosome number distribution. There are no consistent identifiable marker chromosomes. One normal X chromosome is present in most spreads. The cells are positive for keratin by immunoperoxidase staining). MDCK-RVL cells were plated in T175 flask and allowed to grow to 85-90% confluence. The next day, cells were washed twice with infection media. The Influenza A/Perth/16/2009 (H3N2) stock was removed from −80° C. and thawed on ice. The cells were infected with virus stock at 0.01 MOI for one hour in infection media. At the end of incubation period, unbound virus was removed from the cells. The cells were washed once with infection media and overlaid with infection media and allowed to incubate for 48 hours in 37° C. at 5% $CO_2$/air incubator. After incubation, the flasks were frozen at −80° C. for a day. Next day, the flasks were thawed at room temperature and virus supernatant was centrifuged (2000 g, 10 min) and pooled together. The virus stock was aliquoted and stored at −80° C.

Viral "soups" were prepared using the A549 cell line and primary human bronchial epithelial cells (HBECs). For the preparation of A549 soups cells were plated in a T175 flask and allowed to grow to obtain 85-90% confluence. The cells were washed twice with infection media. The Influenza A/Perth/16/2009 (H3N2)-WGC stock was removed from −80° C. and thawed on ice. The cells were infected with virus stock at 0.01 MOI for one hour in infection media. The unbound virus was removed from the cells at the end of the incubation period and cells were washed once with infection media before overlaying with infection media. The cells were incubated for 48 hours in 37° C. at 5% $CO_2$/air incubator. After incubation, the media ('viral soup') was collected from all flasks, centrifuged (2000 g, 10 min) and pooled together. The viral soup was aliquoted and stored at −80° C. For the preparation of HBEC viral soup cells were cultured to passage P-3 or P-4 in Bronchial Epithelial Cell Growth Medium (BECGM; Lonza). For infection, cells were washed twice with BECGM then infected with Influenza A/Perth/16/2009 (H3N2) virus stock at 0.01 MOI for one hour in infection medium (BECGM containing 1.06 USP/NF units per ml TPCK trypsin). The cells were then overlaid with infection medium and incubated for 48 hours at 37° C. in 5% $CO_2$/air. The HBEC viral soup was then processed in a similar way to A549 soup.

Viral growth kinetics were optimised for generating viral soups. To determine multistep growth curves, A549 cells or HBECs were infected with virus at an MOI of 0.01 $TCID_{50}$/cell at 37° C. for one hour. Following incubation, the cells were washed and overlaid with respective infection media. The samples were harvested for viral titres and measurement of cytokines at various time points for 72 hours. The viral titres were obtained by $TCID_{50}$ on MDCK cells and the presence of inflammatory mediators was assessed by MSD chemiluminescence assay using methods as recommended by the vendor (https://web.archive.org/web/20160522190937/https://www.mesoscale.com/).

Figure 5:
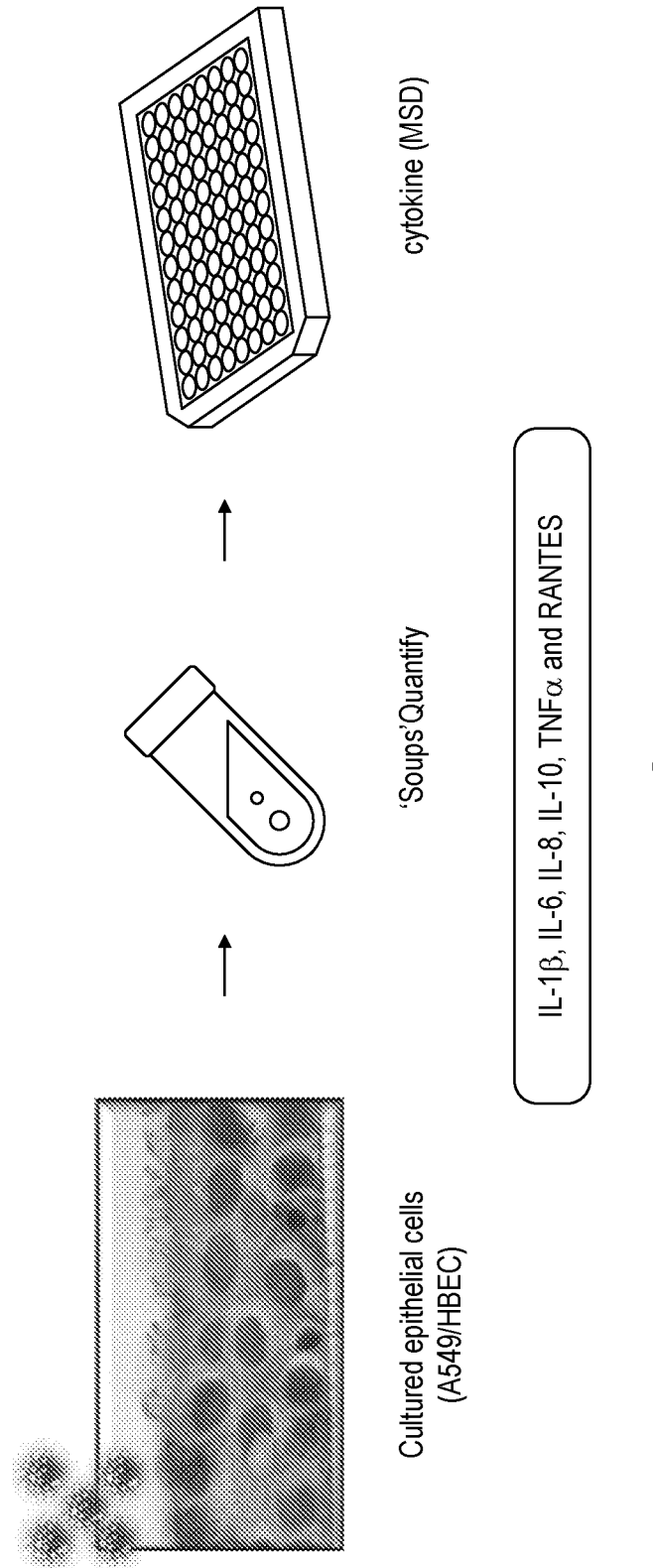

Prior to experimental testing both A549 and HBEC soup preparations were evaluated by electrogenerated chemiluminescence for the presence of inflammatory mediators using methods as recommended by the vendor (https://web.archive.org/web/20160522190937/https://www.mesoscale.com/). Both soup preparations were found to contain elevated levels of the following cytokines (IL1-β, IL-6, IL-8, IL-10, TNFα and RANTES; FIG. 5).

In vitro data were generated from A549 cells to test the effect of A549 viral soup application on p38 activation as measured by western blotting of the phosphorylation status of p38MAPK itself and downstream signalling target, HSP27. For western blotting confluent cells were washed in PBS and lysed in RIPA with protease inhibitor (Sigma-P8340), phosphatase inhibitor cocktails 2 and 3 (Sigma P5726 and P0044) and phosphatase inhibitors $Na_3VO_4$ and NaF on ice. Protein concentrations were determined using the Pierce BCA Protein Assay Kit and equal concentrations of each sample created in 4× Laemmli sample buffer (BIO-RAD 161-0747) with 2-mercaptoethanol. Samples were run on a 12% gel and then transferred on to nitrocellulose. Membranes were blocked using 5% milk powder, then hybridised with p38 MAPK rabbit antibody (Cell Signalling Technologies, cat. no. 9212S) and phosphorylated p38 MAPK rabbit antibody (Cell Signalling Technologies, cat. no. 9211S), or HSP27 antibody (Cell signalling Technologies, cat. no. 2402) and phospho-HSP27 antibody (Cell signalling Technologies, cat. no. 9709). Secondary antibodies were anti-rabbit HRP (Cell signalling Technologies catalogue no. CS7074P2) and anti-mouse HRP (Cell signalling, catalogue no. 7076S), respectively. Membranes were stripped for re-probing using Restore™ PLUS Western Blot Stripping Buffer (Life technologies #46430). The membranes were treated with Amersham ECL Prime Western Blotting Detection Reagent (GE/Amersham #RPN2232) and imaged using ChemiDoc™ Touch Imaging System (BIO-RAD). Analysis was performed using the Image Lab software.

Figure 6:
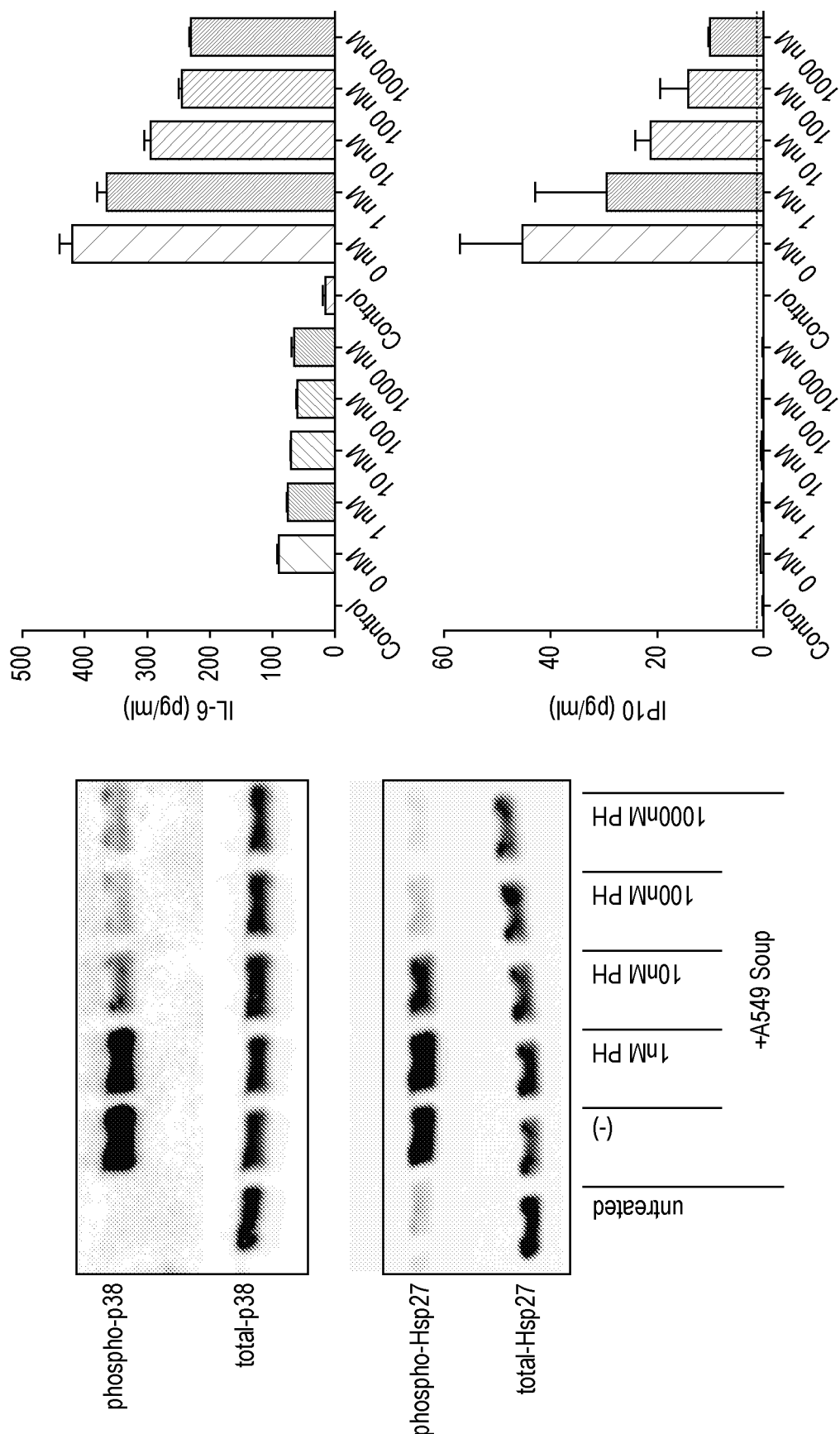

Induction of phosphorylation on both of these enzymes was detected indicating that p38MAPK is activated following application of A549 viral soup (FIG. 6). Furthermore, incubation with p38 MAPK inhibitors (Dilmapimod and PH 797804) was shown to dose dependently inhibit the induction of both p38MAPK and HSP27 phosphorylation by our A549 viral soup, confirming that this induction is a p38MAPK dependent process within these epithelial cells.

The effect of A549 viral soup on inflammatory cytokine production in A549 cells as measured by electrogenerated chemiluminescence was also explored. As shown in FIG. 6, A549 soup was found to induce the production of key inflammatory cytokines (IL-6 and IP-10) to a greater extent compared with control uninfected A549 soup. Application of the two p38 MAPK inhibitors on A549 cells prior to A549 viral soup application significantly attenuated release of both IL-6 and IP-10 (FIG. 6 shows the data for the p38 MAPK inhibitor PH 797804). These data demonstrate that the release of inflammatory mediators in response to A549 viral soup application on A549 cells is a p38MAPK dependent process.

Endothelial Cells

The application of HBEC viral soup on to Human Umbilical Vein Endothelial Cells (HUVECs) was performed in order to simulate the interaction of inflammatory mediators that are produced from Influenza infected epithelial cells onto endothelial cells.

Figure 7:
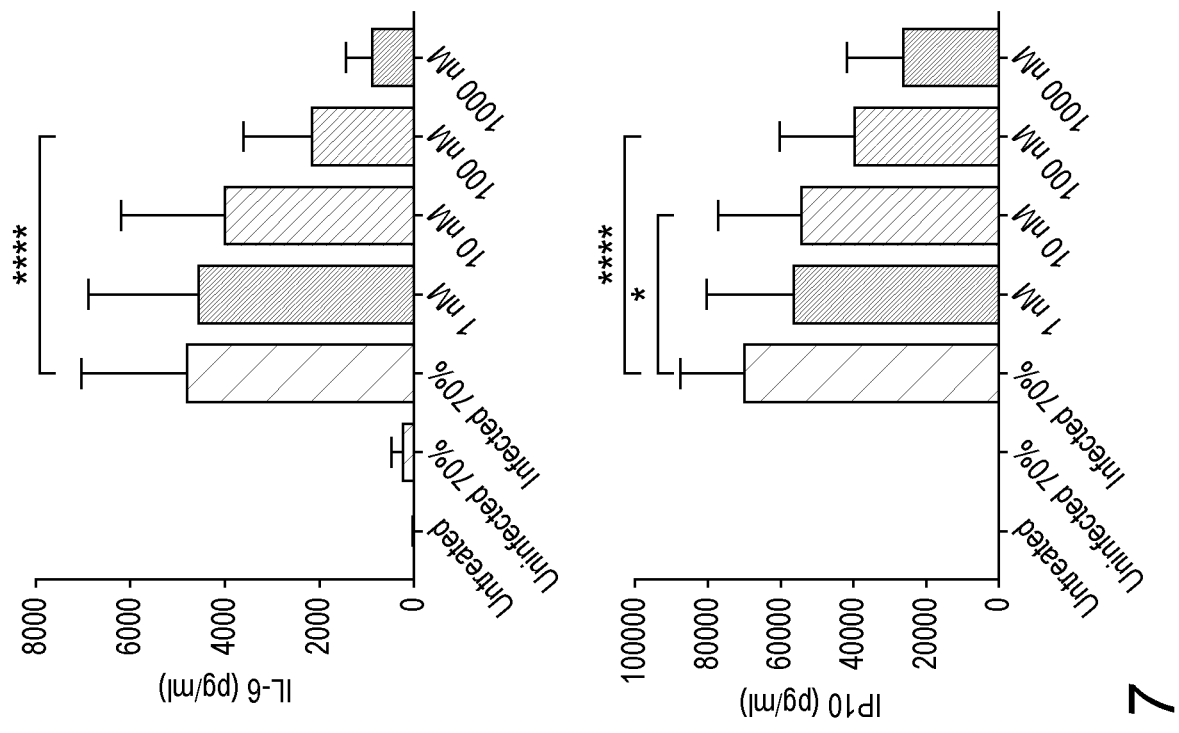
Figure 7:
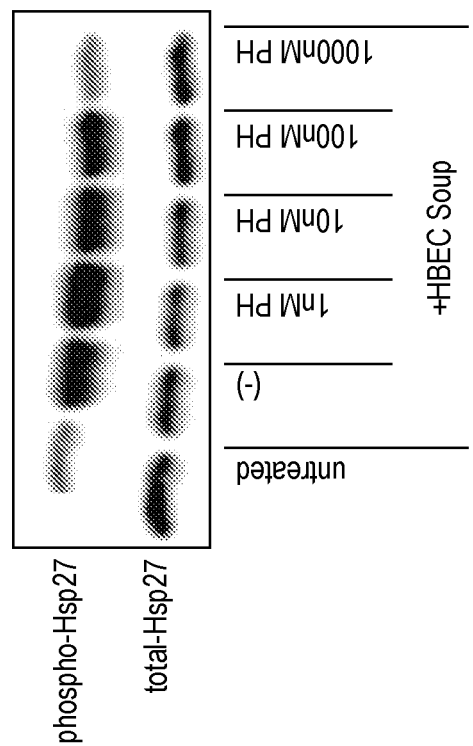

In vitro data were generated from HUVEC cells to test the effect of HBEC viral soup application on p38 activation as measured by western blotting of the phosphorylation status of the p38MAPK downstream signalling target, HSP27. Induction of phosphorylation on HSP27 was detected indicating that p38MAPK is activated following application of HBEC viral soup (FIG. 7). Furthermore, pre-incubation with p38 MAPK inhibitors (Dilmapimod and PH 797804) was shown to dose dependently inhibit the induction of HSP27 phosphorylation by the HBEC viral soup, confirming that this induction is a p38MAPK dependent process within these endothelial cells.

The effect of HBEC viral soup on inflammatory cytokine production in HUVEC cells as measured by electrogenerated chemiluminescence (see methods) was also explored. As shown in FIG. 7, HBEC viral soup was found to induce the production of key inflammatory cytokines (IL-6 and IP-10) to a greater extent compared with control HBEC uninfected soup. Incubation of HUVEC cells with the two p38 MAPK inhibitors prior to HBEC viral soup application was found to significantly attenuate the HBEC viral soup induced release of both IL-6 and IP-10 (FIG. 7). These data demonstrate that the release of inflammatory mediators in response to HBEC viral soup application in HUVEC endothelial cell is a p38MAPK dependent process.

Immune Cells

The application of A549 viral soup onto human Peripheral Blood Mononuclear Cells (PBMCs) was performed in order to simulate the interaction of inflammatory mediators that are produced from Influenza infected epithelial cells onto immune cells. PBMCs were isolated according to the manufacturers recommendations (Boyum, A., Separation of leucocytes from blood and bone marrow, *Scand. J. Clin. Lab. Invest.*, 1968, 21, suppl. 97).

Figure 8:
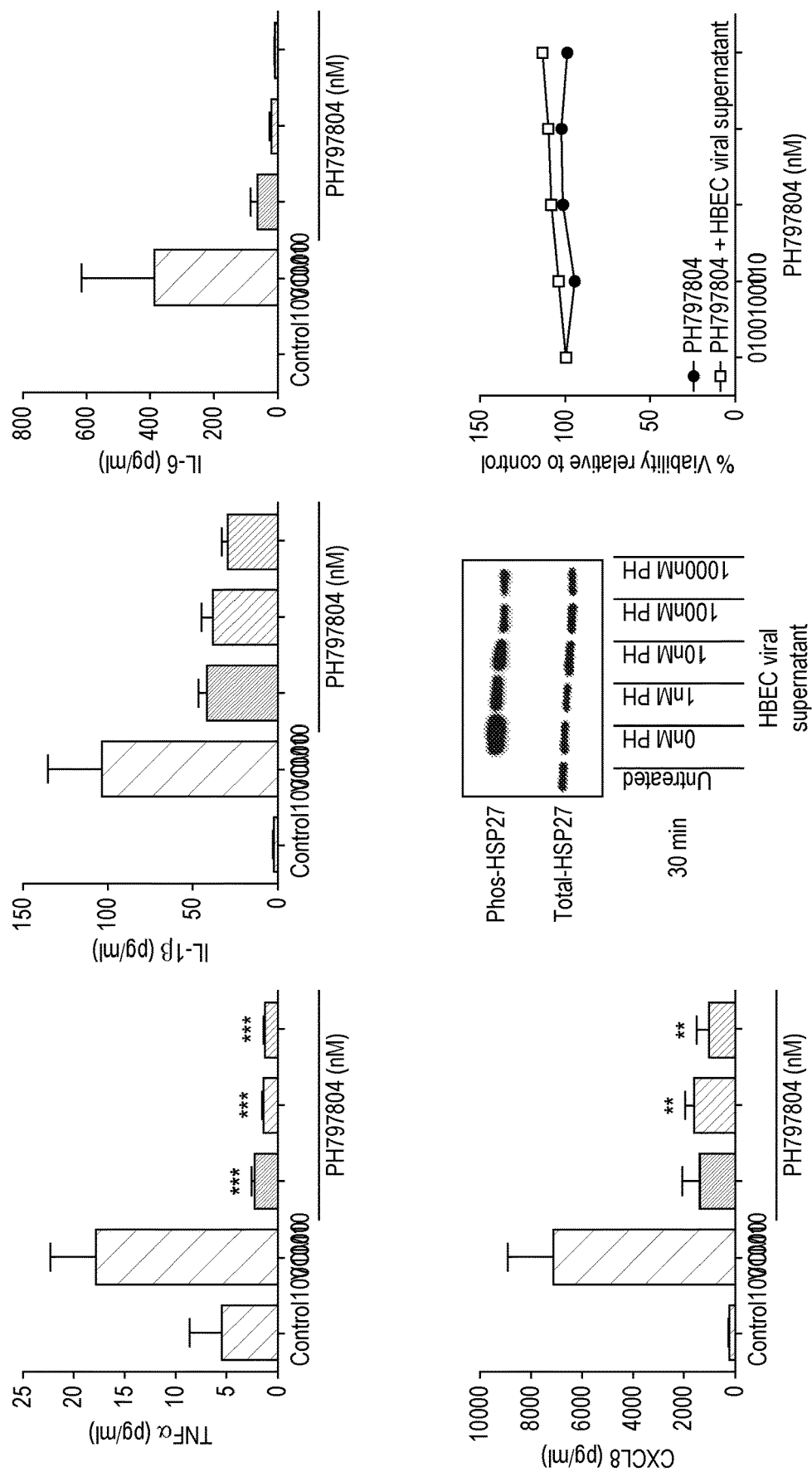

Ex vivo data were generated from immune cells to test the effect of A549 viral soup application on p38 activation as measured by Western blotting (see above for method) of the phosphorylation status of the p38MAPK downstream signalling target, HSP27. Induction of phosphorylation on HSP27 was detected, indicating that p38MAPK is activated following application of A549 viral soup (FIG. 8). Furthermore, pre-incubation with p38 MAPK inhibitors (Dilmapimod and PH 797804) was shown to dose dependently inhibit the induction of HSP27 phosphorylation by the A549 viral soup, confirming that this induction is a p38MAPK dependent process within these immune cells (FIG. 8).

The effect of A549 viral soup on inflammatory cytokine production in immune cells as measured by electrogenerated chemiluminescence (see above) was also explored. As shown in FIG. 8, A549 viral soup was found to induce the production of key inflammatory cytokines (TNFα, IL-1-β, IL-6 and CXCL8) to a greater extent compared with control A549 uninfected soup. Pre-incubation of p38 MAPK inhibitors (Dilmapimod and PH 797804) on immune cells prior to A549 viral soup application was found to significantly attenuate the A549 viral soup induced release of TNFα, IL-1-β, IL-6 and CXCL8 (FIG. 8). These data demonstrate that the release of inflammatory mediators in response to A549 viral soup application in immune cells is a p38MAPK driven process.

Figure 9:
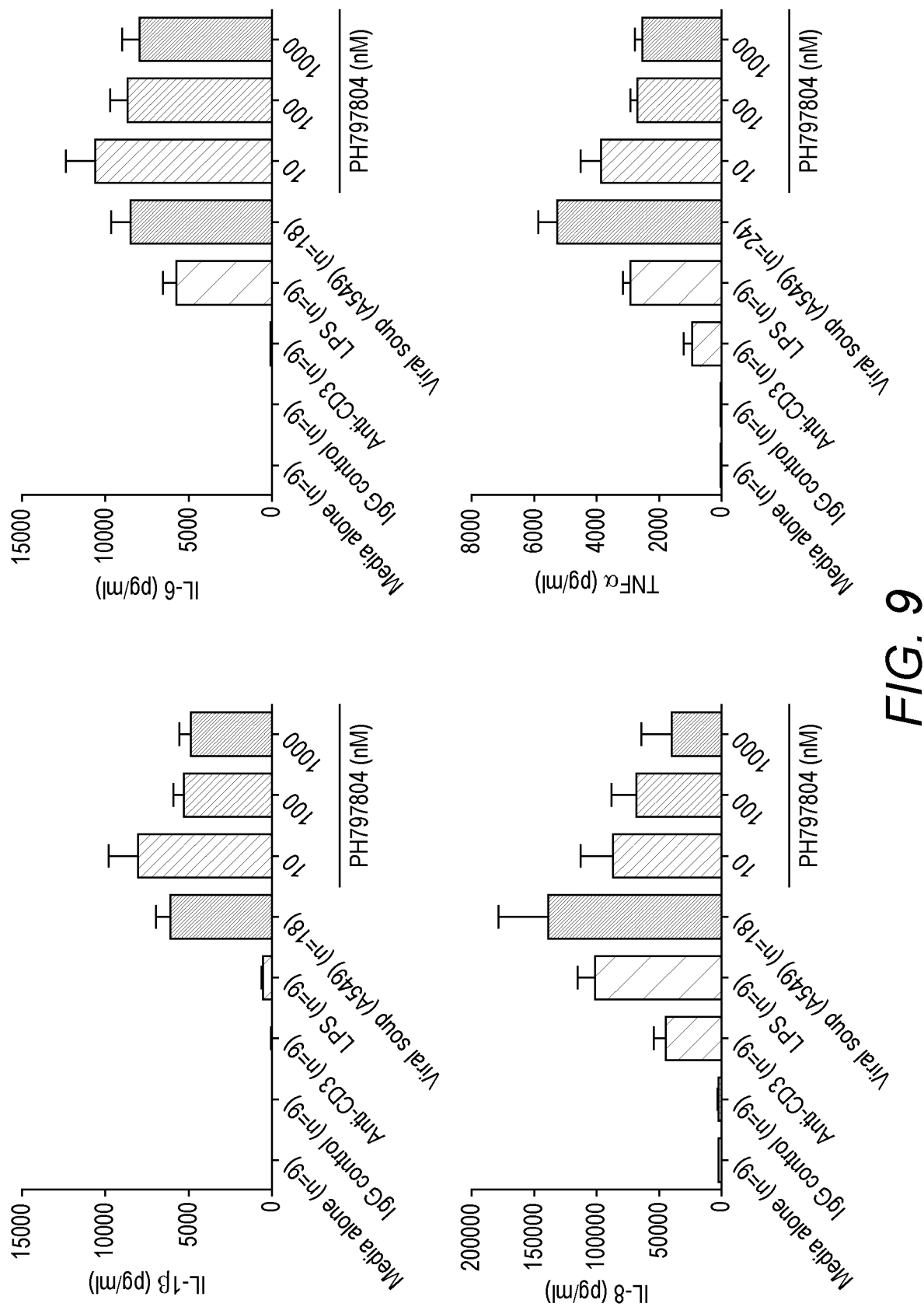

Additional ex vivo data were generated from immune cells whereby the induction of inflammatory mediators in response to A549 viral soup was compared to known inflammatory stimulants (anti-CD3 and LPS). The induction of TNFα, IL-1-β, IL-6 and IL-8 by A549 viral soup was found to be greater compared with these known inflammatory stimulants (FIG. 9).

Example 3 p38 MAPK Inhibitory Activity

The enzyme inhibitory activity of a compound may be determined by fluorescence resonance energy transfer (FRET) using synthetic peptides labelled with both donor and acceptor fluorophores (Z-LYTE, Invitrogen).

Recombinant, phosphorylated p38 MAPK gamma (MAPK12:Millipore) is diluted in HEPES buffer, mixed with the candidate compound at desired final concentrations and incubated for two hours at room temperature. The FRET peptide (2 μM) and ATP (100 μM) are next added to the enzyme/compound mixture and incubated for one hour. Development reagent (protease) is added for one hour prior to detection in a fluorescence microplate reader. The site-specific protease only cleaves non-phosphorylated peptide and eliminates the FRET signal. Phosphorylation levels of each reaction are calculated using the ratio of coumarin emission (donor) over fluorescein emission (acceptor) with high ratios indicating high phosphorylation and low ratios, low phosphorylation levels. The percentage inhibition of each reaction is calculated relative to non-inhibited control, and the 50% inhibitory concentration ($IC_{50}$ value) then calculated from the concentration-response curve.

For p38 MAPK alpha (MAPK14: Invitrogen), enzyme activity is evaluated indirectly by determining activation/phosphorylation of the down-stream molecule, MAPKAP- K2. The p38 MAPK a protein is mixed with its inactive target MAPKAP-K2 (Invitrogen) and the candidate compound for two hours at room temperature. The FRET peptide (2 μM), which is a phosphorylation target for MAPKAP-K2, and ATP (10 μM) are then added to the enzymes/compound mixture and incubated for one hour. Development reagent is then added and the mixture incubated for one hour before detection by fluorescence completed the assay protocol.

Example 4

P38MAPK Inhibition (p38i) Versus Inhibition of Other Potential Targets

As indicated in Example 1 above, a number of targetable nodes in the 95 pathway routes highlighted by transcriptomic and bioinformatics were identified. The compound profiling experiments in Example 2 show that p38i is effective in reducing the production of inflammatory mediator release in cell types relevant to the pathology of severe influenza. This was found not to be the case for 9 other nodes that were examined: PI3K, MEK, ERK, JNK, JAK/STAT, PKC, SRC, BtK and mTor. Drug inhibition of none of these 9 nodes gave an inhibition profile as effective as p38i in epithelial, endothelial and immune cells.

Figure 10:
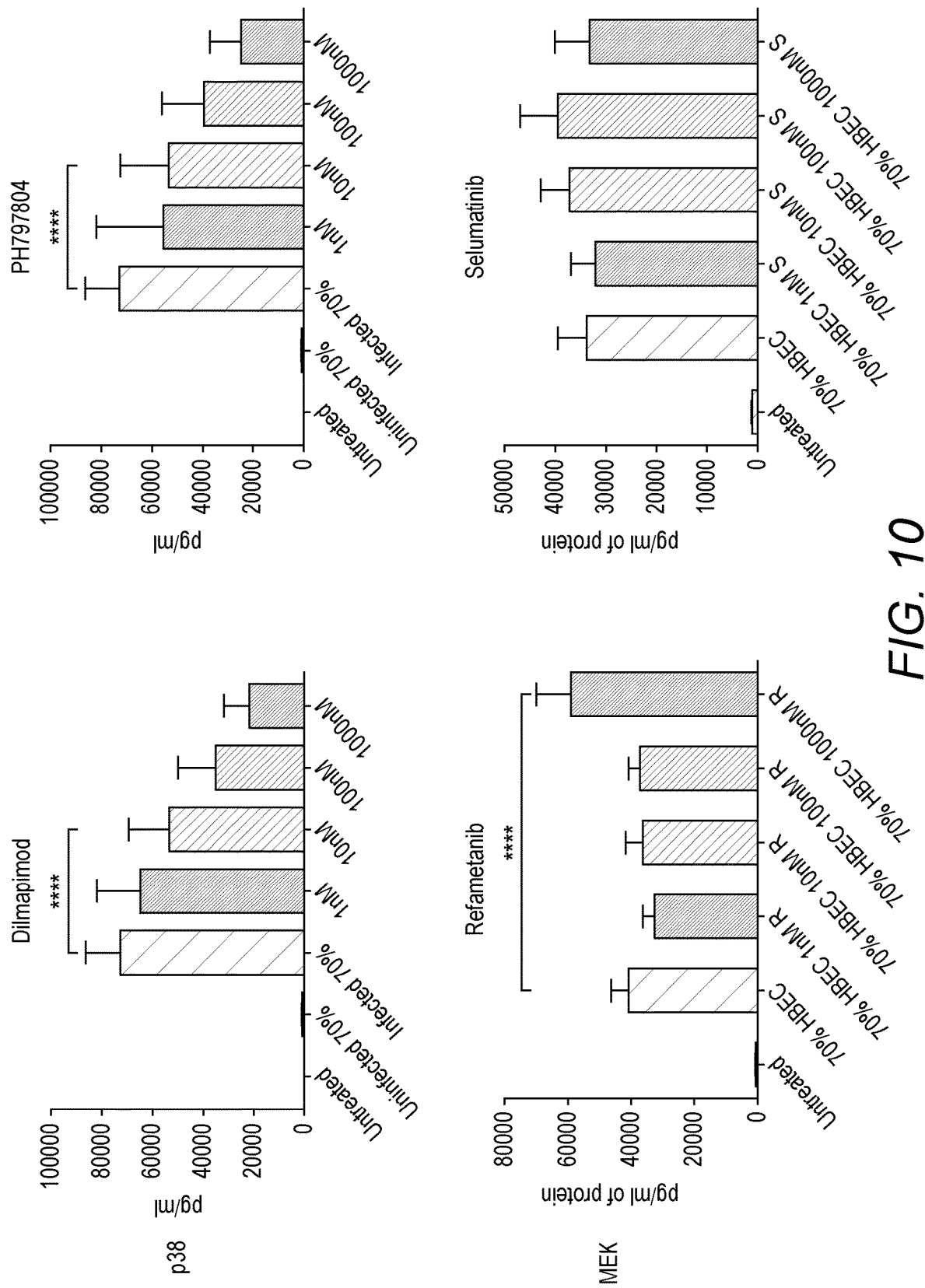

By way of example, data comparing p38i versus mitogen-activated protein kinase (MEK) inhibition (MEKi) by MEK inhibitors Refametinib (Iverson C et al., RDEA119/BAY 869766: a potent, selective, allosteric inhibitor of MEK1/2 for the treatment of cancer. *Cancer Res.,* 2009; 69: 6839-6847) and Selumetinib (Huynh H et al., Targeted inhibition of the extracellular signal-regulated kinase pathway with AZD6244 (ARRY-142886) in the treatment of hepatocellular carcinoma, *Molecular Cancer Therapeutics,* 2007; 6:138-146) are presented in FIG. 10 of the accompanying drawings.

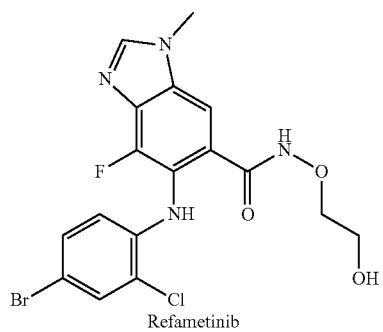

Refametinib

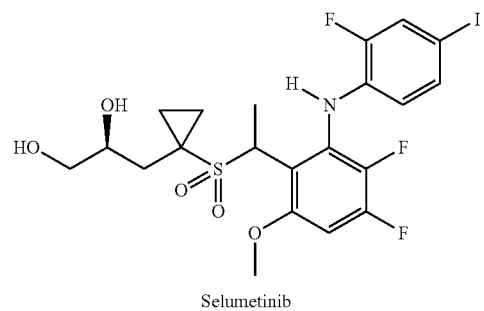

Selumetinib

Neither Refametinib nor Selumetinib showed dose-dependent inhibition of IP10 production in endothelial cells stimulated with HBEC viral soup and actually appeared to increase levels of IP10 at higher drug concentrations (see FIG. 10).

A number of potential drug targets have been proposed for severe influenza (e.g. Liu Q et al., 2015 and Fedson DS, 2009). p38i was also compared versus drug compounds for a selection of these proposed targets.

For these experiments, PH797804 was benchmarked versus corticosteroid (methyl prednisolone), macrolide (Azithromycin), PPAR agonist (Pioglitazone), PDE4 inhibitor (Roflumilast), NFκB inhibitor (EVP4593) and statin (Pravastatin) at four drug concentrations (1 nM, 10 nM, 100 nM and 1000 nM) in endothelial cells (HUVECs stimulated with HBEC viral soup), or immune cells (PBMCs plus granulocytes stimulated with A549 viral soup as described in Example 2 above).

The effects of drug compound administration on IP-10, IL-8 and MCP-1 production from endothelial cells and on IL-1β, IL-6, IL-8 and TNF-α production from immune cells was assayed using electrogenerated chemiluminescence. In immune cells, corticosteroid and macrolide drug treatment showed dose-dependent inhibition of all four assayed cytokines, whereas p38i showed dose-dependent inhibition of only three of the four. The inhibitory profile of the other drugs tested was variable and did not match that of corticosteroid, macrolide, or p38i. The results are summarised in Table 5 below.

TABLE 5

Comparison of inhibitory effects of drug compounds for literature-proposed targets for severe influenza versus p38i. PBMCs plus granulocytes were isolated as described in Example 2 and stimulated with A549 viral soup. Secreted cytokine levels were assayed by electrogenerated chemiluminescence and $IC_{50}$ and iMax values were calculated from the dose responses using non-linear regression fit using a scientific 2D graphing and statistics software package (GraphPad PRISM ® version 6.07 software). Where data did not show a dose-dependent inhibition, the $IC_{50}$ and iMax values were not calculated (empty boxes).

| | p38 inhibitor PH797804 | | Corticosteroid Methyl Prednisolone | | Macrolide Azithromycin | | PPAR agonist Pioglitazone | | PDE4 inhibitor Roflumilast | | NFkB inhibitor QNZ (EVP4593) | | Statin Pravastatin | |
|---|---|---|---|---|---|---|---|---|---|---|---|---|---|---|
| | $IC_{50}$ (nM) | iMax (%) | $IC_{50}$ (nM) | iMax (%) | $IC_{50}$ (nM) | iMax (%) | $IC_{50}$ (nM) | iMax (%) | $IC_{50}$ (nM) | iMax (%) | $IC_{50}$ (nM) | iMax (%) | $IC_{50}$ (nM) | iMax (%) |
| IL1B | 9.7 | 79% | 8.4 | 77% | 0.5 | 50% | | | | | | | | |
| IL8 | 2.3 | 87% | 8.4 | 90% | 0.8 | 46% | 0.1 | 37% | 0.09 | 31% | 0.2 | | | 47% |

TABLE 5-continued

Comparison of inhibitory effects of drug compounds for literature-proposed targets for severe influenza versus p38i. PBMCs plus granulocytes were isolated as described in Example 2 and stimulated with A549 viral soup. Secreted cytokine levels were assayed by electrogenerated chemiluminescence and $IC_{50}$ and iMax values were calculated from the dose responses using non-linear regression fit using a scientific 2D graphing and statistics software package (GraphPad PRISM ® version 6.07 software). Where data did not show a dose-dependent inhibition, the $IC_{50}$ and iMax values were not calculated (empty boxes).

| | p38 inhibitor PH797804 | | Corticosteroid Methyl Prednisolone | | Macrolide Azithromycin | | PPAR agonist Pioglitazone | | PDE4 inhibitor Roflumilast | | NFκB inhibitor QNZ (EVP4593) | | Statin Pravastatin | |
|---|---|---|---|---|---|---|---|---|---|---|---|---|---|---|
| | $IC_{50}$ (nM) | iMax (%) | $IC_{50}$ (nM) | iMax (%) | $IC_{50}$ (nM) | iMax (%) | $IC_{50}$ (nM) | iMax (%) | $IC_{50}$ (nM) | iMax (%) | $IC_{50}$ (nM) | iMax (%) | $IC_{50}$ (nM) | iMax (%) |
| TNFa | 3.9 | 91% | 20.2 | 79% | 86.9 | 63% | | | 10.8 | 74% | 43.6 | 37% | | |
| IL6 | | | 36.6 | 57% | 119 | 45% | 0.02 | 41% | | | | | | |

Figure 11:
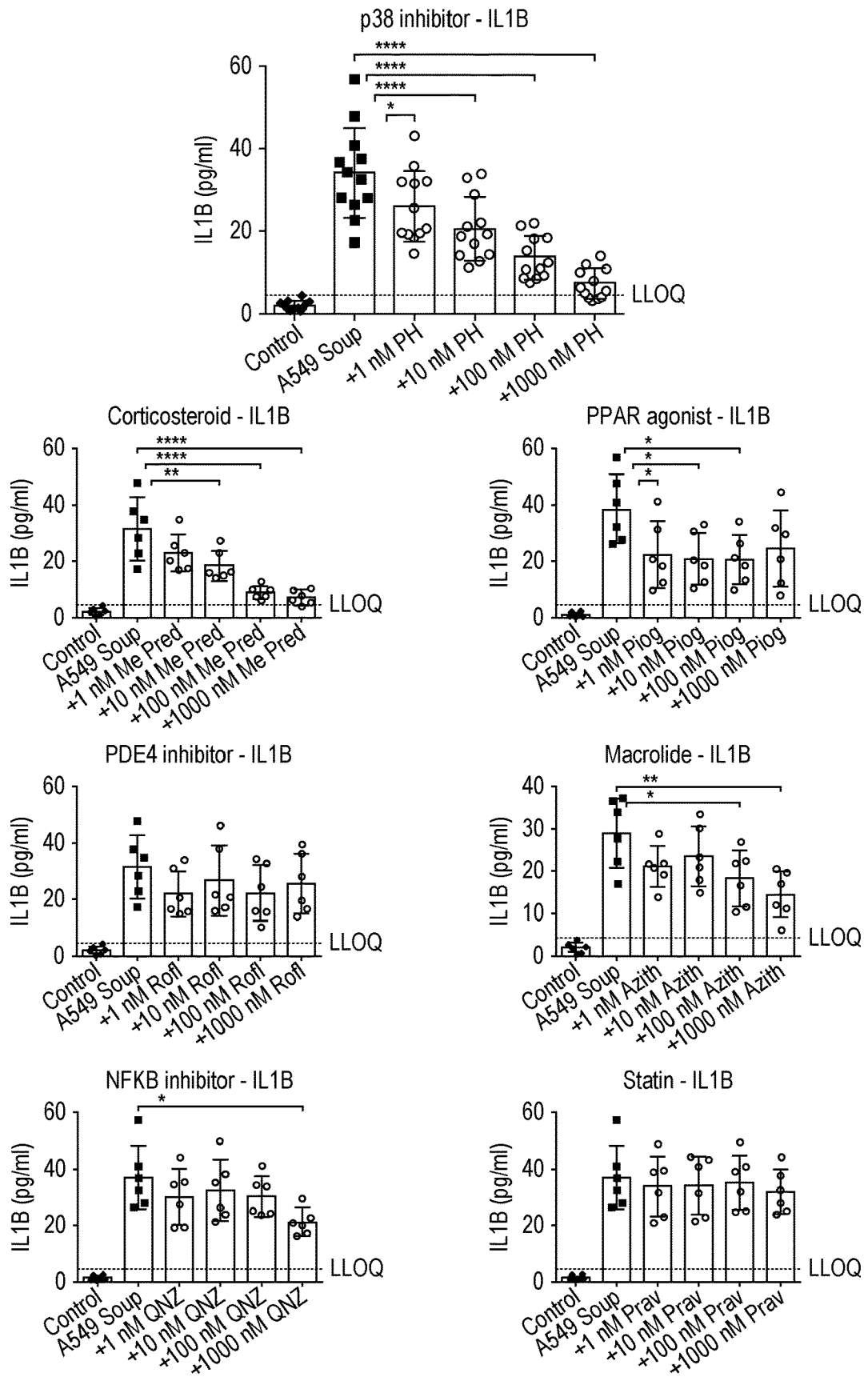
Figure 12:
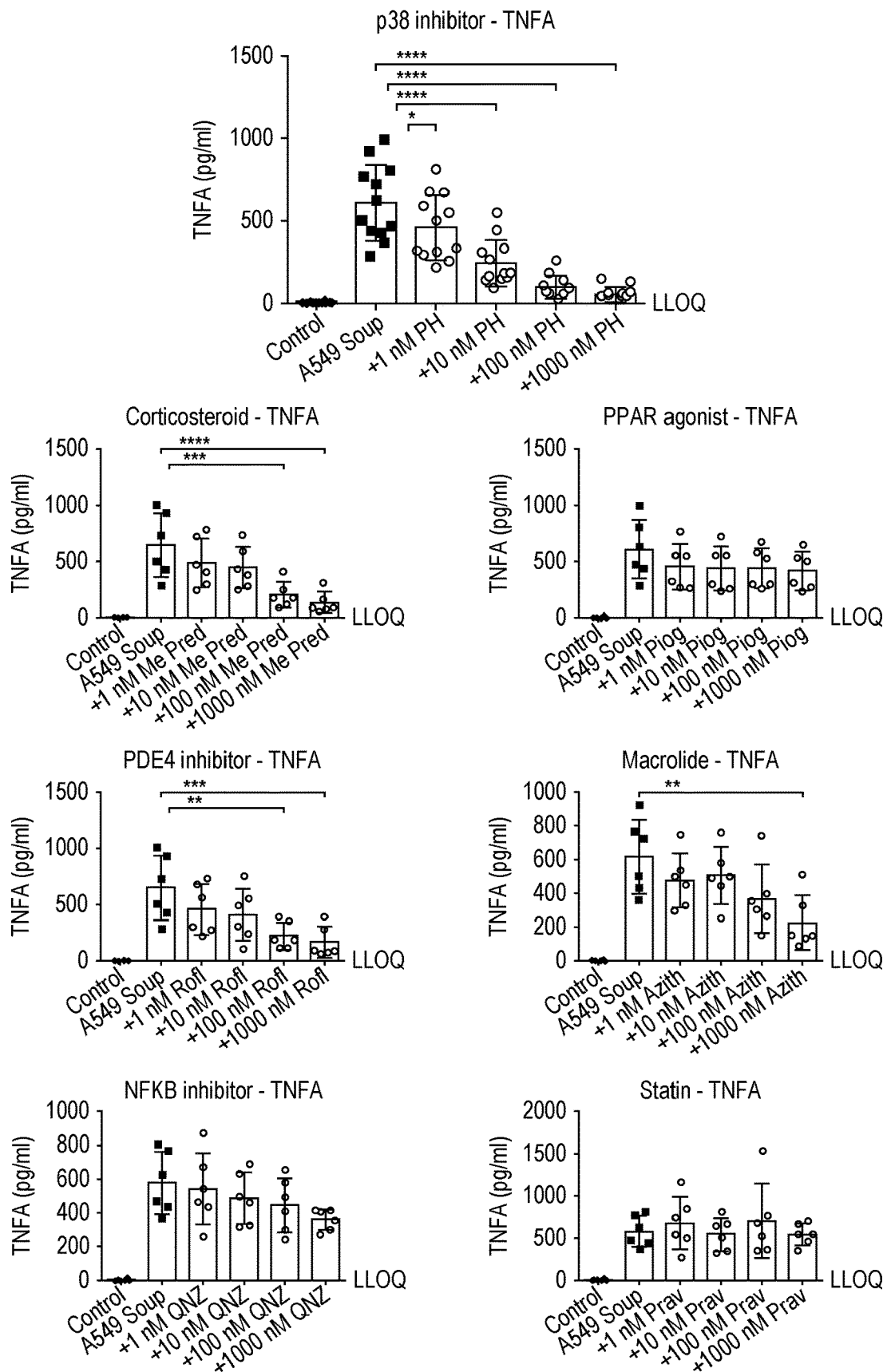

The inhibition plots for IL1-b and TNFa for the compounds tested are shown in FIGS. 11 and 12.

With endothelial cells, in contrast to immune cells, only p38 and NFκB inhibitors showed dose-dependent inhibition of the three cytokines assayed. None of the other drugs tested showed a comparable inhibitory effect. The results are summarised in Table 6 below.

TABLE 6

Comparison of inhibitory effects of drug compounds for literature-proposed targets for severe influenza versus p38i. HUVEC cells were stimulated with HBEC viral soup. Secreted cytokine levels were assayed by electrogenerated chemiluminescence and $IC_{50}$ and iMax values were calculated from the dose responses using non-linear regression fit with a scientific 2D graphing and statistics software package (GraphPad PRISM ® version 6.07 software). Where data did not show a dose-dependent inhibition, the $IC_{50}$ and iMax values were not calculated.

| | p38 inhibitor PH797804 | | Corticosteroid Methyl Prednisolone | | Macrolide Azithromycin | | PPAR agonist Pioglitazone | | PDE4 inhibitor Roflumilast | | NFκB inhibitor QNZ (EVP4593) | | Statin Pravastatin | |
|---|---|---|---|---|---|---|---|---|---|---|---|---|---|---|
| | $IC_{50}$ (nM) | iMax (%) | $IC_{50}$ (nM) | iMax (%) | $IC_{50}$ (nM) | iMax (%) | $IC_{50}$ (nM) | iMax (%) | $IC_{50}$ (nM) | iMax (%) | $IC_{50}$ (nM) | iMax (%) | $IC_{50}$ (nM) | iMax (%) |
| IP10 | 7.5 | 88% | | | | | | | | | 3.3 | 72% | 78 | 35% |
| IL8 | 28.9 | 86% | | | | | | | | | 6.5 | 60% | | |
| MCP1 | 13.1 | 36% | | | | | | | | | 3.84 | 44% | | |

Figure 13:
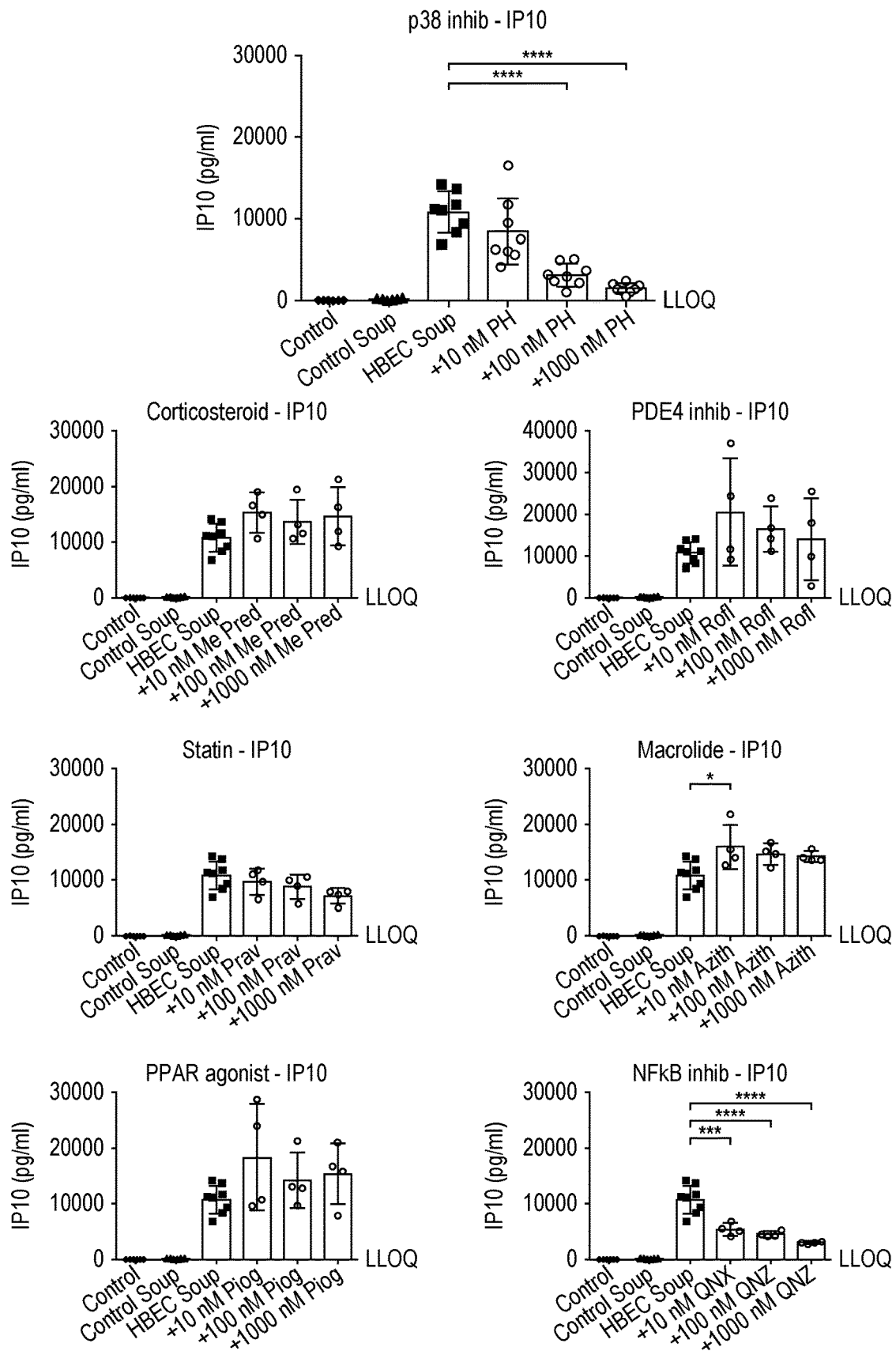
Figure 14:
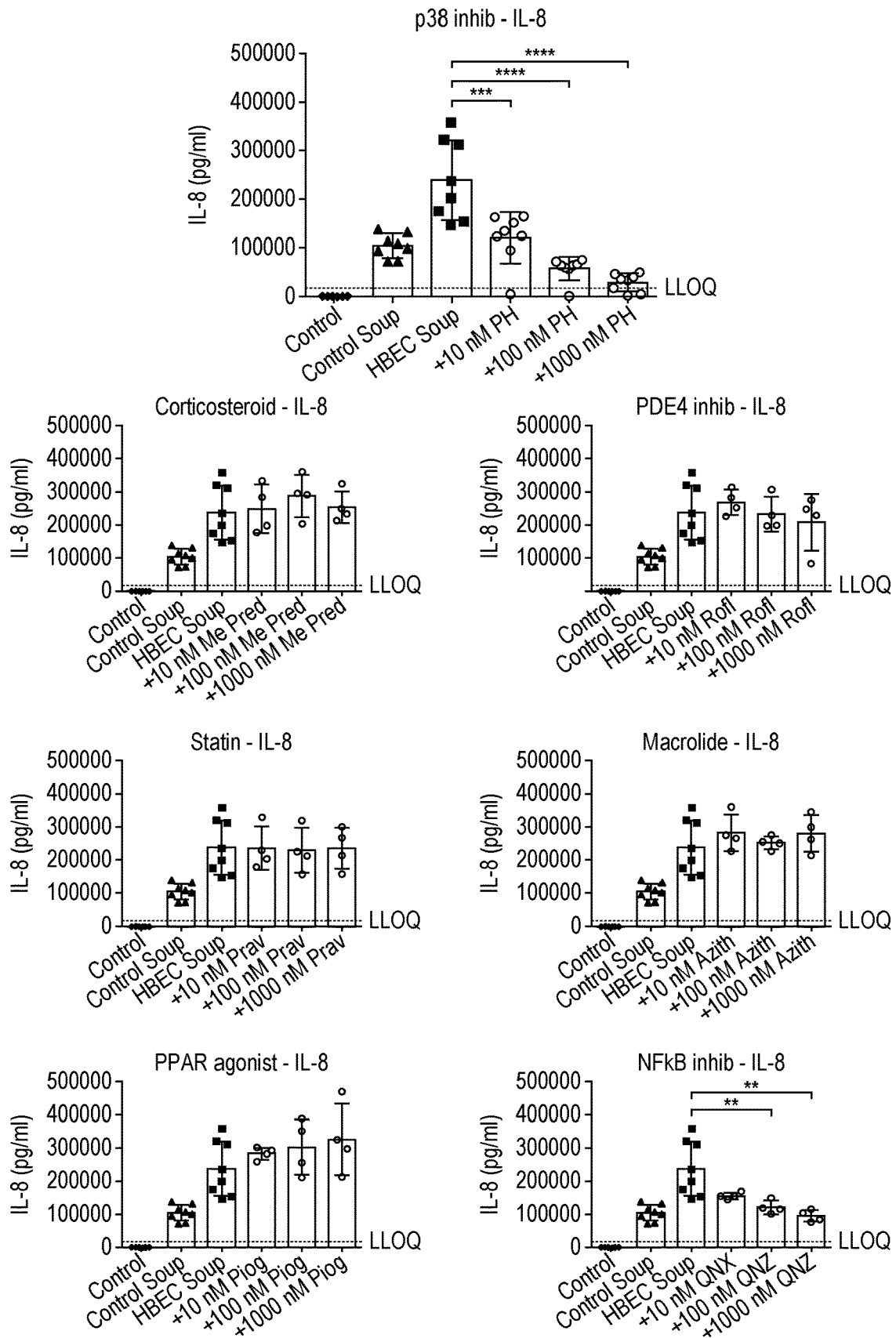

The inhibition plots for IP10 and IL8 are shown in FIGS. 13 and 14.

Based on the results obtained in the immune cell experiments, the superiority of p38i versus the other drugs was unexpected, especially methyl prednisolone, which is used routinely in clinical settings to treat a range of inflammatory diseases (e.g. asthma) and is commonly prescribed for severe influenza, although there is uncertainty over their potential benefit or harm (Rodrigo C et al., Corticosteroids as adjunctive therapy in the treatment of influenza, Cochrane Database of Systematic Reviews, 2016, Issue 3. Art. No.: CD010406. DOI: 10.1002/14651858.CD010406.pub2]. NFκB is downstream of p38, so the inhibition profile seen is not unexpected.

Example 5

Figure 15:
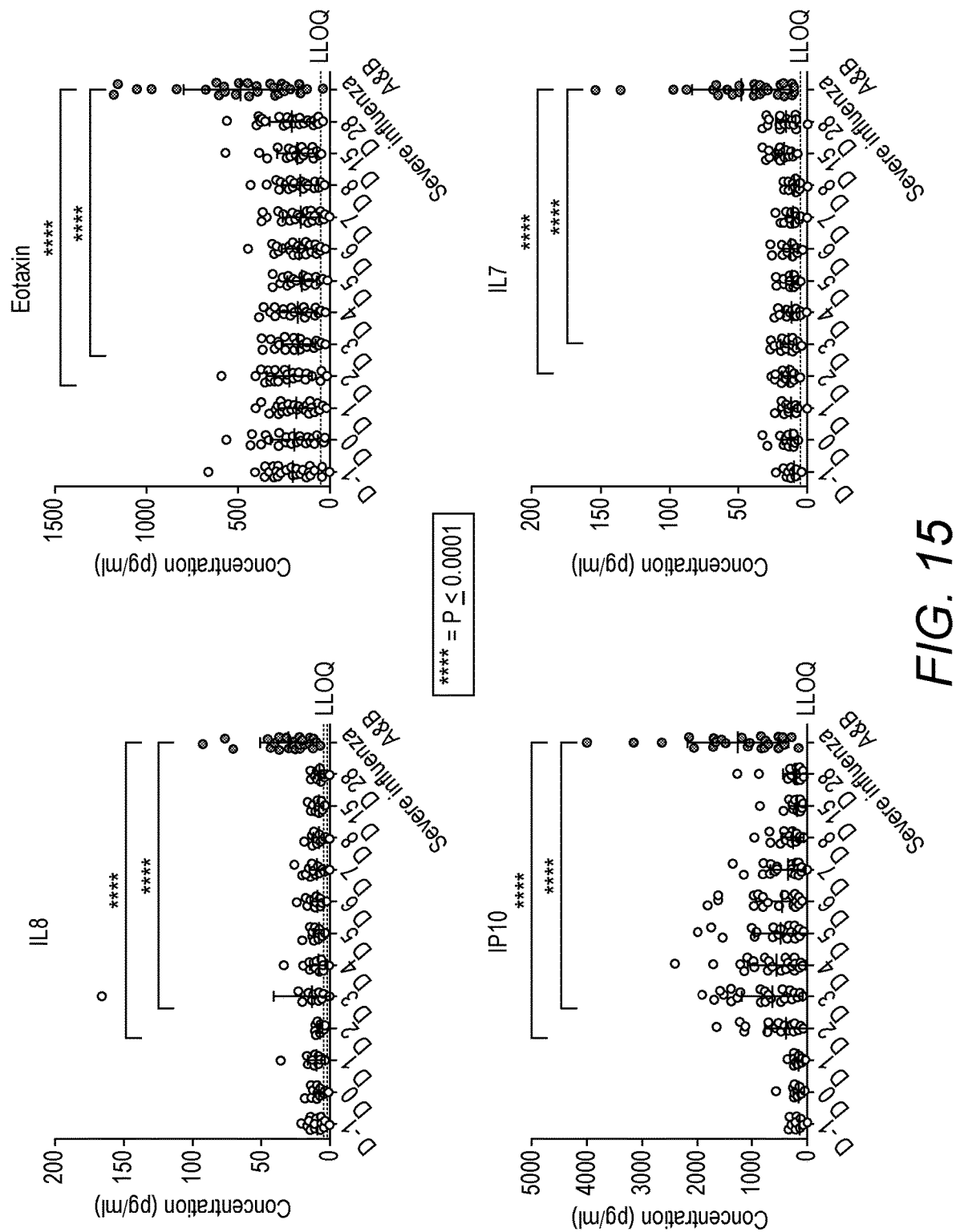

Levels of a Number of Cytokines in Serum from Patients Hospitalised for Severe Influenza Were Significantly Raised Relative to Influenza-Infected Individuals Without Severe Influenza Cytokine levels in serum samples from 30 subjects hospitalised with severe influenza during the 2015 influenza season and from 28 healthy subjects infected after intranasal inoculation with influenza A/H3N2 Perth/16/2009 virus were assayed using electrogenerated chemiluminescence. In the case of the former, a serum sample prepared from a blood sample collected 24-72 hours after the subject was admitted to hospital was analysed. In the case of the latter, serum was analysed from blood samples collected at 12 pre-determined intervals (Day −1 to Day 28). Eight cytokines were observed to be significantly raised in the hospitalised versus the infected healthy subjects: IL-8, IL-7, IL-16, Eotaxin, IP10, MCP1, MCP4 and VEGF. The results for four of these are shown in FIG. 15.

The results show that the hospitalised subjects are distinguishable from the healthy infected subjects in terms of their serum cytokine profiles.

Example 6

Effects of p38 MAPK Inhibition with the Compound of Formula III on Inflammatory Mediator Release in Key Cell Types Relevant to Severe or Persistent Influenza The p38 MAPK inhibitor of Formula III was used in in vitro and ex vivo experiments (Example 8 of WO 2004/076450 A1 (J. Uriach Y Compañia S. A.)).

Experimental testing of p38 MAPK inhibition by the inhibitor of Formula III was carried out in three cell types that are key players in the pathology of severe and persistent influenza: epithelial; endothelial; and immune cells (FIG. 4). In these experiments, cells were pre-treated with simple and/or complex stimuli in order to simulate the action of inflammatory mediators that are produced from influenza-infected epithelial cells. In the case of the former, tumour necrosis factor alpha (TNFa) plus interleukin 6 (IL-6) was used to stimulate endothelial and immune cells. In the case of the latter, conditioned medium (viral "soup") derived either from influenza virus infected A549 cells (adenocarcinoma human alveolar basal epithelial cells), or primary human bronchial epithelial cells (HBECs) was used to stimulate epithelial, endothelial and immune cells.

Epithelial Cells

For the production of conditioned medium (viral soup), A549 cells or HBECs were infected with high titre stocks of Influenza A/Perth/16/2009 (H3N2) virus. Viral stocks were produced by infection of Madin-Darby Canine Kidney [MDCK cells, available from the American Type Culture Collection as MDCK (NBL-2) (ATCC® CCL-34™)]. MDCK cells were cultured to 85-90% confluence in Minimal Essential Medium (MEM) containing 10% foetal bovine serum. Cells were washed twice with infection medium (Advanced Dulbecco's Modified Eagle Medium [DMEM] containing 1.06 USP/NF units per ml TPCK trypsin). The cells were infected with Influenza A/Perth/16/2009 (H3N2) virus stock at 0.01 MOI for one hour in infection medium. At the end of the incubation period, unbound virus particles were removed from the cells by washing once with infection medium. The cells were then overlaid with fresh infection medium and incubated for 48 hours at 37° C. in 5% $CO_2$/air. After incubation, the flasks of cells were frozen at −80° C. for 24 hours, thawed at room temperature and virus supernatants were centrifuged (2000 g, 10 min) before pooling together, aliquoting and storing at −80° C.

The viral stocks prepared were used for the generation of viral soups. Viral growth kinetics were optimised by determining multistep growth curves. A549 cells or HBECs were infected with virus at an MOI of 0.01 at 37° C. for one hour. Following incubation, the cells were washed and overlaid with infection medium. The samples were harvested at various time points for 72 hours for viral titre determination by $TCID_{50}$ assay on MDCK cells and the presence of inflammatory mediators was assessed by MSD chemiluminescence assay using methods as recommended by the vendor (https://web.archive.org/web/20160522190937/https://www.mesoscale.com/).

For the preparation of A549 viral soup, cells were cultured in MEM plus 10% foetal bovine serum to 85-90% confluence. The cells were washed twice with infection medium then infected with Influenza A/Perth/16/2009 (H3N2) virus stock at 0.01 MOI for one hour in infection medium. Unbound virus was removed from the cells at the end of the incubation period by washing once with infection medium before overlaying with infection medium. The cells were incubated for 48 hours at 37° C. in 5% $CO_2$/air. After incubation, the viral soup was collected from the culture flasks, centrifuged (2000 g, 10 min) and pooled together. The viral soup was aliquoted and stored at −80° C. For the preparation of HBEC viral soup cells were cultured to passage P-3 or P-4 in Bronchial Epithelial Cell Growth Medium (BECGM; Lonza). For infection, cells were washed twice with BECGM then infected with Influenza A/Perth/16/2009 (H3N2) virus stock at 0.01 MOI for one hour in infection medium (BECGM containing 1.06 USP/NF units per ml TPCK trypsin). The cells were then overlaid with infection medium and incubated for 48 hours at 37° C. in 5% $CO_2$/air. The HBEC viral soup was then processed in a similar way to A549 soup.

Prior to experimental testing, levels of pro-inflammatory mediators in both A549 and HBEC soup preparations were measured by MSD chemiluminescence analysis. Both soup preparations were found to contain elevated levels of pro-inflammatory cytokines (IL1-β, IL-6, IL-8, IL-10, TNFα and RANTES; FIG. 5) and demonstrated to induce p38MAPK signalling by demonstration of phosphorylation of both p38MAPK and phosphorylation of the downstream signalling protein HSP27 by western blot analysis (FIG. 5). For western blotting, viral soup-treated cells were washed with PBS and lysed in RIPA buffer with protease inhibitor (Sigma-P8340), phosphatase inhibitor cocktails 2 and 3 (Sigma P5726 and P0044) and phosphatase inhibitors sodium orthovanadate and sodium fluoride (both, www.sigmaaldrich.com) on ice. Protein concentrations were determined using the Pierce BCA Protein Assay Kit (www.thermofisher.com). Equivalent concentrations of each sample in 4× Laemmli sample buffer (BIO-RAD 161-0747) with 2-mercaptoethanol were analysed on a 12% polyacrylamide gel in Tris-glycine-SDS buffer and then transferred to nitrocellulose membrane. Membranes were blocked using 5% milk powder, then hybridised with p38 MAPK rabbit antibody (Cell Signalling Technologies, cat. no. 9212S) and phosphorylated p38 MAPK rabbit antibody (Cell Signalling Technologies, cat. no. 9211S), or HSP27 antibody (Cell signalling Technologies, cat. no. 2402) and phospho-HSP27 antibody (Cell signalling Technologies, cat. no. 9709). Secondary antibodies were anti-rabbit HRP (Cell signalling Technologies catalogue no. CS7074P2) or anti-mouse HRP (Cell signalling, catalogue no. 7076S), respectively. Membranes were stripped for re-probing using Restore™ PLUS Western Blot Stripping Buffer (Life technologies #46430). The membranes were treated with Amersham ECL Prime Western Blotting Detection Reagent (GE/Amersham #RPN2232) and imaged using ChemiDoc™ Touch Imaging System (BIO-RAD). Analysis was performed using Image Lab software.

Figure 16:
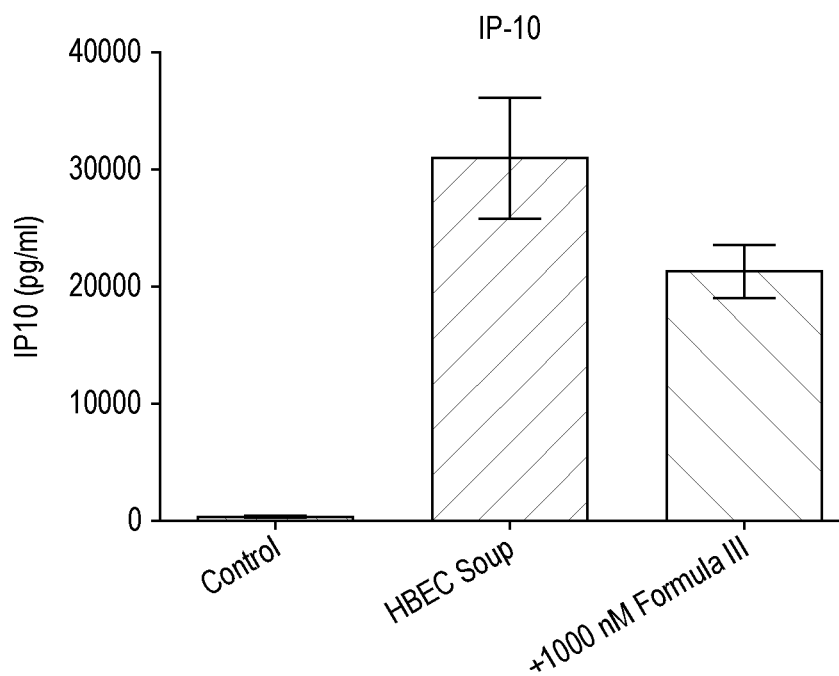
FIG. 16 shows the effect of HBEC viral soup on inflammatory mediator production in HBEC cells measured by MSD analysis and the inhibitory effect of the compound of Formula III.
Figure 16:
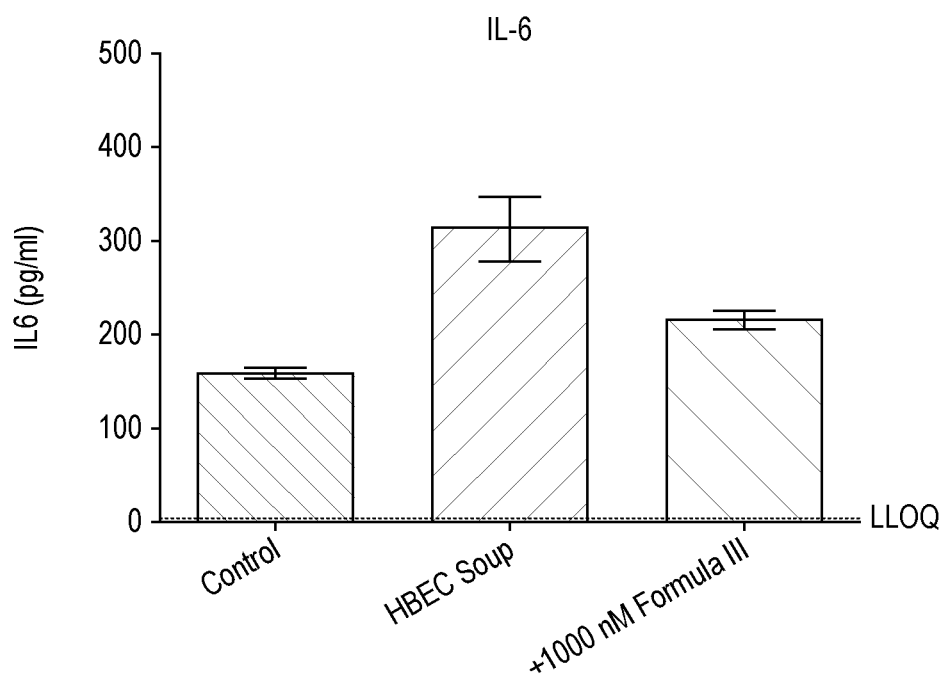

The effect of HBEC viral soup on inflammatory mediator production in HBEC cells was measured by MSD analysis. As shown in FIG. 16, HBEC soup induced the production of key inflammatory cytokines as exemplified by IL-6 and IP-10. Treatment of HBECs with the p38 MAPK inhibitor of Formula III prior to HBEC viral soup application attenuated release of both cytokines (FIG. 16).

Endothelial Cells

Both simple (TNFa plus IL-6) and complex (HBEC viral soup) stimuli were applied to Human Umbilical Vein Endothelial Cells (HUVECs) to simulate the interaction of inflammatory mediators produced by influenza-infected epithelial cells with endothelial cells.

Figure 17:
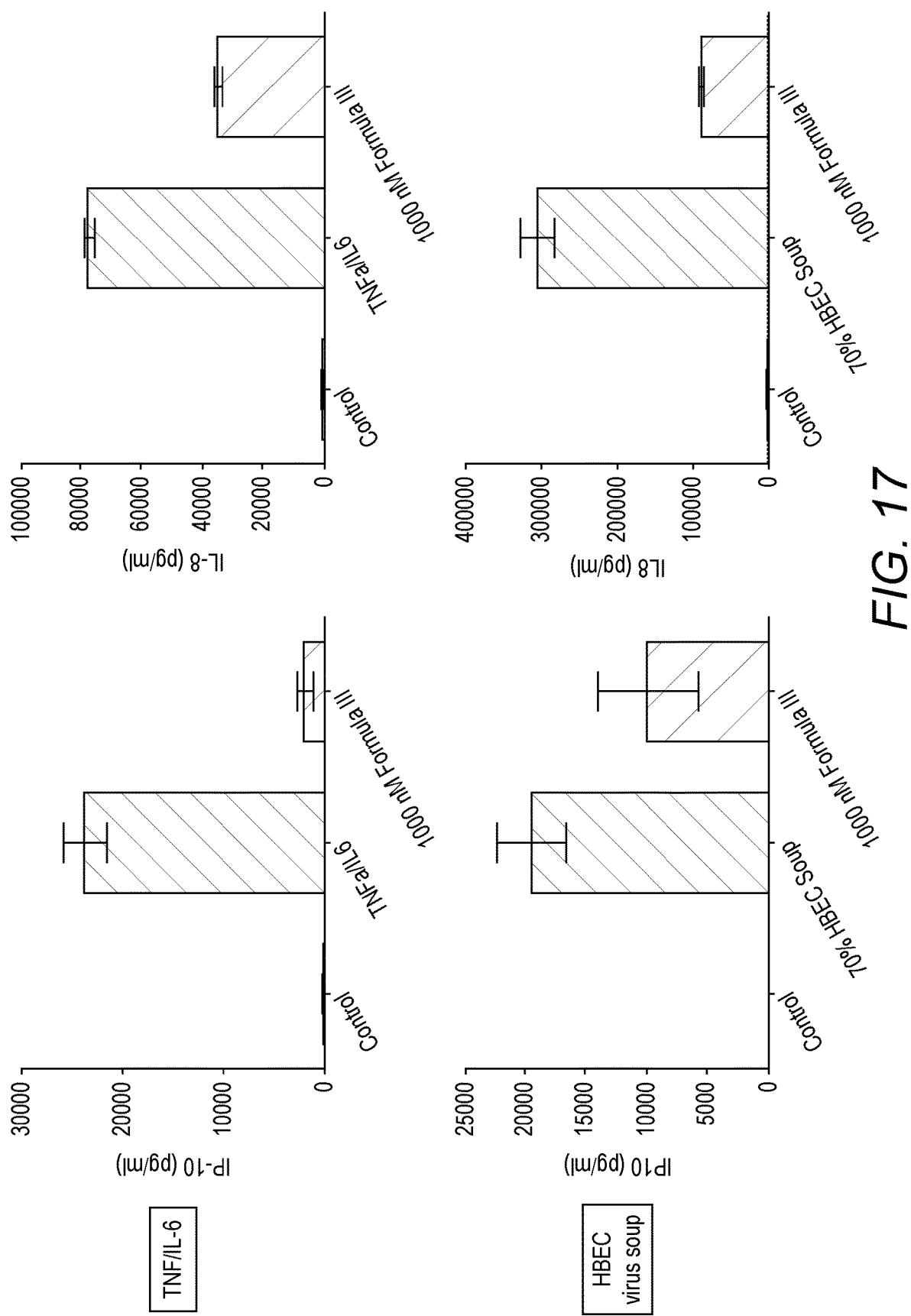
FIG. 17 shows inflammatory cytokine production by HUVEC cells treated with either TNFa plus IL-6, or HBEC viral soup as measured by MSD analysis in endothelial cells and the inhibitory effect of the compound of Formula III.

Inflammatory cytokine production by HUVEC cells treated with either TNFa plus IL-6, or HBEC viral soup as measured by MSD analysis was explored. As shown in FIG. 17, both stimuli induced the production of key inflammatory cytokines as exemplified by IL-8 and IP-10. However, treatment of HUVEC cells with p38 MAPK inhibitor of Formula III prior to stimulation was shown to attenuate this (FIG. 17).

Immune Cells

Both simple (TNFa plus IL-6) and complex (A549 viral soup) stimuli were applied to isolated human Peripheral Blood Mononuclear Cells (PBMCs) to simulate the interaction of inflammatory mediators that are produced from influenza-infected epithelial cells on immune cells. PBMCs were isolated from human blood according to the manufacturers recommendations (Boyum, A., Separation of leucocytes from blood and bone marrow, *Scand. J. Clin. Lab. Invest.*, 1968, 21, suppl. 97).

Figure 18:
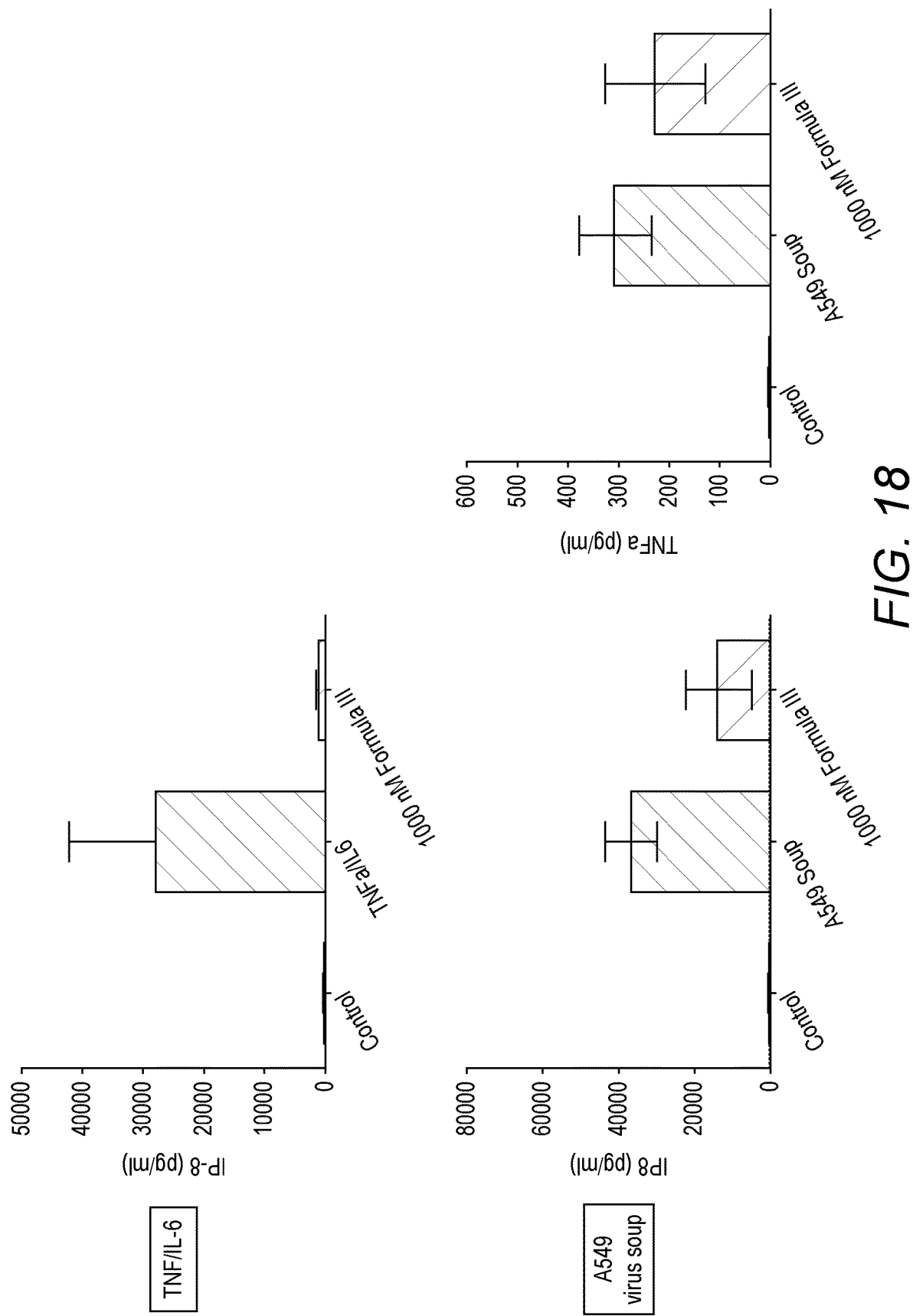
FIG. 18 shows inflammatory cytokine production in immune cells treated with either TNFa plus IL-6, or A549 viral soup as measured by MSD analysis in immune cells and the inhibitory effect of the compound of Formula III.

Inflammatory cytokine production in immune cells treated with either TNFa plus IL-6, or A549 viral soup as measured by MSD analysis was explored. As shown in FIG. 18, both stimuli induced the production of key inflammatory cytokines as exemplified by TNFα and IL-8. However, treatment of PBMCs with the p38 MAPK inhibitor of Formula III prior to stimulation was found to attenuate this (FIG. 18).

Example 7

Combination of the p38 MAPK Inhibitors with the Antiviral Drug Oseltamivir

Successful therapy of severe influenza is envisaged to depend on effectively targeting both the viral infection phase (phase 1) via antiviral drugs and the later (post-infection) inflammatory phase (phase 2) with immunomodulatory drugs. As antiviral treatment is recommended as early as possible for any patient with confirmed or suspected influenza who: is hospitalised; has severe, complicated, or progressive illness; or is at higher risk for influenza complications [https://www.cdc.gov/flu/professionals/antivirals/summary-clinicians.htm], it is important that an immunomodulator does not impede the action of the antiviral drug as both will likely be given at the same time. To examine this possibility the effect of combining oseltamivir with either of two p38MAPK inhibitors (PH797804 and Dilmapimod) was investigated by examining the effect that these two drugs had on the ability of oseltamivir to suppress viral infection in HBECs.

Figure 19:
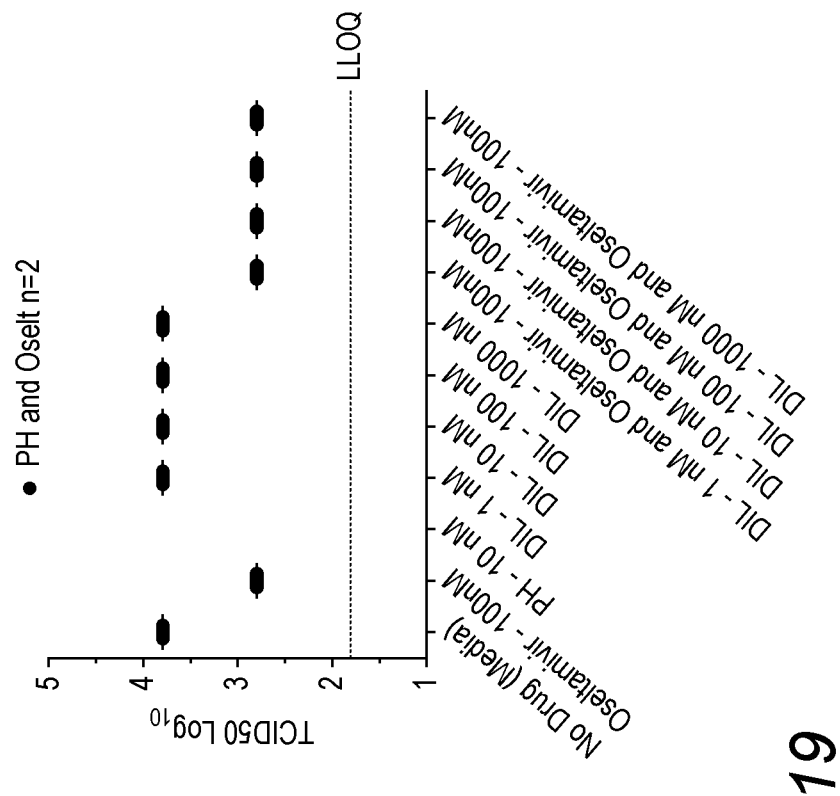
FIG. 19 shows the effect of combining p38 MAPK inhibitors with oseltamivir.
Figure 19:
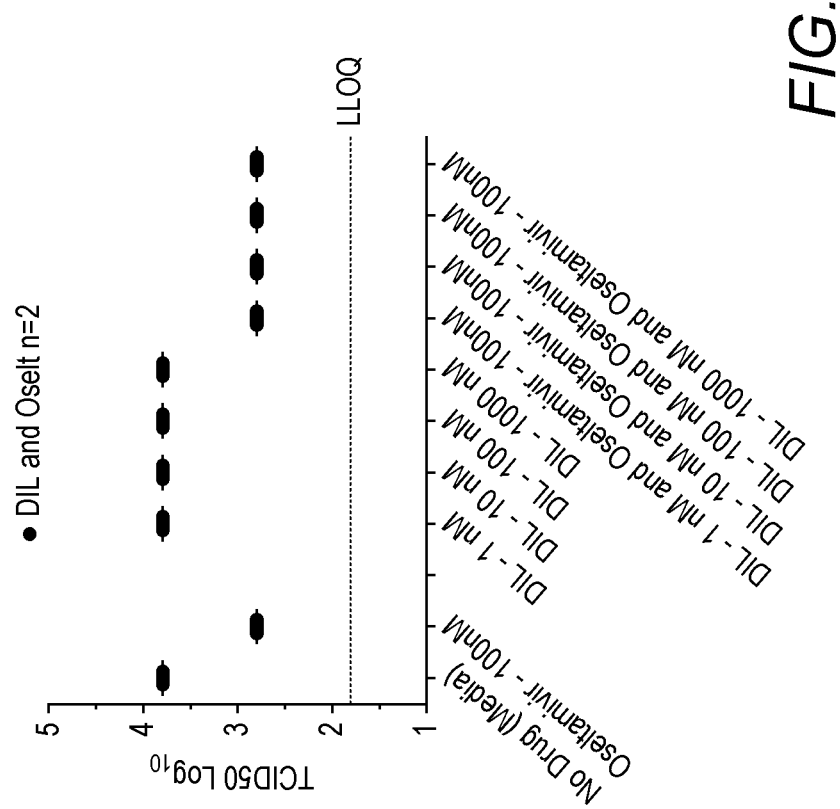

HBECs were infected with Influenza A/Perth/16/2009 (H3N2) virus stock at 0.01 MOI and the effect of oseltamivir in combination with either PH797804 or Dilmapimod on viral infection was examined. The oseltamivir used in this Example was in the form of oseltamivir carboxylate, which is the active metabolite of oseltamivir and pharmaceutically acceptable salts thereof (e.g. it is the active metabolite of oseltamivir phosphate). Viral titre was determined by $TCID_{50}$ assay [WHO manual for the laboratory diagnosis and virological surveillance of influenza; http://whqlibdoc.who.int/publications/2011/9789241548090_eng.pdf]. Whereas oseltamivir treatment reduced $TCID_{50}$, neither PH797804 nor Dilmapimod treatment showed this effect. When oseltamivir was combined with either PH797804 or Dilmapimod, $TCID_{50}$ was reduced to the level seen with oseltamivir on its own, indicating that p38MAPK inhibitor therapy could be used in combination with oseltamivir without impacting its antiviral activity (FIG. 19).

In a clinical setting it is envisaged that reduction of viral load (phase 1) by antiviral therapy would be monitored by measuring viral RNA levels using quantitative reverse transcriptase polymerase chain reaction (qRT-PCR), and effects of p38 inhibition on inflammation (phase 2) would be monitored by measuring the levels of inflammatory mediators such as those seen in patients with severe influenza (example 5) by, for example, MSD analysis of serum samples.

Example 8

Effects of p38 MAPK Inhibition with the Compound of Formula II on Inflammatory Mediator Release in Key Cell Types Relevant to Severe or Persistent Influenza The p38 MAPK inhibitor of Formula II was used in in vitro and ex vivo experiments (Example 18 of WO 2004/076450 A1 (J. Uriach Y Compañia S. A.)). As described above, the chemical structure of this compound is as follows:

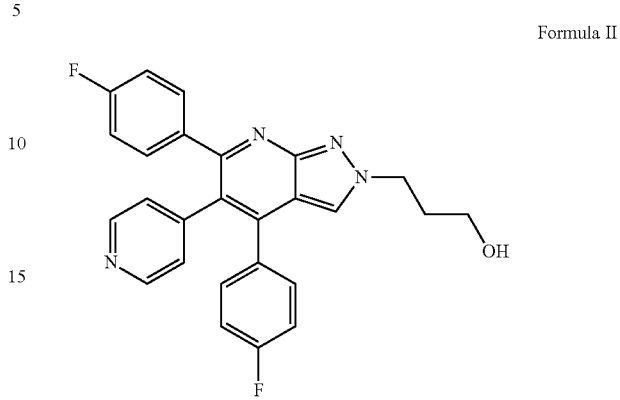

Formula II

Experimental testing of p38 MAPK inhibition by the inhibitor of Formula II was carried out in endothelial and immune cells. In these experiments, cells were pre-treated with TNFa plus IL-6, or viral soups prepared as described above in [00190] to [00193].

Endothelial Cells

Figure 20:
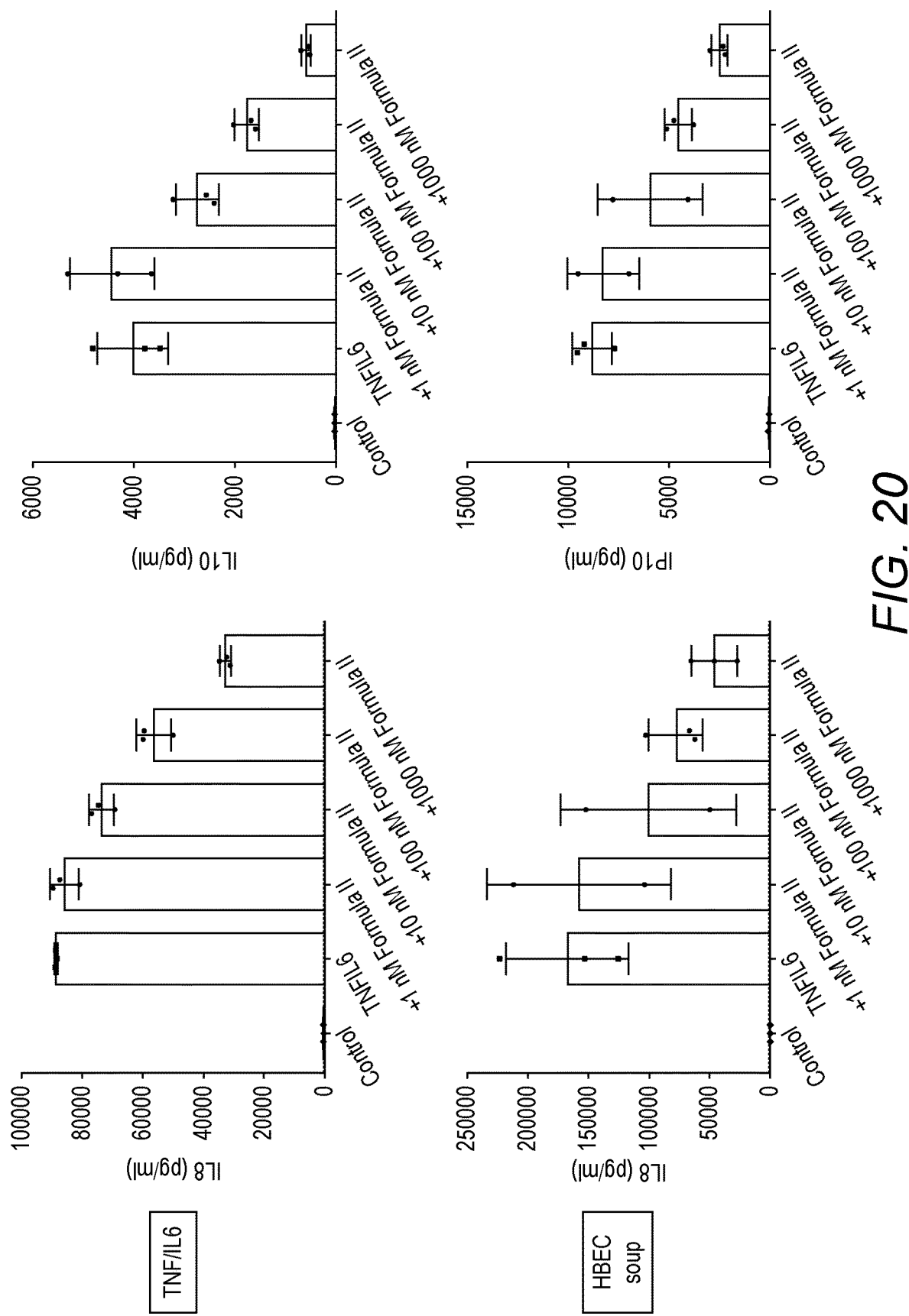
FIG. 20 shows inflammatory cytokine production by HUVEC cells treated with either TNFa plus IL-6, or HBEC viral soup as measured by MSD analysis in endothelial cells and the inhibitory effect of the compound of Formula II.

Inflammatory cytokine production by HUVEC cells treated with either TNFa plus IL-6, or HBEC viral soup was measured by MSD analysis. As shown in FIG. 20, both stimuli induced the production of key inflammatory cytokines as exemplified by IL-8 and IP-10. However, treatment of HUVEC cells with p38 MAPK inhibitor of Formula II prior to stimulation was shown to attenuate this (FIG. 20).

Immune Cells

Both simple (TNFa plus IL-6) and complex (A549 virus soup) stimuli were applied to isolated human Peripheral Blood Mononuclear Cells (PBMCs) to simulate the interaction of inflammatory mediators that are produced from influenza-infected epithelial cells on immune cells. PBMCs were isolated from human blood according to the manufacturer's recommendations (Boyum, A., Separation of leucocytes from blood and bone marrow, Scand. J. Clin. Lab. Invest., 1968, 21, suppl. 97).

Figure 21:
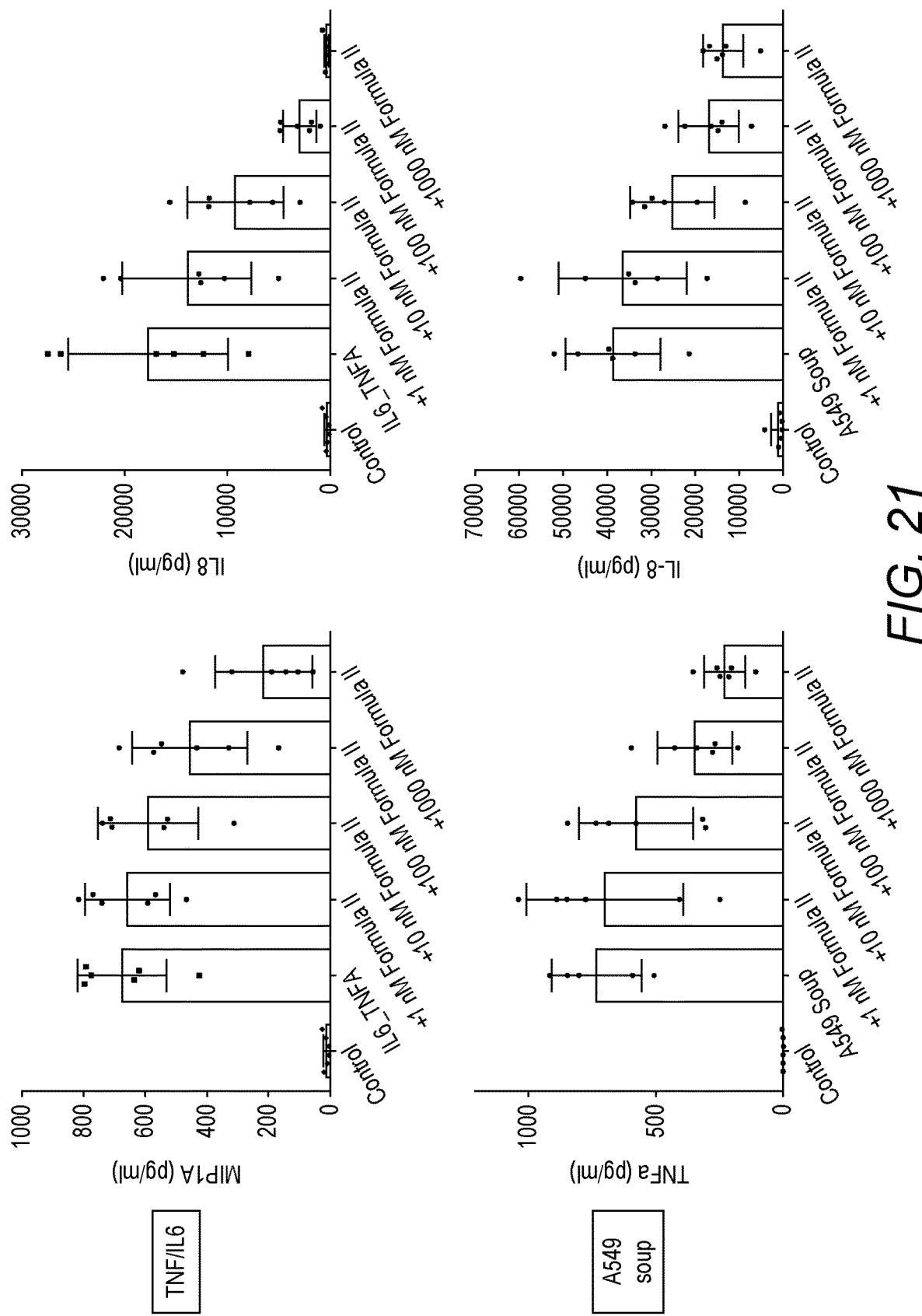
FIG. 21 shows inflammatory cytokine production in immune cells treated with either TNFa plus IL-6, or A549 viral soup as measured by MSD analysis in immune cells and the inhibitory effect of the compound of Formula II.

Inflammatory cytokine production in immune cells treated with either TNFa plus IL-6, or A549 virus soup as measured by MSD analysis was explored. As shown in FIG. 21, both stimuli induced the production of key inflammatory cytokines as exemplified by MIP-1a and IL-8 (TNFa plus IL-6 as stimulus) and TNFa and IL-8 (A549 virus soup as stimulus). However, treatment of PBMCs with the p38 MAPK inhibitor of Formula II prior to stimulation was found to attenuate this (FIG. 21).

Example 9

Combination of Compound with Formula II with the Antiviral Drug Oseltamivir

As it is important that an immunomodulator does not impede the action of antiviral drugs that are likely to be given at the same time, the effect of combining compound of Formula II with oseltamivir was investigated by examining the effect that this drug compound has on the ability of oseltamivir to suppress viral infection in HBECs. Conversely, the effect that this combination might have on the anti-inflammatory properties of compound with Formula II was also examined.

Figure 22:
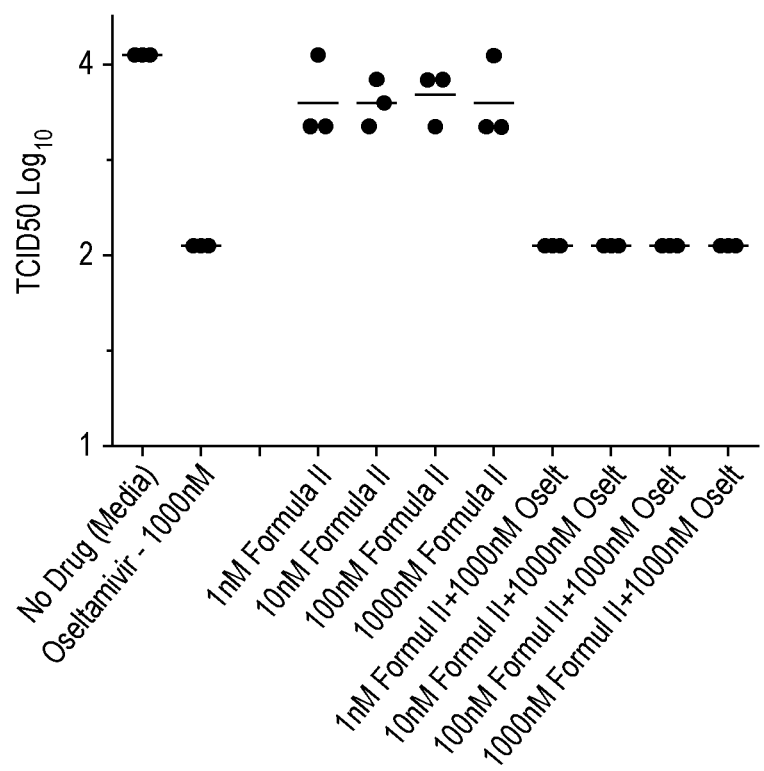
FIG. 22 shows the effect of combining the compound of Formula II with oseltamivir on the anti-viral properties of oseltamivir.
Figure 23:
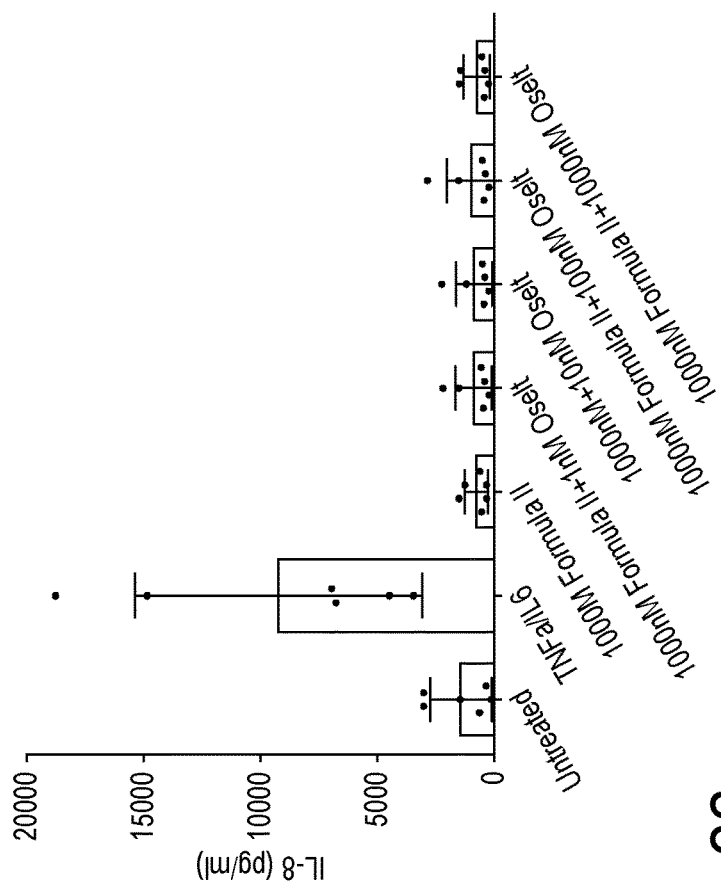
FIG. 23 shows the effect of combining oseltamivir the compound of Formula II on the anti-inflammatory properties of the compound of Formula II.
Figure 23:
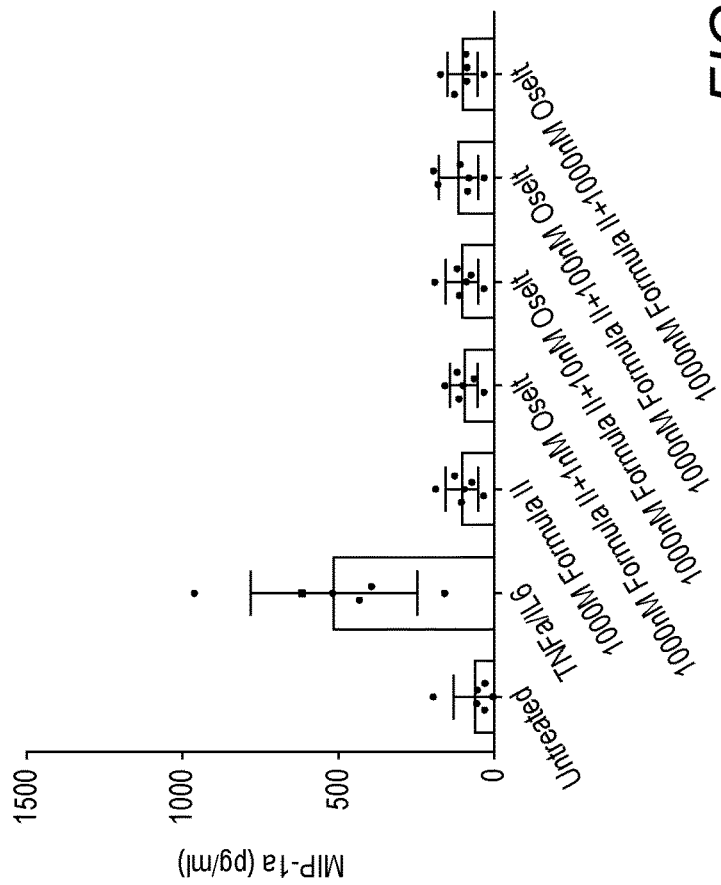

HBECs were infected with Influenza A/Perth/16/2009 (H3N2) virus stock at 0.01 MOI and the effect of oseltamivir in combination with compound of Formula II on viral infection was examined. The oseltamivir used in this Example was in the form of oseltamivir carboxylate, which is the active metabolite of oseltamivir and pharmaceutically acceptable salts thereof (e.g. it is the active metabolite of oseltamivir phosphate).Viral titre was determined by $TCID_{50}$ assay [WHO manual for the laboratory diagnosis and virological surveillance of influenza; http:/lwhqlibdoc.who.int/publications/2011/9789241548090 eng.pdf]. Whereas oseltamivir treatment alone reduced $TCID_{50}$, treatment with the compound of Formula II alone did not significantly reduce the $TCID_{50}$. When oseltamivir was combined with compound of Formula II, $TCID_{50}$ was reduced to the level seen with oseltamivir on its own, indicating that p38MAPK inhibitor therapy could be used in combination with oseltamivir without impacting oseltamivir's antiviral activity (FIG. 22). Conversely, oseltamivir alone had no observable effect on the anti-inflammatory properties of the compound of Formula II (FIG. 23).

In a clinical setting it is envisaged that reduction of viral load by antiviral therapy would be monitored by measuring viral RNA levels using quantitative reverse transcriptase polymerase chain reaction (qRT-PCR), and the effects of p38 inhibition on inflammation would be monitored by measuring the levels of inflammatory mediators such as those seen in patients with severe influenza (Example 5) by, for example, MSD analysis of serum samples.

Abbreviations
ATP Adenosine triphosphate
A549 Adenocarcinoma human alveolar basal epithelial cells
BECGM Bronchial epithelial cell growth medium
Btk Bruton's tyrosine kinase
CXCL8 Interleukin 8
CD3 Cluster of differentiation protein 3
DMEM Dulbecco's modified eagle medium
ERK Extracellular signal-regulated kinases)
FRET Fluorescence resonance energy transfer
GSK Glaxo Smith-Kline
HBEC Human bronchial epithelial cells
HEPES 4-(2-hydroxyethyl)-1-piperazineethanesulfonic acid
HSP27 Heat shock protein 27
HUVEC Human vascular endothelial cells
$IC_{50}$ Half maximal inhibitory concentration
iMax Maximal inhibition (as a %)
IL1-b Interleukin 1 beta
IL-6 Interleukin 6
IL-8 Interleukin 8
IPA Ingenuity Pathways Analysis
IP-10 Interferon gamma-induced protein 10
JAK/STAT Janus kinase/signal transducer and activator of transcription
JNK c-Jun N-terminal kinase
LPS Lipopolysaccharide
MAPKAP-K2 MAP kinase-activated protein kinase 2
MOI Multiplicity of infection
MCP-1 Monocyte chemotactic protein-1
MDCK Madin Darby canine kidney
MEK Mitogen-activated protein kinase kinase
MEKi MEK inhibition (by drug)
MEM Minimal essential medium
mTOR Mechanistic target of rapamycin
MSD Mesoscale Discovery
NFκB Nuclear factor kappa-light-chain-enhancer of activated B cells
P38 MAPK P38 Mitogen-activated protein kinases
P38i p38 inhibition (by drug)
PBMC Peripheral blood mononuclear cells
PBS Phosphate buffered saline
PDE4 Phosphodiesterase 4
PKC Protein kinase
PPAR Peroxisome proliferation-activated receptor
RANTES Regulated on activation, normal T cell expressed and secreted
RIPA Radio immuno precipitation assay
SDS Sodium dodecyl sulphate
SRC Src kinase
$TCID_{50}$ Tissue culture infective dose
TNFa/TNFα Tumour necrosis factor alpha
TPCK Tosyl phenylalanyl chloromethyl ketone
USP/NF United States pharmacopeia and the national formula

The invention claimed is:

1. A method of treating hypercytokinemia in a human or animal patient in need thereof comprising administering to the patient a therapeutically effective amount of a p38 MAP kinase inhibitor of Formula I, or a pharmaceutically acceptable salt or solvate thereof:

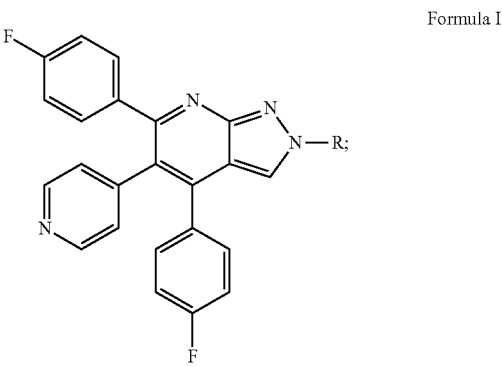

Formula I wherein R is $C_{1-3}$ alkyl, optionally substituted by one or more halo, $NR^1R^2$ or hydroxy, and $R^1$ and $R^2$ are independently H, halo or $C_{1-3}$alkyl, optionally substituted by one or more F.

2. The method of claim 1, wherein the p38 MAP kinase inhibitor is of Formula II, or a pharmaceutically acceptable salt or solvate thereof:

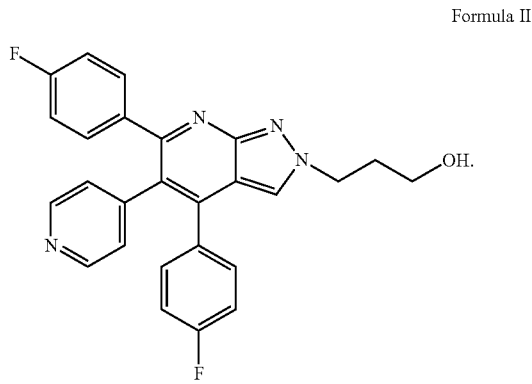

Formula II

3. The method of claim 1, wherein the p38 MAP kinase inhibitor is of Formula III, or a pharmaceutically acceptable salt or solvate thereof:

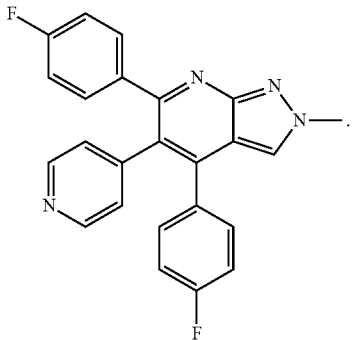

Formula III

4. The method of claim 1, wherein the hypercytokinemia occurs due to one or more of severe influenza virus infection; graft-versus-host disease (GVHD); acute respiratory distress syndrome (ARDS); sepsis; Ebola; smallpox; systemic inflammatory response syndrome (SIRS); bacterial infection; and cancer.

5. The method of claim 1, wherein the hypercytokinemia occurs due to severe influenza virus infection.

6. The method of claim 1, further comprising administering an antimicrobial agent.

7. The method of claim 6, wherein the antimicrobial agent is an antiviral agent.

8. The method of claim 7, wherein the antiviral agent is oseltamivir or a pharmaceutically acceptable salt thereof.

9. The method of claim 1, further comprising administering an anticancer agent.

10. The method of claim 1, wherein the p38 MAP kinase inhibitor is administered orally.

11. The method of claim 1, wherein the hypercytokinemia occurs due to exposure to a pathogen.

12. The method of claim 11, wherein the hypercytokinemia occurs due to a viral infection.

13. The method of claim 12, wherein the immune response in the patient is triggered by a respiratory viral infection.

14. The method of claim 13, wherein the hypercytokinemia occurs due to an influenza virus infection.

15. The method of claim 1, wherein the hypercytokinemia is triggered by cancer.

16. The method of claim 1, wherein the hypercytokinemia is triggered by an autoimmune response.

17. The method of claim 14, wherein the hypercytokinemia occurs due to a viral infection.

18. The method of claim 17, wherein the immune response in the patient is triggered by a respiratory viral infection.

19. The method of claim 18, wherein the hypercytokinemia occurs due to an influenza virus infection.

* * * * *